US010538558B2

(12) United States Patent
Sigalov

(10) Patent No.: US 10,538,558 B2
(45) Date of Patent: Jan. 21, 2020

(54) INHIBITION OF TCR SIGNALING WITH PEPTIDE VARIANTS

(71) Applicant: Signablok, Inc., Shrewsbury, MA (US)

(72) Inventor: Alexander B. Sigalov, Worcester, MA (US)

(73) Assignee: SIGNABLOK, INC, Shrewsbury, MA (US)

( * ) Notice: Subject to any disclaimer, the term of this patent is extended or adjusted under 35 U.S.C. 154(b) by 0 days.

(21) Appl. No.: 16/166,984

(22) Filed: Oct. 22, 2018

(65) Prior Publication Data

US 2019/0241618 A1   Aug. 8, 2019

Related U.S. Application Data

(63) Continuation of application No. 12/895,454, filed on Sep. 30, 2010, now Pat. No. 10,138,276.

(60) Provisional application No. 61/247,033, filed on Sep. 30, 2009.

(51) Int. Cl.
| | | |
|---|---|---|
| *C07K 14/005* | (2006.01) | |
| *A61K 51/10* | (2006.01) | |
| *A61K 38/00* | (2006.01) | |

(52) U.S. Cl.
CPC ............ *C07K 14/005* (2013.01); *A61K 38/00* (2013.01); *A61K 51/1039* (2013.01); *C12N 2710/16422* (2013.01); *C12N 2710/16522* (2013.01)

(58) Field of Classification Search
CPC .. A61K 2300/00; A61K 38/00; A61K 47/646; A61K 31/715; C07K 2317/76; C07K 16/28; C12N 2310/351; C12N 2310/3515
See application file for complete search history.

(56) References Cited

U.S. PATENT DOCUMENTS

| | | | | |
|---|---|---|---|---|
| 6,057,294 | A | 5/2000 | Manolios | 514/13 |
| 6,221,352 | B1 | 4/2001 | Howell et al. | 424/184.1 |
| 2005/0070478 | A1 | 3/2005 | Manolios | 514/15 |
| 2007/0185025 | A1 | 8/2007 | Palacios et al. | 424/218.1 |
| 2008/0096809 | A1 | 4/2008 | Shai | 514/12 |
| 2009/0075899 | A1 | 3/2009 | Sigalov | 514/9.7 |

FOREIGN PATENT DOCUMENTS

| | | |
|---|---|---|
| WO | WO/1996/022306 | 7/1996 |
| WO | WO/1997/047644 | 12/1997 |
| WO | WO/2005/044992 | 5/2005 |
| WO | WO/2006/076410 | 7/2006 |
| WO | WO/2006/077601 | 7/2006 |
| WO | WO 2007034490 A2 * | 3/2007 ............ C07K 14/07 |
| WO | WO/2008/076275 | 6/2008 |

OTHER PUBLICATIONS

Allen et al. J Pept Res 2005;65:591-604.
Amon et al. Lipidation and glycosylation of a T cell antigen receptor (TCR) transmembrane hydrophobic peptide dramatically enhances in vitro and in vivo function. Biochimica et Biophysica Acta 1763 (2006) 879-888.
Bloch et al. Faseb J 2007;21 :393-401.
Call et al. Cell 2002: 111:967-79.
Chemistry of Peptide Synthesis, N. Leo Benoiton (ed.), CRC, 2005.
Cohen et al. Biochemistry 2008;4 7:4826-33.
Collier et al. Scand J Immunol 2006;64:388-91.
Deisseroth et al., "Use of Blood And Blood Products" in Cancer: Principles And Practice Of Oncology, Devita V. T. Jr. et al. Editors, Philadelphia: J. B. Lippincott Company 1989, 2045-59.
Drug Discovery And Evaluation: Pharmacological Assays, Hans G, Vogel (ed.) Springer Berlin Heidelberg, 2007.
Gambier J.C. Curr Opin Immunol 1992;4:257-64.
Garnier et al. Methods Enzymol 1996;266:540-53.
Gerber et al. FAS EB J 2005; 19: 1190-2.
Guermeur et al. Bioinformatics 1999;15:413-21.
Harbury et al. Science 1998;282:1462-7.
Jerome K.R. J Viral 2008;82:4194-204.
Keegan, A.D. and Paul W.E .. Immunol Today 1992;13:63-68.
Kim W.M. and Sigalov A.B. Adv Exp Med Biol 2008;640:325-49.
Kliger et al. J Biol Chem 1997;272: 13496-505.
Manolios et al. Science 1990;249:27 4-7.
Merrifield et al. Biochemistry 1982;21 :5020-31.
Mescher et al. Semin Immunol 2007;19:153-61.
Quintana et al. J Clin Invest 2005;115:2149-58.
Samelson et al. J Immunol 1987;139:2708-14.
Sedgwick et al. J Immunol Methods 1989;121 :185-96.
Sigalov A.B. Adv Exp Med Biol 2007;601 :335-44.

(Continued)

*Primary Examiner* — Marcela M Cordero Garcia
*Assistant Examiner* — Jia-Hai Lee
(74) *Attorney, Agent, or Firm* — Medlen & Carroll, LLP

(57) ABSTRACT

The present invention provides compositions comprising peptides derived from amino acid sequences (or from combinations thereof) of fusion and other protein regions of various viruses, including but not limited to, severe acute respiratory syndrome coronavirus, herpesvirus saimiri, human herpesvirus 6, Lassa virus, lymphocytic choriomeningitis virus, Mopeia virus, Tacaribe virus, Friend murine leukemia virus; human T lymphotropic virus type 1; herpesvirus ateles; Marburg virus; Sudan Ebola virus; Zaire Ebola virus, and comprising L- and/or D-amino acids and combinations thereof, which affect T cells by acting on the T cell antigen receptor (TCR). More specifically, the peptides act on the TCRαβ-CD3δε-CD3γε-ζζ signaling complex. Yet more specifically, the peptides act on the TCRα/CD3δε/ζζ signaling module of TCR. The present invention further relates to the prevention and therapy of various T cell-related disease states involving the use of these compositions. Specifically, the compositions are useful in the treatment and/or prevention of a disease or condition where T cells are involved or recruited. The compositions of the present invention also are useful in the production of medical devices comprising peptide matrices (for example, medical implants and implantable devices).

11 Claims, 15 Drawing Sheets

Specification includes a Sequence Listing.

(56) References Cited

OTHER PUBLICATIONS

Sigalov A.B. Adv Exp Med Biol 2008;640:268-311.
Sigalov A.B. PLoS Pathog 2009;5: e1000404.
Sigalov, A.B. Semin. Immunol. 2005;17:51-64.
Sigalov, A.B. Trends Pharmacol Sci 2006;27:518-24.
Sigalov, A.B. Adv Exp Med Biol 2008;640:121-63.
Sigalov, A.B. ed, Multichain Immune Recognition Receptor Signaling: From Spatiotemporal Organization to Human Disease, Springer-Verlag, New York, 2008.
Sigalov, A.B. Faseb J 2007;21 :1633-34; author reply 1635.
Sigalov, A.B. Trends Immunol 2004;25:583-9.
Srinivasan et al. Cytokine. 2009;46:147-59.
Su et al. A synthetic method for peptide-PEG-lipid conjugates: Application of Octreotide-PEG-DSPE synthesis. Bioorganic & Medicinal Chemistry Letters 18 (2008) 4593-4596.
Tugyi et al. Partial D-amino acid substitution: Improved enzymatic stability and preserved Ab recognition of a MUC2 epitope peptide. Proc Natl Acad Sci U SA. Jan. 11, 2005;102(2):413-8.
Wang et al. Cell Immunol 2002;215:12-19.
Wang et al. Clin Immunol 2002; 105: 199-207.
Wedagedera et al. Biophys J 2006;91 :1604-18.
Whittaker et al. Pept Res 1993; 6:125-8.

\* cited by examiner

Similarities in the charge distribution patterns of different immunomodulatory viral sequences

SEQ ID NOS:

| | | | |
|---|---|---|---|
| 78 | TCRα TMD | VIGFRILLLKVAGFNLLMTL | |
| 76 | *TCRα CP* | GLRILLLKV | I |
| 6 | SARS-CoV FP | MYKTPTLKYFGGFNFSQIL | |
| | | | |
| 7 | HVS Tip$^{211-228}$ | ANERNIVKDLKRLENKIN | |
| 28 | HVA Tio$^{225-242}$ | ATDGQLNHRVEKVEKKLT | II |
| 26 | HTLV-1 gp21$^{313-353}$ | AVPVAVWLVSALAMGAGVAGGITGSMSLASGKSLLHEVDKD | |
| | | | |
| 77 | *HIV gp41 FP* | AVGIGALFLGFLGAAGSTMGARSMTLTVQARQL | |
| 8 | LASV FP (gp2$^{260-298}$) | GTFTWTLSDSEGKDTPGGYCLTRWMLIEAELKCFGNTAV | |
| 41 | LCMV FP (gp2$^{266-304}$) | GTFTWTLSDSSGVENPGGYCLTKWMILAAELKCFGNTAV | |
| 43 | MOPV FP (gp2$^{258-296}$) | GLFTWTLSDSEGNDMPGGYCLTRSMLIGLDLKCFGNTAI | |
| 45 | TACV FP (gp2$^{262-300}$) | AFFSWSLTDPLGNEAPGGYCLEKWMLVASELKCFGNTAI | III |
| 47 | CKS-17 | LQNRRGLDLLFLKEGGL | |
| 48 | SEBOV gp2$^{584-600}$ | ILNRKAIDFLLRRWGGT | |
| 49 | ZEBOV gp2$^{584-600}$ | ILNRKAIDFLLQRWGGT | |
| 50 | MARV gp2$^{585-601}$ | LINRHAIDFLLTRWGGT | |
| 47 | Fr-MLV Env gp$^{548-564}$ | LQNRRGLDLLFLKEGGL | |
| 51 | HHV-6 U24$^{28-60}$ | VINDTSFVECIPPPQSRPAWNLWNNRRKTFSFL | |

FIG. 5

Combinatorial TCR peptide inhibitor sequences

|          | A   | B   | C   | D   | E   | F   |     |
| -------- | --- | --- | --- | --- | --- | --- | --- |
| CLASS I  |     |     |     |     |     |     |     |
| CLASS II | A*  | B*  | C*  | D*  | E*  | F*  | G*  |
| CLASS III| A** | B** | C** | D** | E** | F** |     |

COMBINATORIAL SEQUENCES $$R_1 \left[ Arg \right]_{n=0-4} \left[ Lys \right]_{n=0-4} \left[ \begin{array}{c} A \\ A^* \\ A^{**} \end{array} \right] \left[ \begin{array}{c} B \\ B^* \\ B^{**} \end{array} \right] \left[ \begin{array}{c} C \\ C^* \\ C^{**} \end{array} \right] \left[ \begin{array}{c} D \\ D^* \\ D^{**} \end{array} \right] \left[ \begin{array}{c} E \\ E^* \\ E^{**} \end{array} \right] \left[ \begin{array}{c} F \\ F^* \\ F^{**} \end{array} \right] \left[ G^* \right] \left[ Arg \right]_{n=0-4} \left[ Lys \right]_{n=0-4} R_2$$

N-terminus

```
                         SEQUENCE LISTING

<160> NUMBER OF SEQ ID NOS: 99

<210> SEQ ID NO 1
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(3)
<223> OTHER INFORMATION: Xaa is R, K or H
<220> FEATURE:
<221> NAME/KEY: misc_feature
<222> LOCATION: (4)..(7)
<223> OTHER INFORMATION: Xaa is L, I, T or P
<220> FEATURE:
<221> NAME/KEY: misc_feature
<222> LOCATION: (8)..(8)
<223> OTHER INFORMATION: Xaa is R, K or H
<220> FEATURE:
<221> NAME/KEY: misc_feature
<222> LOCATION: (9)..(9)
<223> OTHER INFORMATION: Xaa is V or Y
<220> FEATURE:
<221> NAME/KEY: misc_feature
<222> LOCATION: (10)..(10)
<223> OTHER INFORMATION: Xaa is A or F or nothing
<220> FEATURE:
<221> NAME/KEY: misc_feature
<222> LOCATION: (11)..(11)
<223> OTHER INFORMATION: Xaa is G or nothing

<400> SEQUENCE: 1

Gly Tyr Xaa Xaa Xaa Xaa Xaa Xaa Xaa Xaa Xaa
1               5                   10

<210> SEQ ID NO 2
<211> LENGTH: 15
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa is R, G, I, L or nothing
<220> FEATURE:
<221> NAME/KEY: misc_feature
<222> LOCATION: (2)..(2)
<223> OTHER INFORMATION: Xaa is N, Q, A or nothing
<220> FEATURE:
<221> NAME/KEY: misc_feature
<222> LOCATION: (3)..(3)
<223> OTHER INFORMATION: Xaa is L, I, S or nothing
<220> FEATURE:
<221> NAME/KEY: misc_feature
<222> LOCATION: (4)..(4)
```

```
<223> OTHER INFORMATION: Xaa is V, N, G or nothing
<220> FEATURE:
<221> NAME/KEY: misc_feature
<222> LOCATION: (5)..(5)
<223> OTHER INFORMATION: Xaa is R, K or H
<220> FEATURE:
<221> NAME/KEY: misc_feature
<222> LOCATION: (6)..(6)
<223> OTHER INFORMATION: Xaa is D, R, S or nothing
<220> FEATURE:
<221> NAME/KEY: misc_feature
<222> LOCATION: (8)..(8)
<223> OTHER INFORMATION: Xaa is K, E, L or nothing
<220> FEATURE:
<221> NAME/KEY: misc_feature
<222> LOCATION: (9)..(9)
<223> OTHER INFORMATION: Xaa is R, K or H
<220> FEATURE:
<221> NAME/KEY: misc_feature
<222> LOCATION: (10)..(10)
<223> OTHER INFORMATION: Xaa is L, V, E or nothing
<220> FEATURE:
<221> NAME/KEY: misc_feature
<222> LOCATION: (12)..(12)
<223> OTHER INFORMATION: Xaa is N, K, D or nothing
<220> FEATURE:
<221> NAME/KEY: misc_feature
<222> LOCATION: (13)..(13)
<223> OTHER INFORMATION: Xaa is R, K or H
<220> FEATURE:
<221> NAME/KEY: misc_feature
<222> LOCATION: (14)..(14)
<223> OTHER INFORMATION: Xaa is I, L, D or nothing
<220> FEATURE:
<221> NAME/KEY: misc_feature
<222> LOCATION: (15)..(15)
<223> OTHER INFORMATION: Xaa is N, T or nothing

<400> SEQUENCE: 2

Xaa Xaa Xaa Xaa Xaa Xaa Leu Xaa Xaa Xaa Glu Xaa Xaa Xaa Xaa
1               5                   10                  15

<210> SEQ ID NO 3
<211> LENGTH: 16
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(3)
<223> OTHER INFORMATION: Xaa is R, K or H
<220> FEATURE:
<221> NAME/KEY: misc_feature
<222> LOCATION: (4)..(4)
<223> OTHER INFORMATION: Xaa is S, R, K, H, P or W
<220> FEATURE:
<221> NAME/KEY: misc_feature
<222> LOCATION: (5)..(5)
<223> OTHER INFORMATION: Xaa is M, G or A
<220> FEATURE:
<221> NAME/KEY: misc_feature
<222> LOCATION: (7)..(7)
<223> OTHER INFORMATION: Xaa is L, I, V, N or D
<220> FEATURE:
<221> NAME/KEY: misc_feature
<222> LOCATION: (8)..(8)
<223> OTHER INFORMATION: Xaa is L, I, F, T, E, A or G
<220> FEATURE:
<221> NAME/KEY: misc_feature
<222> LOCATION: (10)..(10)
<223> OTHER INFORMATION: Xaa is E, Q, D, L, F, N or I
<220> FEATURE:
<221> NAME/KEY: misc_feature
<222> LOCATION: (12)..(12)
<223> OTHER INFORMATION: Xaa is R, K or H
<220> FEATURE:
```

```
<221> NAME/KEY: misc_feature
<222> LOCATION: (13)..(13)
<223> OTHER INFORMATION: Xaa is Q, C, E, W or R
<220> FEATURE:
<221> NAME/KEY: misc_feature
<222> LOCATION: (16)..(16)
<223> OTHER INFORMATION: Xaa is L, I, F, T, N or nothing

<400> SEQUENCE: 3

Leu Asn Xaa Xaa Xaa Leu Xaa Xaa Leu Xaa Leu Xaa Xaa Gly Gly Xaa
1               5                   10                  15

<210> SEQ ID NO 4
<211> LENGTH: 17
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(4)
<223> OTHER INFORMATION: Xaa is R, K or H
<220> FEATURE:
<221> NAME/KEY: misc_feature
<222> LOCATION: (5)..(5)
<223> OTHER INFORMATION: Xaa is D, R or S
<220> FEATURE:
<221> NAME/KEY: misc_feature
<222> LOCATION: (7)..(7)
<223> OTHER INFORMATION: Xaa is E, K or L
<220> FEATURE:
<221> NAME/KEY: misc_feature
<222> LOCATION: (8)..(8)
<223> OTHER INFORMATION: Xaa is R, K or H
<220> FEATURE:
<221> NAME/KEY: misc_feature
<222> LOCATION: (9)..(9)
<223> OTHER INFORMATION: Xaa is L, I, or T
<220> FEATURE:
<221> NAME/KEY: misc_feature
<222> LOCATION: (10)..(10)
<223> OTHER INFORMATION: Xaa is L, I, or P
<220> FEATURE:
<221> NAME/KEY: misc_feature
<222> LOCATION: (11)..(11)
<223> OTHER INFORMATION: Xaa is L, I, or T
<220> FEATURE:
<221> NAME/KEY: misc_feature
<222> LOCATION: (13)..(13)
<223> OTHER INFORMATION: Xaa is R, K or H
<220> FEATURE:
<221> NAME/KEY: misc_feature
<222> LOCATION: (14)..(14)
<223> OTHER INFORMATION: Xaa is Q, C, E, W or R
<220> FEATURE:
<221> NAME/KEY: misc_feature
<222> LOCATION: (15)..(15)
<223> OTHER INFORMATION: Xaa is K, G, F, L, I or nothing
<220> FEATURE:
<221> NAME/KEY: misc_feature
<222> LOCATION: (16)..(16)
<223> OTHER INFORMATION: Xaa is T, G or nothing
<220> FEATURE:
<221> NAME/KEY: misc_feature
<222> LOCATION: (17)..(17)
<223> OTHER INFORMATION: Xaa is F, L, I, T, N or nothing

<400> SEQUENCE: 4

Leu Gln Asn Xaa Xaa Leu Xaa Xaa Xaa Xaa Xaa Leu Xaa Xaa Xaa Xaa
1               5                   10                  15

Xaa

<210> SEQ ID NO 5
<211> LENGTH: 17
```

```
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(4)
<223> OTHER INFORMATION: Xaa is R, K or H
<220> FEATURE:
<221> NAME/KEY: misc_feature
<222> LOCATION: (5)..(5)
<223> OTHER INFORMATION: Xaa is L, I, or T
<220> FEATURE:
<221> NAME/KEY: misc_feature
<222> LOCATION: (6)..(6)
<223> OTHER INFORMATION: Xaa is L, I, or P
<220> FEATURE:
<221> NAME/KEY: misc_feature
<222> LOCATION: (7)..(7)
<223> OTHER INFORMATION: Xaa is L, I, or T
<220> FEATURE:
<221> NAME/KEY: misc_feature
<222> LOCATION: (9)..(9)
<223> OTHER INFORMATION: Xaa is R, K or H
<220> FEATURE:
<221> NAME/KEY: misc_feature
<222> LOCATION: (10)..(10)
<223> OTHER INFORMATION: Xaa is D, R or S
<220> FEATURE:
<221> NAME/KEY: misc_feature
<222> LOCATION: (12)..(12)
<223> OTHER INFORMATION: Xaa is E, K or L
<220> FEATURE:
<221> NAME/KEY: misc_feature
<222> LOCATION: (13)..(13)
<223> OTHER INFORMATION: Xaa is R, K or H
<220> FEATURE:
<221> NAME/KEY: misc_feature
<222> LOCATION: (14)..(14)
<223> OTHER INFORMATION: Xaa is Q, C, E, W or R
<220> FEATURE:
<221> NAME/KEY: misc_feature
<222> LOCATION: (15)..(15)
<223> OTHER INFORMATION: Xaa is K, G, F, L, I or nothing
<220> FEATURE:
<221> NAME/KEY: misc_feature
<222> LOCATION: (16)..(16)
<223> OTHER INFORMATION: Xaa is T, G or nothing
<220> FEATURE:
<221> NAME/KEY: misc_feature
<222> LOCATION: (17)..(17)
<223> OTHER INFORMATION: Xaa is F, L, I, T, N or nothing

<400> SEQUENCE: 5

Leu Gln Asn Xaa Xaa Xaa Xaa Leu Xaa Xaa Leu Xaa Xaa Xaa Xaa Xaa
1               5                   10                  15

Xaa

<210> SEQ ID NO 6
<211> LENGTH: 19
<212> TYPE: PRT
<213> ORGANISM: Artificial Sequence
<220> FEATURE:
<223> OTHER INFORMATION: Synthetic

<400> SEQUENCE: 6

Met Tyr Lys Thr Pro Thr Leu Lys Tyr Phe Gly Gly Phe Asn Phe Ser
1               5                   10                  15

Gln Ile Leu

<210> SEQ ID NO 7
<211> LENGTH: 18
<212> TYPE: PRT
```

```
<213> ORGANISM: Artificial Sequence
<220> FEATURE:
<223> OTHER INFORMATION: Synthetic

<400> SEQUENCE: 7

Ala Asn Glu Arg Asn Ile Val Lys Asp Leu Lys Arg Leu Glu Asn Lys
1               5                   10                  15

Ile Asn

<210> SEQ ID NO 8
<211> LENGTH: 39
<212> TYPE: PRT
<213> ORGANISM: Artificial Sequence
<220> FEATURE:
<223> OTHER INFORMATION: Synthetic

<400> SEQUENCE: 8

Gly Thr Phe Thr Trp Thr Leu Ser Asp Ser Glu Lys Asp Thr Pro
1               5                   10                  15

Gly Gly Tyr Cys Leu Thr Arg Trp Met Leu Ile Glu Ala Glu Leu Lys
                20                  25                  30

Cys Phe Gly Asn Thr Ala Val
        35

<210> SEQ ID NO 9
<211> LENGTH: 16
<212> TYPE: PRT
<213> ORGANISM: Artificial Sequence
<220> FEATURE:
<223> OTHER INFORMATION: Synthetic

<400> SEQUENCE: 9

Leu Gln Asn Arg Asp Leu Lys Arg Leu Leu Phe Leu Lys Arg Lys Thr
1               5                   10                  15

<210> SEQ ID NO 10
<211> LENGTH: 11
<212> TYPE: PRT
<213> ORGANISM: Artificial Sequence
<220> FEATURE:
<223> OTHER INFORMATION: Synthetic

<400> SEQUENCE: 10

Met Tyr Lys Thr Pro Thr Leu Lys Tyr Phe Gly
1               5                   10

<210> SEQ ID NO 11
<211> LENGTH: 11
<212> TYPE: PRT
<213> ORGANISM: Artificial Sequence
<220> FEATURE:
<223> OTHER INFORMATION: Synthetic

<400> SEQUENCE: 11

Met Tyr Lys Ile Pro Thr Leu Lys Tyr Phe Gly
1               5                   10

<210> SEQ ID NO 12
<211> LENGTH: 11
<212> TYPE: PRT
<213> ORGANISM: Artificial Sequence
<220> FEATURE:
<223> OTHER INFORMATION: Synthetic

<400> SEQUENCE: 12
```

```
Met Tyr Lys Ile Leu Thr Leu Lys Tyr Phe Gly
1               5                   10

<210> SEQ ID NO 13
<211> LENGTH: 11
<212> TYPE: PRT
<213> ORGANISM: Artificial Sequence
<220> FEATURE:
<223> OTHER INFORMATION: Synthetic

<400> SEQUENCE: 13

Gly Tyr Lys Ile Leu Thr Leu Lys Tyr Phe Gly
1               5                   10

<210> SEQ ID NO 14
<211> LENGTH: 11
<212> TYPE: PRT
<213> ORGANISM: Artificial Sequence
<220> FEATURE:
<223> OTHER INFORMATION: Synthetic

<400> SEQUENCE: 14

Gly Tyr Arg Thr Pro Thr Leu Lys Val Phe Gly
1               5                   10

<210> SEQ ID NO 15
<211> LENGTH: 11
<212> TYPE: PRT
<213> ORGANISM: Artificial Sequence
<220> FEATURE:
<223> OTHER INFORMATION: Synthetic

<400> SEQUENCE: 15

Gly Phe Arg Ile Pro Leu Leu Lys Tyr Phe Gly
1               5                   10

<210> SEQ ID NO 16
<211> LENGTH: 22
<212> TYPE: PRT
<213> ORGANISM: Artificial Sequence
<220> FEATURE:
<223> OTHER INFORMATION: Synthetic

<400> SEQUENCE: 16

Gly Phe Arg Ile Pro Leu Leu Lys Tyr Phe Gly Gly Phe Arg Ile Pro
1               5                   10                  15

Leu Leu Lys Tyr Phe Gly
            20

<210> SEQ ID NO 17
<211> LENGTH: 19
<212> TYPE: PRT
<213> ORGANISM: Artificial Sequence
<220> FEATURE:
<223> OTHER INFORMATION: Synthetic

<400> SEQUENCE: 17

Gly Tyr Arg Thr Pro Thr Leu Lys Val Phe Gly Gly Phe Asn Phe Ser
1               5                   10                  15

Gln Ile Leu

<210> SEQ ID NO 18
<211> LENGTH: 38
<212> TYPE: PRT
<213> ORGANISM: Artificial Sequence
<220> FEATURE:
```

<223> OTHER INFORMATION: Synthetic

<400> SEQUENCE: 18

Gly Tyr Arg Thr Pro Thr Leu Lys Val Phe Gly Gly Phe Asn Phe Ser
1               5                   10                  15
Gln Ile Leu Gly Tyr Arg Thr Pro Thr Leu Lys Val Phe Gly Gly Phe
            20                  25                  30
Asn Phe Ser Gln Ile Leu
            35

<210> SEQ ID NO 19
<211> LENGTH: 40
<212> TYPE: PRT
<213> ORGANISM: Artificial Sequence
<220> FEATURE:
<223> OTHER INFORMATION: Synthetic

<400> SEQUENCE: 19

Cys Gly Tyr Arg Thr Pro Thr Leu Lys Val Phe Gly Gly Phe Asn Phe
1               5                   10                  15
Ser Gln Ile Leu Cys Gly Tyr Arg Thr Pro Thr Leu Lys Val Phe Gly
            20                  25                  30
Gly Phe Asn Phe Ser Gln Ile Leu
            35                  40

<210> SEQ ID NO 20
<211> LENGTH: 42
<212> TYPE: PRT
<213> ORGANISM: Artificial Sequence
<220> FEATURE:
<223> OTHER INFORMATION: Synthetic

<400> SEQUENCE: 20

Cys Gly Tyr Arg Thr Pro Thr Leu Lys Val Phe Gly Gly Phe Asn Phe
1               5                   10                  15
Ser Gln Ile Leu Cys Cys Gly Tyr Arg Thr Pro Thr Leu Lys Val Phe
            20                  25                  30
Gly Gly Phe Asn Phe Ser Gln Ile Leu Cys
            35                  40

<210> SEQ ID NO 21
<211> LENGTH: 19
<212> TYPE: PRT
<213> ORGANISM: Artificial Sequence
<220> FEATURE:
<223> OTHER INFORMATION: Synthetic

<400> SEQUENCE: 21

Gly Tyr Lys Thr Pro Thr Leu Lys Tyr Phe Gly Gly Phe Asn Phe Ser
1               5                   10                  15
Gln Ile Leu

<210> SEQ ID NO 22
<211> LENGTH: 25
<212> TYPE: PRT
<213> ORGANISM: Artificial Sequence
<220> FEATURE:
<223> OTHER INFORMATION: Synthetic

<400> SEQUENCE: 22

Lys Lys Lys Arg Gly Tyr Lys Thr Pro Thr Leu Lys Tyr Phe Gly Gly
1               5                   10                  15

```
Phe Asn Phe Ser Gln Ile Leu Lys Arg
            20                  25
```

<210> SEQ ID NO 23
<211> LENGTH: 50
<212> TYPE: PRT
<213> ORGANISM: Artificial Sequence
<220> FEATURE:
<223> OTHER INFORMATION: Synthetic

<400> SEQUENCE: 23

```
Lys Lys Lys Arg Gly Tyr Lys Thr Pro Thr Leu Lys Tyr Phe Gly Gly
1               5                   10                  15

Phe Asn Phe Ser Gln Ile Leu Lys Arg Lys Lys Lys Arg Gly Tyr Lys
            20                  25                  30

Thr Pro Thr Leu Lys Tyr Phe Gly Gly Phe Asn Phe Ser Gln Ile Leu
        35                  40                  45

Lys Arg
    50
```

<210> SEQ ID NO 24
<211> LENGTH: 16
<212> TYPE: PRT
<213> ORGANISM: Artificial Sequence
<220> FEATURE:
<223> OTHER INFORMATION: Synthetic

<400> SEQUENCE: 24

```
Lys Lys Arg Gly Tyr Lys Thr Pro Thr Leu Lys Val Phe Gly Lys Arg
1               5                   10                  15
```

<210> SEQ ID NO 25
<211> LENGTH: 32
<212> TYPE: PRT
<213> ORGANISM: Artificial Sequence
<220> FEATURE:
<223> OTHER INFORMATION: Synthetic

<400> SEQUENCE: 25

```
Lys Lys Arg Gly Tyr Lys Thr Pro Thr Leu Lys Val Phe Gly Lys Arg
1               5                   10                  15

Lys Lys Arg Gly Tyr Lys Thr Pro Thr Leu Lys Val Phe Gly Lys Arg
            20                  25                  30
```

<210> SEQ ID NO 26
<211> LENGTH: 41
<212> TYPE: PRT
<213> ORGANISM: Artificial Sequence
<220> FEATURE:
<223> OTHER INFORMATION: Synthetic

<400> SEQUENCE: 26

```
Ala Val Pro Val Ala Val Trp Leu Val Ser Ala Leu Ala Met Gly Ala
1               5                   10                  15

Gly Val Ala Gly Gly Ile Thr Gly Ser Met Ser Leu Ala Ser Gly Lys
            20                  25                  30

Ser Leu Leu His Glu Val Asp Lys Asp
        35                  40
```

<210> SEQ ID NO 27
<211> LENGTH: 14
<212> TYPE: PRT
<213> ORGANISM: Artificial Sequence
<220> FEATURE:

```
<223> OTHER INFORMATION: Synthetic

<400> SEQUENCE: 27

Leu Ala Ser Gly Lys Ser Leu Leu His Glu Val Asp Lys Asp
1               5                   10

<210> SEQ ID NO 28
<211> LENGTH: 18
<212> TYPE: PRT
<213> ORGANISM: Artificial Sequence
<220> FEATURE:
<223> OTHER INFORMATION: Synthetic

<400> SEQUENCE: 28

Ala Thr Asp Gly Gln Leu Asn His Arg Val Glu Lys Val Glu Lys Lys
1               5                   10                  15

Leu Thr

<210> SEQ ID NO 29
<211> LENGTH: 13
<212> TYPE: PRT
<213> ORGANISM: Artificial Sequence
<220> FEATURE:
<223> OTHER INFORMATION: Synthetic

<400> SEQUENCE: 29

Leu Asn His Arg Val Glu Lys Val Glu Lys Lys Leu Thr
1               5                   10

<210> SEQ ID NO 30
<211> LENGTH: 13
<212> TYPE: PRT
<213> ORGANISM: Artificial Sequence
<220> FEATURE:
<223> OTHER INFORMATION: Synthetic

<400> SEQUENCE: 30

Ile Val Lys Asp Leu Lys Arg Leu Glu Asn Lys Ile Asn
1               5                   10

<210> SEQ ID NO 31
<211> LENGTH: 14
<212> TYPE: PRT
<213> ORGANISM: Artificial Sequence
<220> FEATURE:
<223> OTHER INFORMATION: Synthetic

<400> SEQUENCE: 31

Leu Ala Ser Gly Lys Ser Leu Leu His Val Glu Lys Lys Asp
1               5                   10

<210> SEQ ID NO 32
<211> LENGTH: 14
<212> TYPE: PRT
<213> ORGANISM: Artificial Sequence
<220> FEATURE:
<223> OTHER INFORMATION: Synthetic

<400> SEQUENCE: 32

Leu Ala Ser Gly Lys Arg Val Glu His Glu Val Asp Lys Asp
1               5                   10

<210> SEQ ID NO 33
<211> LENGTH: 14
<212> TYPE: PRT
<213> ORGANISM: Artificial Sequence
```

<220> FEATURE:
<223> OTHER INFORMATION: Synthetic

<400> SEQUENCE: 33

Leu Ala Ser Gly Lys Asp Leu Lys His Val Glu Lys Lys Asp
1               5                   10

<210> SEQ ID NO 34
<211> LENGTH: 14
<212> TYPE: PRT
<213> ORGANISM: Artificial Sequence
<220> FEATURE:
<223> OTHER INFORMATION: Synthetic

<400> SEQUENCE: 34

Leu Ala Ser Gly Lys Ser Leu Leu His Leu Glu Asn Lys Asp
1               5                   10

<210> SEQ ID NO 35
<211> LENGTH: 18
<212> TYPE: PRT
<213> ORGANISM: Artificial Sequence
<220> FEATURE:
<223> OTHER INFORMATION: Synthetic

<400> SEQUENCE: 35

Ala Thr Asp Gly Gln Leu Asn His Arg Val Glu Lys Leu Glu Asn Lys
1               5                   10                  15

Leu Thr

<210> SEQ ID NO 36
<211> LENGTH: 18
<212> TYPE: PRT
<213> ORGANISM: Artificial Sequence
<220> FEATURE:
<223> OTHER INFORMATION: Synthetic

<400> SEQUENCE: 36

Ala Asn Glu Arg Asn Ile Val Lys Arg Val Glu Arg Leu Glu Asn Lys
1               5                   10                  15

Ile Asn

<210> SEQ ID NO 37
<211> LENGTH: 18
<212> TYPE: PRT
<213> ORGANISM: Artificial Sequence
<220> FEATURE:
<223> OTHER INFORMATION: Synthetic

<400> SEQUENCE: 37

Lys Lys Arg Leu Asn His Arg Val Glu Lys Leu Glu Asn Lys Leu Thr
1               5                   10                  15

Lys Arg

<210> SEQ ID NO 38
<211> LENGTH: 15
<212> TYPE: PRT
<213> ORGANISM: Artificial Sequence
<220> FEATURE:
<223> OTHER INFORMATION: Synthetic

<400> SEQUENCE: 38

Arg Asn Ile Val Lys Arg Val Glu Lys Val Glu Lys Lys Leu Thr
1               5                   10                  15

<210> SEQ ID NO 39
<211> LENGTH: 30
<212> TYPE: PRT
<213> ORGANISM: Artificial Sequence
<220> FEATURE:
<223> OTHER INFORMATION: Synthetic

<400> SEQUENCE: 39

Arg Asn Ile Val Lys Arg Val Glu Lys Val Glu Lys Lys Leu Thr Arg
1               5                   10                  15

Asn Ile Val Lys Arg Val Glu Lys Val Glu Lys Lys Leu Thr
            20                  25                  30

<210> SEQ ID NO 40
<211> LENGTH: 15
<212> TYPE: PRT
<213> ORGANISM: Artificial Sequence
<220> FEATURE:
<223> OTHER INFORMATION: Synthetic

<400> SEQUENCE: 40

Leu Thr Arg Trp Met Leu Ile Glu Ala Glu Leu Lys Cys Phe Gly
1               5                   10                  15

<210> SEQ ID NO 41
<211> LENGTH: 39
<212> TYPE: PRT
<213> ORGANISM: Artificial Sequence
<220> FEATURE:
<223> OTHER INFORMATION: Synthetic

<400> SEQUENCE: 41

Gly Thr Phe Thr Trp Thr Leu Ser Asp Ser Ser Gly Val Glu Asn Pro
1               5                   10                  15

Gly Gly Tyr Cys Leu Thr Lys Trp Met Ile Leu Ala Ala Glu Leu Lys
            20                  25                  30

Cys Phe Gly Asn Thr Ala Val
        35

<210> SEQ ID NO 42
<211> LENGTH: 15
<212> TYPE: PRT
<213> ORGANISM: Artificial Sequence
<220> FEATURE:
<223> OTHER INFORMATION: Synthetic

<400> SEQUENCE: 42

Leu Thr Lys Trp Met Ile Leu Ala Ala Glu Leu Lys Cys Phe Gly
1               5                   10                  15

<210> SEQ ID NO 43
<211> LENGTH: 39
<212> TYPE: PRT
<213> ORGANISM: Artificial Sequence
<220> FEATURE:
<223> OTHER INFORMATION: Synthetic

<400> SEQUENCE: 43

Gly Leu Phe Thr Trp Thr Leu Ser Asp Ser Glu Gly Asn Asp Met Pro
1               5                   10                  15

Gly Gly Tyr Cys Leu Thr Arg Ser Met Leu Ile Gly Leu Asp Leu Lys
            20                  25                  30

Cys Phe Gly Asn Thr Ala Ile
        35

<210> SEQ ID NO 44
<211> LENGTH: 15
<212> TYPE: PRT
<213> ORGANISM: Artificial Sequence
<220> FEATURE:
<223> OTHER INFORMATION: Synthetic

<400> SEQUENCE: 44

Leu Thr Arg Ser Met Leu Ile Gly Leu Asp Leu Lys Cys Phe Gly
1               5                   10                  15

<210> SEQ ID NO 45
<211> LENGTH: 39
<212> TYPE: PRT
<213> ORGANISM: Artificial Sequence
<220> FEATURE:
<223> OTHER INFORMATION: Synthetic

<400> SEQUENCE: 45

Ala Phe Phe Ser Trp Ser Leu Thr Asp Pro Leu Gly Asn Glu Ala Pro
1               5                   10                  15

Gly Gly Tyr Cys Leu Glu Lys Trp Met Leu Val Ala Ser Glu Leu Lys
            20                  25                  30

Cys Phe Gly Asn Thr Ala Ile
        35

<210> SEQ ID NO 46
<211> LENGTH: 15
<212> TYPE: PRT
<213> ORGANISM: Artificial Sequence
<220> FEATURE:
<223> OTHER INFORMATION: Synthetic

<400> SEQUENCE: 46

Leu Glu Lys Trp Met Leu Val Ala Ser Glu Leu Lys Cys Phe Gly
1               5                   10                  15

<210> SEQ ID NO 47
<211> LENGTH: 17
<212> TYPE: PRT
<213> ORGANISM: Artificial Sequence
<220> FEATURE:
<223> OTHER INFORMATION: Synthetic

<400> SEQUENCE: 47

Leu Gln Asn Arg Arg Gly Leu Asp Leu Leu Phe Leu Lys Glu Gly Gly
1               5                   10                  15

Leu

<210> SEQ ID NO 48
<211> LENGTH: 17
<212> TYPE: PRT
<213> ORGANISM: Artificial Sequence
<220> FEATURE:
<223> OTHER INFORMATION: Synthetic

<400> SEQUENCE: 48

Ile Leu Asn Arg Lys Ala Ile Asp Phe Leu Leu Arg Arg Trp Gly Gly
1               5                   10                  15

Thr

<210> SEQ ID NO 49
<211> LENGTH: 17

<212> TYPE: PRT
<213> ORGANISM: Artificial Sequence
<220> FEATURE:
<223> OTHER INFORMATION: Synthetic

<400> SEQUENCE: 49

Ile Leu Asn Arg Lys Ala Ile Asp Phe Leu Leu Gln Arg Trp Gly Gly
1               5                   10                  15

Thr

<210> SEQ ID NO 50
<211> LENGTH: 17
<212> TYPE: PRT
<213> ORGANISM: Artificial Sequence
<220> FEATURE:
<223> OTHER INFORMATION: Synthetic

<400> SEQUENCE: 50

Leu Ile Asn Arg His Ala Ile Asp Phe Leu Leu Thr Arg Trp Gly Gly
1               5                   10                  15

Thr

<210> SEQ ID NO 51
<211> LENGTH: 33
<212> TYPE: PRT
<213> ORGANISM: Artificial Sequence
<220> FEATURE:
<223> OTHER INFORMATION: Synthetic

<400> SEQUENCE: 51

Val Ile Asn Asp Thr Ser Phe Val Glu Cys Ile Pro Pro Gln Ser
1               5                   10                  15

Arg Pro Ala Trp Asn Leu Trp Asn Asn Arg Arg Lys Thr Phe Ser Phe
            20                  25                  30

Leu

<210> SEQ ID NO 52
<211> LENGTH: 15
<212> TYPE: PRT
<213> ORGANISM: Artificial Sequence
<220> FEATURE:
<223> OTHER INFORMATION: Synthetic

<400> SEQUENCE: 52

Gln Ser Arg Pro Ala Trp Asn Leu Trp Asn Asn Arg Arg Lys Thr
1               5                   10                  15

<210> SEQ ID NO 53
<211> LENGTH: 22
<212> TYPE: PRT
<213> ORGANISM: Artificial Sequence
<220> FEATURE:
<223> OTHER INFORMATION: Synthetic

<400> SEQUENCE: 53

Gly Tyr Cys Leu Thr Arg Trp Met Leu Ile Glu Ala Glu Leu Lys Cys
1               5                   10                  15

Phe Gly Asn Thr Ala Val
            20

<210> SEQ ID NO 54
<211> LENGTH: 44
<212> TYPE: PRT
<213> ORGANISM: Artificial Sequence

```
<220> FEATURE:
<223> OTHER INFORMATION: Synthetic

<400> SEQUENCE: 54

Gly Tyr Cys Leu Thr Arg Trp Met Leu Ile Glu Ala Glu Leu Lys Cys
1               5                   10                  15

Phe Gly Asn Thr Ala Val Gly Tyr Cys Leu Thr Arg Trp Met Leu Ile
            20                  25                  30

Glu Ala Glu Leu Lys Cys Phe Gly Asn Thr Ala Val
        35                  40

<210> SEQ ID NO 55
<211> LENGTH: 44
<212> TYPE: PRT
<213> ORGANISM: Artificial Sequence
<220> FEATURE:
<223> OTHER INFORMATION: Synthetic

<400> SEQUENCE: 55

Gly Tyr Gly Leu Thr Arg Trp Met Leu Ile Glu Ala Glu Leu Lys Cys
1               5                   10                  15

Phe Gly Asn Thr Ala Val Gly Tyr Gly Leu Thr Arg Trp Met Leu Ile
            20                  25                  30

Glu Ala Glu Leu Lys Cys Phe Gly Asn Thr Ala Val
        35                  40

<210> SEQ ID NO 56
<211> LENGTH: 22
<212> TYPE: PRT
<213> ORGANISM: Artificial Sequence
<220> FEATURE:
<223> OTHER INFORMATION: Synthetic

<400> SEQUENCE: 56

Gly Tyr Cys Leu Thr Arg Trp Met Leu Ile Glu Ala Glu Leu Lys Cys
1               5                   10                  15

Phe Gly Asn Thr Ala Val
            20

<210> SEQ ID NO 57
<211> LENGTH: 27
<212> TYPE: PRT
<213> ORGANISM: Artificial Sequence
<220> FEATURE:
<223> OTHER INFORMATION: Synthetic

<400> SEQUENCE: 57

Lys Lys Arg Gly Tyr Cys Leu Thr Arg Trp Met Leu Ile Glu Ala Glu
1               5                   10                  15

Leu Lys Cys Phe Gly Asn Thr Ala Val Lys Arg
            20                  25

<210> SEQ ID NO 58
<211> LENGTH: 16
<212> TYPE: PRT
<213> ORGANISM: Artificial Sequence
<220> FEATURE:
<223> OTHER INFORMATION: Synthetic

<400> SEQUENCE: 58

Leu Gln Asn Arg Lys Ala Ile Asp Leu Trp Asn Asn Lys Glu Gly Gly
1               5                   10                  15
```

```
<210> SEQ ID NO 59
<211> LENGTH: 32
<212> TYPE: PRT
<213> ORGANISM: Artificial Sequence
<220> FEATURE:
<223> OTHER INFORMATION: Synthetic

<400> SEQUENCE: 59

Leu Gln Asn Arg Lys Ala Ile Asp Leu Trp Asn Asn Lys Glu Gly Gly
1               5                   10                  15

Leu Gln Asn Arg Lys Ala Ile Asp Leu Trp Asn Asn Lys Glu Gly Gly
            20                  25                  30

<210> SEQ ID NO 60
<211> LENGTH: 16
<212> TYPE: PRT
<213> ORGANISM: Artificial Sequence
<220> FEATURE:
<223> OTHER INFORMATION: Synthetic

<400> SEQUENCE: 60

Ile Leu Asn Arg Arg Gly Leu Asp Gly Leu Asp Leu Lys Glu Gly Gly
1               5                   10                  15

<210> SEQ ID NO 61
<211> LENGTH: 32
<212> TYPE: PRT
<213> ORGANISM: Artificial Sequence
<220> FEATURE:
<223> OTHER INFORMATION: Synthetic

<400> SEQUENCE: 61

Ile Leu Asn Arg Arg Gly Leu Asp Gly Leu Asp Leu Lys Glu Gly Gly
1               5                   10                  15

Ile Leu Asn Arg Arg Gly Leu Asp Gly Leu Asp Leu Lys Glu Gly Gly
            20                  25                  30

<210> SEQ ID NO 62
<211> LENGTH: 21
<212> TYPE: PRT
<213> ORGANISM: Artificial Sequence
<220> FEATURE:
<223> OTHER INFORMATION: Synthetic

<400> SEQUENCE: 62

Lys Lys Arg Ile Leu Asn Arg Arg Gly Leu Asp Gly Leu Asp Leu Lys
1               5                   10                  15

Glu Gly Gly Lys Arg
            20

<210> SEQ ID NO 63
<211> LENGTH: 17
<212> TYPE: PRT
<213> ORGANISM: Artificial Sequence
<220> FEATURE:
<223> OTHER INFORMATION: Synthetic

<400> SEQUENCE: 63

Cys Leu Thr Lys Pro Ala Trp Asn Leu Leu Phe Leu Lys Arg Lys Thr
1               5                   10                  15

Phe

<210> SEQ ID NO 64
<211> LENGTH: 32
<212> TYPE: PRT
```

```
<213> ORGANISM: Artificial Sequence
<220> FEATURE:
<223> OTHER INFORMATION: Synthetic

<400> SEQUENCE: 64

Leu Gln Asn Arg Asp Leu Lys Arg Leu Leu Phe Leu Lys Arg Lys Thr
1               5                   10                  15
Leu Gln Asn Arg Asp Leu Lys Arg Leu Leu Phe Leu Lys Arg Lys Thr
            20                  25                  30

<210> SEQ ID NO 65
<211> LENGTH: 20
<212> TYPE: PRT
<213> ORGANISM: Artificial Sequence
<220> FEATURE:
<223> OTHER INFORMATION: Synthetic

<400> SEQUENCE: 65

Lys Lys Leu Gln Asn Arg Asp Leu Lys Arg Leu Leu Phe Leu Lys Arg
1               5                   10                  15
Lys Thr Lys Arg
            20

<210> SEQ ID NO 66
<211> LENGTH: 14
<212> TYPE: PRT
<213> ORGANISM: Artificial Sequence
<220> FEATURE:
<223> OTHER INFORMATION: Synthetic

<400> SEQUENCE: 66

Gly Gln Leu Asn Lys Thr Pro Thr Leu Lys Glu Gly Gly Leu
1               5                   10

<210> SEQ ID NO 67
<211> LENGTH: 17
<212> TYPE: PRT
<213> ORGANISM: Artificial Sequence
<220> FEATURE:
<223> OTHER INFORMATION: Synthetic

<400> SEQUENCE: 67

Gly Tyr Cys Leu Thr Arg Arg Gly Leu Lys Glu Val Asp Lys Glu Gly
1               5                   10                  15
Gly

<210> SEQ ID NO 68
<211> LENGTH: 34
<212> TYPE: PRT
<213> ORGANISM: Artificial Sequence
<220> FEATURE:
<223> OTHER INFORMATION: Synthetic

<400> SEQUENCE: 68

Gly Tyr Cys Leu Thr Arg Arg Gly Leu Lys Glu Val Asp Lys Glu Gly
1               5                   10                  15
Gly Gly Tyr Cys Leu Thr Arg Arg Gly Leu Lys Glu Val Asp Lys Glu
            20                  25                  30
Gly Gly

<210> SEQ ID NO 69
<211> LENGTH: 34
<212> TYPE: PRT
<213> ORGANISM: Artificial Sequence
```

```
<220> FEATURE:
<223> OTHER INFORMATION: Synthetic

<400> SEQUENCE: 69

Gly Tyr Cys Leu Thr Arg Arg Gly Leu Lys Glu Val Asp Lys Glu Gly
1               5                   10                  15

Gly Gly Tyr Cys Leu Thr Arg Arg Gly Leu Lys Glu Val Asp Lys Glu
            20                  25                  30

Gly Gly

<210> SEQ ID NO 70
<211> LENGTH: 17
<212> TYPE: PRT
<213> ORGANISM: Artificial Sequence
<220> FEATURE:
<223> OTHER INFORMATION: Synthetic

<400> SEQUENCE: 70

Gly Tyr Cys Leu Thr Arg Arg Gly Leu Lys Glu Val Asp Lys Glu Gly
1               5                   10                  15

Gly

<210> SEQ ID NO 71
<211> LENGTH: 21
<212> TYPE: PRT
<213> ORGANISM: Artificial Sequence
<220> FEATURE:
<223> OTHER INFORMATION: Synthetic

<400> SEQUENCE: 71

Lys Lys Gly Tyr Cys Leu Thr Arg Arg Gly Leu Lys Glu Val Asp Lys
1               5                   10                  15

Glu Gly Gly Lys Arg
            20

<210> SEQ ID NO 72
<211> LENGTH: 16
<212> TYPE: PRT
<213> ORGANISM: Artificial Sequence
<220> FEATURE:
<223> OTHER INFORMATION: Synthetic

<400> SEQUENCE: 72

Ile Pro Pro Pro Gln Ser Arg Thr Pro Thr Leu Lys Val Phe Gly Gly
1               5                   10                  15

<210> SEQ ID NO 73
<211> LENGTH: 32
<212> TYPE: PRT
<213> ORGANISM: Artificial Sequence
<220> FEATURE:
<223> OTHER INFORMATION: Synthetic

<400> SEQUENCE: 73

Ile Pro Pro Pro Gln Ser Arg Thr Pro Thr Leu Lys Val Phe Gly Gly
1               5                   10                  15

Ile Pro Pro Pro Gln Ser Arg Thr Pro Thr Leu Lys Val Phe Gly Gly
            20                  25                  30

<210> SEQ ID NO 74
<211> LENGTH: 21
<212> TYPE: PRT
<213> ORGANISM: Artificial Sequence
<220> FEATURE:
```

```
<223> OTHER INFORMATION: Synthetic

<400> SEQUENCE: 74

Lys Lys Arg Ile Pro Pro Pro Gln Ser Arg Thr Pro Thr Leu Lys Val
1               5                   10                  15

Phe Gly Gly Lys Arg
            20

<210> SEQ ID NO 75
<211> LENGTH: 19
<212> TYPE: PRT
<213> ORGANISM: Artificial Sequence
<220> FEATURE:
<223> OTHER INFORMATION: Synthetic

<400> SEQUENCE: 75

Met Tyr Ala Thr Pro Thr Leu Ala Tyr Phe Gly Gly Phe Asn Phe Ser
1               5                   10                  15

Gln Ile Leu

<210> SEQ ID NO 76
<211> LENGTH: 9
<212> TYPE: PRT
<213> ORGANISM: Artificial Sequence
<220> FEATURE:
<223> OTHER INFORMATION: Synthetic

<400> SEQUENCE: 76

Gly Leu Arg Ile Leu Leu Leu Lys Val
1               5

<210> SEQ ID NO 77
<211> LENGTH: 33
<212> TYPE: PRT
<213> ORGANISM: Artificial Sequence
<220> FEATURE:
<223> OTHER INFORMATION: Synthetic

<400> SEQUENCE: 77

Ala Val Gly Ile Gly Ala Leu Phe Leu Gly Phe Leu Gly Ala Ala Gly
1               5                   10                  15

Ser Thr Met Gly Ala Arg Ser Met Thr Leu Thr Val Gln Ala Arg Gln
            20                  25                  30

Leu

<210> SEQ ID NO 78
<211> LENGTH: 20
<212> TYPE: PRT
<213> ORGANISM: Artificial Sequence
<220> FEATURE:
<223> OTHER INFORMATION: Synthetic

<400> SEQUENCE: 78

Val Ile Gly Phe Arg Ile Leu Leu Leu Lys Val Ala Gly Phe Asn Leu
1               5                   10                  15

Leu Met Thr Leu
            20

<210> SEQ ID NO 79
<211> LENGTH: 28
<212> TYPE: PRT
<213> ORGANISM: Artificial Sequence
<220> FEATURE:
<223> OTHER INFORMATION: Synthetic
```

<400> SEQUENCE: 79

Leu Ala Ser Gly Lys Asp Leu Lys His Val Glu Lys Lys Asp Leu Ala
1               5                   10                  15
Ser Gly Lys Asp Leu Lys His Val Glu Lys Lys Asp
            20                  25

<210> SEQ ID NO 80
<211> LENGTH: 30
<212> TYPE: PRT
<213> ORGANISM: Artificial Sequence
<220> FEATURE:
<223> OTHER INFORMATION: Synthetic

<400> SEQUENCE: 80

Cys Leu Ala Ser Gly Lys Asp Leu Lys His Val Glu Lys Lys Asp Cys
1               5                   10                  15
Leu Ala Ser Gly Lys Asp Leu Lys His Val Glu Lys Lys Asp
            20                  25                  30

<210> SEQ ID NO 81
<211> LENGTH: 13
<212> TYPE: PRT
<213> ORGANISM: Artificial Sequence
<220> FEATURE:
<223> OTHER INFORMATION: Synthetic

<400> SEQUENCE: 81

Leu Asn His Arg Val Glu Lys Leu Glu Asn Lys Leu Thr
1               5                   10

<210> SEQ ID NO 82
<211> LENGTH: 4
<212> TYPE: PRT
<213> ORGANISM: Artificial Sequence
<220> FEATURE:
<223> OTHER INFORMATION: Synthetic

<400> SEQUENCE: 82

Arg Arg Arg Arg
1

<210> SEQ ID NO 83
<211> LENGTH: 4
<212> TYPE: PRT
<213> ORGANISM: Artificial Sequence
<220> FEATURE:
<223> OTHER INFORMATION: Synthetic

<400> SEQUENCE: 83

Lys Lys Lys Lys
1

<210> SEQ ID NO 84
<211> LENGTH: 23
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is absent or 1-amino-glucose succinate,
      2-aminododecanoate, or myristoylate
<220> FEATURE:
<221> NAME/KEY: MISC_FEATURE
<222> LOCATION: (2)..(2)

```
<223> OTHER INFORMATION: Xaa is absent or D- or L-amino acid Val, Ile,
      Leu, Gly, Met, Tyr, or Phe
<220> FEATURE:
<221> NAME/KEY: MISC_FEATURE
<222> LOCATION: (3)..(3)
<223> OTHER INFORMATION: Xaa is absent or D- or L-amino acid Val, Ile,
      Leu, Gly, Met, Tyr, or Phe
<220> FEATURE:
<221> NAME/KEY: MISC_FEATURE
<222> LOCATION: (4)..(4)
<223> OTHER INFORMATION: Xaa is absent or D- or L-amino acid Val, Ile,
      Leu, Gly, Met, Tyr, or Phe
<220> FEATURE:
<221> NAME/KEY: MISC_FEATURE
<222> LOCATION: (5)..(5)
<223> OTHER INFORMATION: Xaa is absent or D- or L-amino acid Val, Ile,
      Leu, Gly, Met, Tyr, or Phe
<220> FEATURE:
<221> NAME/KEY: MISC_FEATURE
<222> LOCATION: (6)..(6)
<223> OTHER INFORMATION: Xaa is a positively charged D- or L-amino acid
<220> FEATURE:
<221> NAME/KEY: MISC_FEATURE
<222> LOCATION: (7)..(10)
<223> OTHER INFORMATION: Xaa is Thr or hydrophobic D- or L-amino acid,
      including D- or L-cysteine or a D- or L-cysteine homologue
<220> FEATURE:
<221> NAME/KEY: MISC_FEATURE
<222> LOCATION: (11)..(11)
<223> OTHER INFORMATION: Xaa is a positively charged D- or L-amino acid
<220> FEATURE:
<221> NAME/KEY: MISC_FEATURE
<222> LOCATION: (12)..(12)
<223> OTHER INFORMATION: Xaa is Val or Tyr
<220> FEATURE:
<221> NAME/KEY: MISC_FEATURE
<222> LOCATION: (13)..(13)
<223> OTHER INFORMATION: Xaa is D- or L-amino acid Ala, Phe, or Gly
<220> FEATURE:
<221> NAME/KEY: MISC_FEATURE
<222> LOCATION: (14)..(14)
<223> OTHER INFORMATION: Xaa is absent or a D- or L-amino acid Ala, Phe,
      or Gly
<220> FEATURE:
<221> NAME/KEY: MISC_FEATURE
<222> LOCATION: (15)..(22)
<223> OTHER INFORMATION: Xaa is absent or D- or L-amino acid Gly, Phe,
      Asn, Leu, Ile, Met, Thr or Gln
<220> FEATURE:
<221> NAME/KEY: MISC_FEATURE
<222> LOCATION: (23)..(23)
<223> OTHER INFORMATION: Xaa is absent or Gly-Tris-monopalmitate,
      Gly-Tris-dipalmitate or Gly-Tris-tripalmitate

<400> SEQUENCE: 84

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa
            20

<210> SEQ ID NO 85
<211> LENGTH: 21
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is Gly, Tyr, Cys, Val, Leu, Ile, or Met
<220> FEATURE:
<221> NAME/KEY: MISC_FEATURE
<222> LOCATION: (2)..(4)
<223> OTHER INFORMATION: Xaa is absent or Gly, Tyr, Cys, Val, Leu, Ile,
      or Met
<220> FEATURE:
```

```
<221> NAME/KEY: MISC_FEATURE
<222> LOCATION: (5)..(5)
<223> OTHER INFORMATION: Xaa is Arg, His or Lys
<220> FEATURE:
<221> NAME/KEY: MISC_FEATURE
<222> LOCATION: (6)..(9)
<223> OTHER INFORMATION: Xaa is Leu, Ile, Thr, or Pro
<220> FEATURE:
<221> NAME/KEY: MISC_FEATURE
<222> LOCATION: (10)..(10)
<223> OTHER INFORMATION: Xaa is Arg, His or Lys
<220> FEATURE:
<221> NAME/KEY: MISC_FEATURE
<222> LOCATION: (11)..(13)
<223> OTHER INFORMATION: Xaa is Val, Tyr, Ala, Phe, or Gly
<220> FEATURE:
<221> NAME/KEY: MISC_FEATURE
<222> LOCATION: (14)..(21)
<223> OTHER INFORMATION: Xaa is Gly, Phe, Asn, Leu, Ile, Met, Thr or Gln

<400> SEQUENCE: 85

Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa
            20

<210> SEQ ID NO 86
<211> LENGTH: 31
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is absent; or Gly-Tris-monopalmitate,
      Gly-Tris-dipalmitate or Gly-Tris-tripalmitate; or a conjugated
      sugar selected from the group including 1-amino-glucose succinate,
      2-aminododecanoate, or myristoylate
<220> FEATURE:
<221> NAME/KEY: MISC_FEATURE
<222> LOCATION: (2)..(5)
<223> OTHER INFORMATION: Xaa is absent or Arg or Lys
<220> FEATURE:
<221> NAME/KEY: MISC_FEATURE
<222> LOCATION: (6)..(9)
<223> OTHER INFORMATION: Xaa is absent or Val, Ile, Leu, Gly, Met, Phe,
      or Tyr
<220> FEATURE:
<221> NAME/KEY: MISC_FEATURE
<222> LOCATION: (10)..(10)
<223> OTHER INFORMATION: Xaa is Arg, Lys, or His
<220> FEATURE:
<221> NAME/KEY: MISC_FEATURE
<222> LOCATION: (11)..(14)
<223> OTHER INFORMATION: Xaa is Leu, Ile, Thr, or Pro
<220> FEATURE:
<221> NAME/KEY: MISC_FEATURE
<222> LOCATION: (15)..(15)
<223> OTHER INFORMATION: Xaa is Arg, His or Lys
<220> FEATURE:
<221> NAME/KEY: MISC_FEATURE
<222> LOCATION: (16)..(16)
<223> OTHER INFORMATION: Xaa is Val or Tyr
<220> FEATURE:
<221> NAME/KEY: MISC_FEATURE
<222> LOCATION: (17)..(18)
<223> OTHER INFORMATION: Xaa is absent or Ala, Phe, or Gly
<220> FEATURE:
<221> NAME/KEY: MISC_FEATURE
<222> LOCATION: (19)..(26)
<223> OTHER INFORMATION: Xaa is absent or Gly, Phe, Asn, Leu, Ile, Met,
      Thr or Gln
<220> FEATURE:
<221> NAME/KEY: MISC_FEATURE
<222> LOCATION: (27)..(30)
```

```
<223> OTHER INFORMATION: Xaa is absent or Arg or Lys
<220> FEATURE:
<221> NAME/KEY: MISC_FEATURE
<222> LOCATION: (31)..(31)
<223> OTHER INFORMATION: Xaa is absent; or Gly-Tris-monopalmitate,
      Gly-Tris-dipalmitate or Gly-Tris-tripalmitate; or a conjugated
      sugar selected from the group including 1-amino-glucose succinate,
      2-aminododecanoate, or myristoylate

<400> SEQUENCE: 86

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

<210> SEQ ID NO 87
<211> LENGTH: 17
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is absent; or 1-amino-glucose succinate,
      2-aminododecanoate, or myristoylate
<220> FEATURE:
<221> NAME/KEY: MISC_FEATURE
<222> LOCATION: (2)..(5)
<223> OTHER INFORMATION: Xaa is absent or D- or L-amino acid Arg, Gly,
      Leu, Ile, Asn, Gln, Ala, Ser, or Val
<220> FEATURE:
<221> NAME/KEY: MISC_FEATURE
<222> LOCATION: (6)..(6)
<223> OTHER INFORMATION: Xaa is a positively charged D- or L-amino acid
<220> FEATURE:
<221> NAME/KEY: MISC_FEATURE
<222> LOCATION: (7)..(9)
<223> OTHER INFORMATION: Xaa is Asp, Leu, Ile, Arg, Lys, Ser, Val, or
      Glu
<220> FEATURE:
<221> NAME/KEY: MISC_FEATURE
<222> LOCATION: (10)..(10)
<223> OTHER INFORMATION: Xaa is a positively charged D- or L-amino acid
<220> FEATURE:
<221> NAME/KEY: MISC_FEATURE
<222> LOCATION: (11)..(13)
<223> OTHER INFORMATION: Xaa is Asp, Asn, Leu, Lys, Ile, Val, or Glu
<220> FEATURE:
<221> NAME/KEY: MISC_FEATURE
<222> LOCATION: (14)..(14)
<223> OTHER INFORMATION: Xaa is a positively charged D- or L-amino acid
<220> FEATURE:
<221> NAME/KEY: MISC_FEATURE
<222> LOCATION: (15)..(15)
<223> OTHER INFORMATION: Xaa is Ile, Leu, Asp, Asn, or Thr
<220> FEATURE:
<221> NAME/KEY: MISC_FEATURE
<222> LOCATION: (16)..(16)
<223> OTHER INFORMATION: Xaa is absent or Ile, Leu, Asp, Asn, or Thr
<220> FEATURE:
<221> NAME/KEY: MISC_FEATURE
<222> LOCATION: (17)..(17)
<223> OTHER INFORMATION: Xaa is absent; or Gly-Tris-monopalmitate,
      Gly-Tris-dipalmitate or Gly-Tris-tripalmitate

<400> SEQUENCE: 87

Xaa Xaa Xaa Xaa Xaa Xaa Xaa Xaa Xaa Xaa Xaa Xaa Xaa Xaa Xaa Xaa
1               5                   10                  15

Xaa

<210> SEQ ID NO 88
<211> LENGTH: 15
```

```
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(4)
<223> OTHER INFORMATION: Xaa is Arg, Gly, Leu, Ile, Asn, Gln, Ala, Ser,
      or Val
<220> FEATURE:
<221> NAME/KEY: MISC_FEATURE
<222> LOCATION: (5)..(5)
<223> OTHER INFORMATION: Xaa is Arg, His or Lys
<220> FEATURE:
<221> NAME/KEY: MISC_FEATURE
<222> LOCATION: (6)..(8)
<223> OTHER INFORMATION: Xaa is Asp, Leu, Ile, Arg, Lys, Ser, Val, or
      Glu
<220> FEATURE:
<221> NAME/KEY: MISC_FEATURE
<222> LOCATION: (9)..(9)
<223> OTHER INFORMATION: Xaa is Arg, His or Lys
<220> FEATURE:
<221> NAME/KEY: MISC_FEATURE
<222> LOCATION: (10)..(12)
<223> OTHER INFORMATION: Xaa is Asp, Asn, Leu, Lys, Ile, Val, or Glu
<220> FEATURE:
<221> NAME/KEY: MISC_FEATURE
<222> LOCATION: (13)..(13)
<223> OTHER INFORMATION: Xaa is Arg, His or Lys
<220> FEATURE:
<221> NAME/KEY: MISC_FEATURE
<222> LOCATION: (14)..(15)
<223> OTHER INFORMATION: Xaa is Ile, Leu, Asp, Asn, or Thr

<400> SEQUENCE: 88

Xaa Xaa Xaa Xaa Xaa Xaa Xaa Xaa Xaa Xaa Xaa Xaa Xaa Xaa Xaa
1               5                   10                  15

<210> SEQ ID NO 89
<211> LENGTH: 25
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is absent; or Gly-Tris-monopalmitate,
      Gly-Tris-dipalmitate or Gly-Tris-tripalmitate; or a conjugated
      sugar selected from the group including 1-amino-glucose succinate,
      2-aminododecanoate, or myristoylate
<220> FEATURE:
<221> NAME/KEY: MISC_FEATURE
<222> LOCATION: (2)..(5)
<223> OTHER INFORMATION: Xaa is absent or Arg or Lys
<220> FEATURE:
<221> NAME/KEY: MISC_FEATURE
<222> LOCATION: (6)..(9)
<223> OTHER INFORMATION: Xaa is absent or D- or L-amino acid Arg, Gly,
      Leu, Ile, Asn, Gln, Ala, Ser, or Val
<220> FEATURE:
<221> NAME/KEY: MISC_FEATURE
<222> LOCATION: (10)..(10)
<223> OTHER INFORMATION: Xaa is Arg, Lys, or His
<220> FEATURE:
<221> NAME/KEY: MISC_FEATURE
<222> LOCATION: (11)..(13)
<223> OTHER INFORMATION: Xaa is Asp, Leu, Ile, Arg, Lys, Ser, Val, or
      Glu
<220> FEATURE:
<221> NAME/KEY: MISC_FEATURE
<222> LOCATION: (14)..(14)
<223> OTHER INFORMATION: Xaa is Arg, Lys, or His
<220> FEATURE:
<221> NAME/KEY: MISC_FEATURE
<222> LOCATION: (15)..(17)
```

```
<223> OTHER INFORMATION: Xaa is Ala, Phe, or Gly
<220> FEATURE:
<221> NAME/KEY: MISC_FEATURE
<222> LOCATION: (18)..(18)
<223> OTHER INFORMATION: Xaa is Arg, Lys, or His
<220> FEATURE:
<221> NAME/KEY: MISC_FEATURE
<222> LOCATION: (19)..(19)
<223> OTHER INFORMATION: Xaa is Ile, Leu, Asp, Asn, or Thr
<220> FEATURE:
<221> NAME/KEY: MISC_FEATURE
<222> LOCATION: (20)..(20)
<223> OTHER INFORMATION: Xaa is absent or Ile, Leu, Asp, Asn, or Thr
<220> FEATURE:
<221> NAME/KEY: MISC_FEATURE
<222> LOCATION: (21)..(24)
<223> OTHER INFORMATION: Xaa is absent or Arg or Lys
<220> FEATURE:
<221> NAME/KEY: MISC_FEATURE
<222> LOCATION: (25)..(25)
<223> OTHER INFORMATION: Xaa is absent; or Gly-Tris-monopalmitate,
      Gly-Tris-dipalmitate or Gly-Tris-tripalmitate; or a conjugated
      sugar selected from the group including 1-amino-glucose succinate,
      2-aminododecanoate, or myristoylate

<400> SEQUENCE: 89

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa
            20                  25

<210> SEQ ID NO 90
<211> LENGTH: 27
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is absent; or 1-amino-glucose succinate,
      2-aminododecanoate, or myristoylate
<220> FEATURE:
<221> NAME/KEY: MISC_FEATURE
<222> LOCATION: (2)..(9)
<223> OTHER INFORMATION: Xaa is absent or D- or L-amino acid Ala, Pro,
      Cys, Thr, Asn, Met, Glu, Ser, Gly, Tyr, Leu, Ile, or Gln
<220> FEATURE:
<221> NAME/KEY: MISC_FEATURE
<222> LOCATION: (10)..(10)
<223> OTHER INFORMATION: Xaa is a positively charged D- or L-amino acid
<220> FEATURE:
<221> NAME/KEY: MISC_FEATURE
<222> LOCATION: (11)..(18)
<223> OTHER INFORMATION: Xaa is Ser, Trp, Arg, Lys, His, Pro, Met, Gly,
      Ala, Thr, Leu, Ile, Val, Asp, Asn, Thr, Glu, Phe, or Gln
<220> FEATURE:
<221> NAME/KEY: MISC_FEATURE
<222> LOCATION: (19)..(19)
<223> OTHER INFORMATION: Xaa is a positively charged D- or L-amino acid
<220> FEATURE:
<221> NAME/KEY: MISC_FEATURE
<222> LOCATION: (20)..(22)
<223> OTHER INFORMATION: Xaa is absent or Gln, Cys, Glu, Trp, Arg, Leu,
      Ile, Phe, Gly, or Lys
<220> FEATURE:
<221> NAME/KEY: MISC_FEATURE
<222> LOCATION: (23)..(26)
<223> OTHER INFORMATION: Xaa is absent or Asn, Leu, Ile, Thr, Phe, or
      Val
<220> FEATURE:
<221> NAME/KEY: MISC_FEATURE
<222> LOCATION: (27)..(27)
<223> OTHER INFORMATION: Xaa is absent; or Gly-Tris-monopalmitate,
      Gly-Tris-dipalmitate or Gly-Tris-tripalmitate
```

<400> SEQUENCE: 90

Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa
            20                  25

<210> SEQ ID NO 91
<211> LENGTH: 25
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(8)
<223> OTHER INFORMATION: Xaa is Ala, Pro, Cys, Thr, Asn, Met, Glu, Ser,
      Gly, Tyr, Leu, Ile, or Gln
<220> FEATURE:
<221> NAME/KEY: MISC_FEATURE
<222> LOCATION: (9)..(9)
<223> OTHER INFORMATION: Xaa is Arg, His or Lys
<220> FEATURE:
<221> NAME/KEY: MISC_FEATURE
<222> LOCATION: (10)..(17)
<223> OTHER INFORMATION: Xaa is Ser, Trp, Arg, Lys, His, Pro, Met, Gly,
      Ala, Thr, Leu, Ile, Val, Asp, Asn, Thr, Glu, Phe, or Gln
<220> FEATURE:
<221> NAME/KEY: MISC_FEATURE
<222> LOCATION: (18)..(18)
<223> OTHER INFORMATION: Xaa is Arg, His or Lys
<220> FEATURE:
<221> NAME/KEY: MISC_FEATURE
<222> LOCATION: (19)..(21)
<223> OTHER INFORMATION: Xaa is Gln, Cys, Glu, Trp, Arg, Leu, Ile, Phe,
      Gly, or Lys
<220> FEATURE:
<221> NAME/KEY: MISC_FEATURE
<222> LOCATION: (22)..(25)
<223> OTHER INFORMATION: Xaa is Asn, Leu, Ile, Thr, Phe, or Val

<400> SEQUENCE: 91

Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa
            20                  25

<210> SEQ ID NO 92
<211> LENGTH: 35
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is absent; or Gly-Tris-monopalmitate,
      Gly-Tris-dipalmitate or Gly-Tris-tripalmitate; or a conjugated
      sugar selected from the group including 1-amino-glucose succinate,
      2-aminododecanoate, or myristoylate
<220> FEATURE:
<221> NAME/KEY: MISC_FEATURE
<222> LOCATION: (2)..(5)
<223> OTHER INFORMATION: Xaa is absent or Arg or Lys
<220> FEATURE:
<221> NAME/KEY: MISC_FEATURE
<222> LOCATION: (6)..(13)
<223> OTHER INFORMATION: Xaa is absent or D- or L-amino acid Ala, Pro,
      Cys, Thr, Asn, Met, Glu, Ser, Gly, Tyr, Leu, Ile, or Gln
<220> FEATURE:
<221> NAME/KEY: MISC_FEATURE
<222> LOCATION: (14)..(14)
<223> OTHER INFORMATION: Xaa is Arg, Lys, or His
<220> FEATURE:

```
<221> NAME/KEY: MISC_FEATURE
<222> LOCATION: (15)..(22)
<223> OTHER INFORMATION: Xaa is Ser, Trp, Arg, Lys, His, Pro, Met, Gly,
      Ala, Thr, Leu, Ile, Val, Asp, Asn, Thr, Glu, Phe, or Gln
<220> FEATURE:
<221> NAME/KEY: MISC_FEATURE
<222> LOCATION: (23)..(23)
<223> OTHER INFORMATION: Xaa is Arg, His or Lys
<220> FEATURE:
<221> NAME/KEY: MISC_FEATURE
<222> LOCATION: (24)..(26)
<223> OTHER INFORMATION: Xaa is absent or Gln, Cys, Glu, Trp, Arg, Leu,
      Ile, Phe, Gly, or Lys
<220> FEATURE:
<221> NAME/KEY: MISC_FEATURE
<222> LOCATION: (27)..(30)
<223> OTHER INFORMATION: Xaa is absent or Asn, Leu, Ile, Thr, Phe, or
      Val
<220> FEATURE:
<221> NAME/KEY: MISC_FEATURE
<222> LOCATION: (31)..(31)
<223> OTHER INFORMATION: Xaa is absent; or Gly-Tris-monopalmitate,
      Gly-Tris-dipalmitate or Gly-Tris-tripalmitate; or a conjugated
      sugar selected from the group including 1-amino-glucose succinate,
      2-aminododecanoate, or myristoylate
<220> FEATURE:
<221> NAME/KEY: MISC_FEATURE
<222> LOCATION: (32)..(35)
<223> OTHER INFORMATION: Xaa is absent or Arg or Lys

<400> SEQUENCE: 92

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa
        35

<210> SEQ ID NO 93
<211> LENGTH: 24
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is absent or 1-amino-glucose succinate,
      2-aminododecanoate, or myristoylate
<220> FEATURE:
<221> NAME/KEY: MISC_FEATURE
<222> LOCATION: (2)..(9)
<223> OTHER INFORMATION: Xaa is absent or Ala, Pro, Cys, Thr, Asn, Met,
      Glu, Ser, Gly, Tyr, Leu, Ile, or Gln
<220> FEATURE:
<221> NAME/KEY: MISC_FEATURE
<222> LOCATION: (10)..(10)
<223> OTHER INFORMATION: Xaa is a positively charged D- or L-amino acid
<220> FEATURE:
<221> NAME/KEY: MISC_FEATURE
<222> LOCATION: (11)..(14)
<223> OTHER INFORMATION: Thr or hydrophobic D- or L-amino acids,
      including D- or L-cysteine or a D- or L-cysteine homologue
<220> FEATURE:
<221> NAME/KEY: MISC_FEATURE
<222> LOCATION: (15)..(15)
<223> OTHER INFORMATION: Xaa is a positively charged D- or L-amino acid
<220> FEATURE:
<221> NAME/KEY: MISC_FEATURE
<222> LOCATION: (16)..(16)
<223> OTHER INFORMATION: Xaa is Thr and 3 hydrophobic D- or L-amino
      acid, including D- or L-cysteine or a D- or L-cysteine homologue
<220> FEATURE:
<221> NAME/KEY: MISC_FEATURE
<222> LOCATION: (17)..(19)
```

-continued

```
<223> OTHER INFORMATION: Xaa is hydrophobic D- or L-amino acid,
      including D- or L-cysteine or a D- or L-cysteine homologue
<220> FEATURE:
<221> NAME/KEY: MISC_FEATURE
<222> LOCATION: (20)..(20)
<223> OTHER INFORMATION: Xaa is a positively charged D- or L-amino acid
<220> FEATURE:
<221> NAME/KEY: MISC_FEATURE
<222> LOCATION: (21)..(21)
<223> OTHER INFORMATION: Xaa is Gln, Cys, Glu, Trp, Arg, Leu, Ile, Phe,
      Gly, and Lys
<220> FEATURE:
<221> NAME/KEY: MISC_FEATURE
<222> LOCATION: (22)..(23)
<223> OTHER INFORMATION: Xaa is absent or Gln, Cys, Glu, Trp, Arg, Leu,
      Ile, Phe, Gly, or Lys
<220> FEATURE:
<221> NAME/KEY: MISC_FEATURE
<222> LOCATION: (24)..(24)
<223> OTHER INFORMATION: Xaa is absent or Gly-Tris-monopalmitate,
      Gly-Tris-dipalmitate or Gly-Tris-tripalmitate

<400> SEQUENCE: 93

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa
            20

<210> SEQ ID NO 94
<211> LENGTH: 20
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is Ala, Pro, Cys, Thr, Asn, Met, Glu, Ser,
      Gly, Tyr, Leu, Ile, or Gln.
<220> FEATURE:
<221> NAME/KEY: MISC_FEATURE
<222> LOCATION: (2)..(8)
<223> OTHER INFORMATION: Xaa is absent or Ala, Pro, Cys, Thr, Asn, Met,
      Glu, Ser, Gly, Tyr, Leu, Ile, or Gln
<220> FEATURE:
<221> NAME/KEY: MISC_FEATURE
<222> LOCATION: (9)..(9)
<223> OTHER INFORMATION: Xaa is Arg, His or Lys
<220> FEATURE:
<221> NAME/KEY: MISC_FEATURE
<222> LOCATION: (10)..(12)
<223> OTHER INFORMATION: Xaa is Asp, Leu, Ile, Arg, Lys, Ser, Val, or
      Glu
<220> FEATURE:
<221> NAME/KEY: MISC_FEATURE
<222> LOCATION: (13)..(13)
<223> OTHER INFORMATION: Xaa is Arg, His or Lys
<220> FEATURE:
<221> NAME/KEY: MISC_FEATURE
<222> LOCATION: (14)..(17)
<223> OTHER INFORMATION: Xaa is Leu, Ile, Thr, or Pro
<220> FEATURE:
<221> NAME/KEY: MISC_FEATURE
<222> LOCATION: (18)..(18)
<223> OTHER INFORMATION: Xaa is Arg, His or Lys
<220> FEATURE:
<221> NAME/KEY: MISC_FEATURE
<222> LOCATION: (19)..(19)
<223> OTHER INFORMATION: Xaa is Gln, Cys, Glu, Trp, Arg, Leu, Ile, Phe,
      Gly, or Lys
<220> FEATURE:
<221> NAME/KEY: MISC_FEATURE
<222> LOCATION: (20)..(21)
<223> OTHER INFORMATION: Xaa is absent or Gln, Cys, Glu, Trp, Arg, Leu,
      Ile, Phe, Gly, and Lys
```

```
<400> SEQUENCE: 94

Xaa Xaa Xaa Xaa Xaa Xaa Xaa Xaa Xaa Xaa Xaa Xaa Xaa Xaa Xaa
1               5                   10                  15

Xaa Xaa Xaa Xaa
            20

<210> SEQ ID NO 95
<211> LENGTH: 31
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is absent; or Gly-Tris-monopalmitate,
      Gly-Tris-dipalmitate or Gly-Tris-tripalmitate; or a conjugated
      sugar selected from the group including 1-amino-glucose succinate,
      2-aminododecanoate, or myristoylate
<220> FEATURE:
<221> NAME/KEY: MISC_FEATURE
<222> LOCATION: (2)..(5)
<223> OTHER INFORMATION: Xaa is absent or Arg or Lys
<220> FEATURE:
<221> NAME/KEY: MISC_FEATURE
<222> LOCATION: (6)..(13)
<223> OTHER INFORMATION: Xaa is absent or D- or L-amino acid Ala, Pro,
      Cys, Thr, Asn, Met, Glu, Ser, Gly, Tyr, Leu, Ile, or Gln
<220> FEATURE:
<221> NAME/KEY: MISC_FEATURE
<222> LOCATION: (14)..(14)
<223> OTHER INFORMATION: Xaa is Arg, Lys, or His
<220> FEATURE:
<221> NAME/KEY: MISC_FEATURE
<222> LOCATION: (15)..(17)
<223> OTHER INFORMATION: Xaa is Asp, Leu, Ile, Arg, Lys, Ser, Val, or
      Glu
<220> FEATURE:
<221> NAME/KEY: MISC_FEATURE
<222> LOCATION: (18)..(18)
<223> OTHER INFORMATION: Xaa is Arg, His or Lys
<220> FEATURE:
<221> NAME/KEY: MISC_FEATURE
<222> LOCATION: (19)..(22)
<223> OTHER INFORMATION: Xaa is Leu, Ile, Thr, or Pro
<220> FEATURE:
<221> NAME/KEY: MISC_FEATURE
<222> LOCATION: (23)..(23)
<223> OTHER INFORMATION: Xaa is Arg, His or Lys
<220> FEATURE:
<221> NAME/KEY: MISC_FEATURE
<222> LOCATION: (24)..(26)
<223> OTHER INFORMATION: Xaa is absent or Gln, Cys, Glu, Trp, Arg, Leu,
      Ile, Phe, Gly, or Lys
<220> FEATURE:
<221> NAME/KEY: MISC_FEATURE
<222> LOCATION: (27)..(30)
<223> OTHER INFORMATION: Xaa is absent or Arg or Lys
<220> FEATURE:
<221> NAME/KEY: MISC_FEATURE
<222> LOCATION: (31)..(31)
<223> OTHER INFORMATION: Xaa is absent; or Gly-Tris-monopalmitate,
      Gly-Tris-dipalmitate or Gly-Tris-tripalmitate; or a conjugated
      sugar selected from the group including 1-amino-glucose succinate,
      2-aminododecanoate, or myristoylate

<400> SEQUENCE: 95

Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
                20                  25                  30

<210> SEQ ID NO 96
```

```
<211> LENGTH: 16
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: A terminal conjugate moiety affects G in this
      position.

<400> SEQUENCE: 96

Gly Arg Lys Leu Gly Tyr Lys Leu Leu Thr Ile Arg Tyr Ala Asn Leu
1               5                   10                  15

<210> SEQ ID NO 97
<211> LENGTH: 17
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: A terminal conjugate moiety affects G in this
      position.

<400> SEQUENCE: 97

Gly Arg Lys Gly Tyr Arg Pro Thr Pro Ile Arg Val Ala Phe Gly Asn
1               5                   10                  15

Leu

<210> SEQ ID NO 98
<211> LENGTH: 23
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: A terminal conjugate moiety affects G in this
      position.

<400> SEQUENCE: 98

Gly Arg Lys Leu Val Leu Gly Lys Ala Ser Val Pro Ala Thr Gly Ser
1               5                   10                  15

Arg Leu Val Ser Lys Tyr Lys
            20

<210> SEQ ID NO 99
<211> LENGTH: 20
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: A terminal conjugate moiety affects G in this
      position.

<400> SEQUENCE: 99

Gly Arg Lys Gly Tyr Leu Gly Pro Gly Lys Asp Leu Ser Arg Val Asn
1               5                   10                  15

Val Lys Gly Arg
            20
```

INHIBITION OF TCR SIGNALING WITH PEPTIDE VARIANTS

CROSS REFERENCE TO RELATED APPLICATIONS

This application claims priority to a U.S. provisional application Ser. No. 61/247,033 entitled INHIBITION OF TCR SIGNALING WITH PEPTIDE VARIANTS, filed on Sep. 30, 2009, which is incorporated in its entirety herein by reference.

FIELD OF THE INVENTION

The present invention relates to peptides or fragments, homologs and derivatives thereof, which are derived from amino acid sequences of fusion and other protein regions of various viruses and from combinations thereof, and affect T cells by action on the activating T cell receptor. The present invention further relates to the treatment or prevention of various inflammatory and autoimmune disease states or other conditions where T cells are involved or recruited. In one embodiment, T cell receptor is inhibited by variant peptides binding to the transmembrane regions of the TCRζ and CD3δε subunits.

BACKGROUND OF THE INVENTION

1. T Cells and T Cell-related Pathologies

Immune cells respond to the presence of foreign antigens with a wide range of responses, including the secretion of preformed and newly formed mediators, phagocytosis of particles, endocytosis, cytotoxicity against target cells, as well as cell proliferation and/or differentiation. T cells are a subgroup of cells which together with other immune cell types (polymorphonuclear, eosinophils, basophils, mast cells, B cells, and NK cells), constitute the cellular component of the immune system (U.S. Pat. No. 6,057,294; US Pat. Appl. 20050070478). Under physiological conditions T cells function in immune surveillance and in the elimination of foreign antigen. However, under pathological conditions there is compelling evidence that T cells play a major role in the causation and propagation of disease. In these disorders, breakdown of T cell immunological tolerance, either central or peripheral is a fundamental process in the causation of autoimmune disease.

Central tolerance involves thymic deletion of self reactive cells (negative selection) and positive selection of T cells with low affinity for self major histocompatibility complex antigens (MHC). In contrast, there are four, non-mutually exclusive hypotheses that have been proposed to explain peripheral T cell tolerance which are involved in the prevention of tissue specific autoimmune disease. These include: anergy (loss of co-stimulatory signals, down regulation of receptors critical for T cell activation), deletion of reactive T cells, ignorance of the antigen by the immune system and suppression of autoreactive T cells. Tolerance once induced does not necessarily persist indefinitely. A breakdown in any of these mechanisms may lead to autoimmune disease (Srinivasan et al. *Cytokine*. 2009; 46:147-59; Mescher et al. *Semin Immunol* 2007; 19:153-61; US Pat. Appl. 20050070478).

Numerous diseases are believed to result from autoimmune mechanisms (Allen et al. *J Pept Res* 2005; 65:591-604; WO 2006077601). A non-exhaustive list of autoimmune disorders include: systemic lupus erythematosus, rheumatoid arthritis, multiple sclerosis, type I diabetes, gastroenterological conditions e.g. inflammatory bowel disease e.g. Crohn's disease, primary biliary cirrhosis, chronic active hepatitis; skin problems e.g. atopic dermatitis, psoriasis, pemphigus vulgaris; cardiovascular problems e.g. autoimmune pericarditis. Autoimmune diseases affect millions of individuals worldwide and the cost of these diseases, in terms of actual treatment expenditures and lost productivity, is measured in billions of dollars annually. Millions of individuals suffer from or are affected by autoimmune diseases. Over 400 000 people in the United States suffer from multiple sclerosis (MS), while diabetes affects about 18.2 million people (6.3% of the population). Of the 18.2 million people with diabetes, 5-10% have type I (juvenile) diabetes. Over 16 000 new cases of lupus are reported every year, with the total number of diagnosed cases ranging between 500 000 and 1.5 million; and 2.1 million people (almost 1% of the American population) are affected by rheumatoid arthritis. Psoriasis affects 4.5 million people, with 23% of those further diagnosed with psoriatic arthritis. Irritable bowel syndrome/inflammatory bowel disease (IBS/IBD) affects approximately 10-20%, or up to one in five people in America. T cells also play a major role in the rejection for organ transplantation or graft versus host disease by bone marrow (hematopoietic stem cell) transplantation. Regulation of such immune responses is therefore therapeutically desired.

2. T Cell Receptor

Autoimmune disease and other T cell-related pathologies are characterised by the recruitment of T cells to sites of inflammation. At these sites, T cells, coupled with their ability to produce and regulate cytokines and influence B cell function, orchestrate the immune response and shape the final clinical outcome.

T cells respond to antigen via a polypeptide complex composed of the ligand-binding T cell receptor (TCR) disulfide-linked α and β subunits (or γ and δ subunits in γδ T cells) that have single transmembrane (TM) spans per subunit and small intracellular tails and associate noncovalently with hetero-(CD3γε and CD3δε) and homodimeric (ζζ) signaling subunits (Cambior J. C. *Curr Opin Immunol* 1992; 4:257-64; A. B. Sigalov, ed, *Multichain Immune Recognition Receptor Signaling: From Spatiotemporal Organization to Human Disease*, Springer-Verlag, New York, 2008). The CD3ε, δ, and γ chains have single Ig-family extracellular domains, single presumably α-helical TM spans, and intrinsically disordered intracellular domains of 40-60 residues, whereas each ζ subunit has a small extracellular region (9 residues) carrying the intersubunit disulfide bond, a single presumably α-helical TM span per subunit, and a large, intrinsically disordered cytoplasmic domain of ~110 residues. An understanding of the process of TCR-mediated TM signal transduction and subsequent T cell activation, leading to T cell proliferation and differentiation, is therefore pivotal to both health and disease. Disturbance in this intricate structure-function relationship of TCR, harmonising antigen recognition with T cell activation may provide the therapeutic means to deal with inflammatory and other T cell-related disorders.

3. Viral Modulation of T Cell Receptor Signaling

To successfully infect, replicate and persist in the host, viruses have evolved numerous strategies to take control of multiple cellular processes including those that target TM signal transduction mediated by immune receptors including TCR (Jerome K. R. *J Virol* 2008; 82:4194-204; Sigalov A. B. *PLoS Pathog* 2009; 5: e1000404; Kim W. M. and Sigalov A. B. *Adv Exp Med Biol* 2008; 640:325-49; Sigalov A. B. *Adv Exp Med Biol* 2008; 640:268-311). Recent breakthroughs in our improved understanding of the TCR-targeted strategies used by the viruses to escape from the host immune surveillance reveal new therapeutic targets for antiviral as well as immunomodulatory therapy (Sigalov A. B. *Adv Exp Med Biol* 2007; 601; 335-44; Sigalov A. B. *PLoS Pathog* 2009; 5: e1000404). Therefore, further investigation of how viruses have adapted to disarm the innate and adaptive immune system will prove invaluable in rational drug design efforts aiming to reduce immune activation or inflammation. In particular, viral T cell evasion strategies can be transferred to therapeutic strategies to treat T cell-mediated diseases that require similar functionalities. Viruses represent years of evolution and the efficiency and optimization that come along with it.

4. Treatment of T Cell-related Pathologies

Traditional reagents and methods used to attempt to regulate an immune response in a patient also result in unwanted side effects and have limited effectiveness (WO 2006077601). For example, immunosuppressive reagents (e.g., cyclosporin A, azathioprine, and prednisone) used to treat patients with autoimmune diseases also suppress the patient's entire immune response, thereby increasing the risk of infection, and can cause toxic side effects to non-lymphoid tissues. Due to the medical importance of immune regulation and the inadequacies of existing immunopharmacological reagents, reagents and methods to regulate specific parts of the immune system have been the subject of study for many years.

Antibodies have been considered as clinically significant therapeutic agents for various T cell-related diseases. Traditional costimulatory blockade using antibodies or fragments of antibodies, while promising, is not without drawbacks. Disadvantages to these approaches include inherent immunogenicity, unwanted Fc signaling, as well as poor tissue penetration. There have also been some indications that immunosuppression can occur with long-term treatment (Allen et al. *J Pept Res* 2005; 65:591-604). The use of antibodies is suggested (U.S. Pat. No. 6,221,352) to treat autoimmune disorders such as rheumatoid arthritis. Specifically, this patent covers the administration of monoclonal antibodies, alone and/or coupled to cytotoxic or cytostatic agents. However, antibody therapy poses serious disadvantages. First, as antibodies are natural products they must be produced in cell lines or other live expression systems. This raises a that there could be contamination of antibody preparations by infectious agents such as prions or viruses. Although tight regulation and regulatory vigilance and surveillance can reduce this concern, the need for ongoing monitoring arid testing for contamination contributes to the high cost of developing and administering antibody therapies. In addition, antibody-based therapies require considerable logistical support. As antibodies are proteins, they cannot be given orally, except for those used to treat certain types of mucosal infectious diseases, and therefore, systemic administration is required. Another serious disadvantage of antibody-based therapies is the high costs of production, storage, and administration. Moreover, long infusions (i.e., for example, an hour or longer) require a hospital environment and are often associated with mild to very severe side effects. For example, (genengnews.com/articles/chitem_print.aspx?aid=1668&chid=2), in one trial, in which four patients in the U.K. were given an anticancer antibody reactive against an important T cell receptor (CD28) severe and life-threatening responses were observed; the cause is at present not understood. This makes large-scale clinical applications of a number of monoclonal antibodies with demonstrated therapeutic activity impossible or, at least, severely compromised. Fast degradation of the administered antibodies is another drawback of antibody-based therapy.

Peptides based on TCR-derived sequences for disrupting TCR function presumably by interfering with assembly have also been disclosed (WO 96/22306; WO 97/47644; US Pat. Appl. 20050070478). Despite multiple advantages of these peptides as compared to antibodies, they have relatively low efficacy in terms of inhibiting TCR, thus having a high potential for toxicity and side effects, while the primary criteria for rational design of these immunomodulatory peptides and optimizing their immunomodulatory activity have not been suggested.

Filoviral immunosuppressive peptides and modified derivatives thereof have been also disclosed (US Pat. Appl. 20070185025). Similarly to the TCR derived peptide sequences, these peptides demonstrate immunosuppressive activity at relatively high peptide doses, thus having a high potential for toxicity and side effects, while the primary criteria for rational design of these immunomodulatory peptides and optimizing their immunomodulatory activity have not been suggested.

Novel uses of peptides derived from the 33 amino acid residues-long HIV gp41 fusion peptide ($FP_{1-33}$) domain, in methods for prevention or treatment of autoimmune and other T cell-mediated pathologies, have also been disclosed (WO 2006077601). The $FP_{1-33}$ peptide was stated to be effective at concentrations about 100 fold lower than the peptides of the invention by Manolios (U.S. Pat. No. 6,057,294; US Pat. Appl. 20050070478). However, published and disclosed experimental data on immunomodulatory activity of this 33 amino acid residues-long peptide and its fragments (Cohen et al. *Biochemistry* 2008; 47:4826-33; Bloch et al. *Faseb J* 2007; 21:393-401; A. B. Sigalov. *Faseb J* 2007; 21:1633-34; author reply 1635; WO 2006077601) are discrepant (A. B. Sigalov. *Faseb J* 2007; 21:1633-34; author reply 1635; WO 2006077601). While full length $FP_{1-33}$ variants have been disclosed as pharmaceutical compositions to treat T cell-mediated pathologies (WO 2006077601), in other publications it has been stated that in contrast to 16 amino acid residue-long N-terminal region ($FP_{1-16}$) of $FP_{1-33}$ and its fragments ($FP_{1-8}$, $FP_{5-13}$, and $FP_{9-16}$), the C-terminal half of $FP_{1-33}$ ($FP_{17-32}$) has been found to be inactive in all assays used (A. B. Sigalov. *Faseb J* 2007; 21:1633-34; author reply 1635).

5. Prior Art

Prior art (U.S. Pat. No. 6,221,352) suggests to use antibodies to target specific TCRs to treat autoimmune disorders such as rheumatoid arthritis. Specifically, this patent covers the administration of monoclonal antibodies, alone and/or coupled to cytotoxic or cytostatic agents. However, antibody therapy poses serious disadvantages. First, as antibodies are natural products they must be produced in cell lines or other live expression systems. This raises a that there could be contamination of antibody preparations by infectious agents such as prions or viruses. Although tight regulation and regulatory vigilance and surveillance can reduce this concern, the need for ongoing monitoring and testing for contamination contributes to the high cost of developing and administering antibody therapies. In addition, antibody-based therapies require considerable logistical support. As antibodies are proteins, they cannot be given orally, except for those used to treat certain types of mucosal infectious diseases, and therefore, systemic administration is required. Another serious disadvantage of antibody-based therapies is the high costs of production, storage, and administration. Moreover, long infusions (i.e., for example, an hour or longer) require a hospital environment and are often associated with mild to very severe side effects. For example (genengnews.com/articles/chitem_print.aspx?aid=1668 & chid=2), in one trial, in which four patients in the U.K. were given an anticancer antibody reactive against an important T cell receptor (CD28) severe and life-threatening responses were observed; the cause is at present not understood. This makes large-scale clinical applications of a number of monoclonal antibodies with demonstrated therapeutic activity impossible or, at least, severely compromised. Fast degradation of the administered antibodies is another drawback of antibody-based therapy.

Another prior art (U.S. Pat. No. 6,057,294; US Pat. Appl. 20050070478) suggests to use TCR-derived peptide sequences to treat autoimmune and other T cell-related disorders. Despite multiple advantages of these peptides as compared to antibodies, they have relatively low efficacy in terms of inhibiting TCR, thus having a high potential for toxicity and side effects, while the primary criteria for rational design of these immunomodulatory peptides and optimizing their immunomodulatory activity have not been suggested.

Yet another prior art (US Pat. Appl. 20070185025) provides uses of filoviral immunosuppressive peptides and modified derivatives thereof to treat T cell-mediated pathologies. Similarly to the TCR-derived peptide sequences, these peptides demonstrate immunosuppressive activity at relatively high peptide doses, thus having a high potential for toxicity and side effects, while the primary criteria for rational design of these immunomodulatory peptides and optimizing their immunomodulatory activity have not been suggested.

Yet another prior art (WO 2006077601) provides novel uses of peptides derived from the HIV gp41 fusion peptide domain, in methods for prevention or treatment of autoimmune and other T cell-mediated pathologies. These peptides were demonstrated to be effective at concentrations about 100 fold lower than the peptides of the invention by Manolios (U.S. Pat. No. 6,057,294; US Pat. Appl. 20050070478). However, the suggested peptide sequences of this invention are based on the only amino acid sequences, the primary sequence of the HIV gp41 fusion peptide domain, which in addition to the lack of the primary criteria for rational design of these immunomodulatory peptides and optimizing their immunomodulatory activity, strongly limits further optimization of efficacy and specificity of targeting and inhibiting TCR by peptide variants.

Yet still another prior art (US Pat. Appl. 20080096809) provides membrane binding diastereomeric peptides comprising amino acid sequences corresponding to a fragment of a transmembrane proteins, wherein at least two amino acid residues of the diastereomeric peptides being in a D-isomer configuration. These peptides are suggested to be useful in inhibiting fusion membrane protein events, including specifically viral replication and transmission. However, these peptides are not designed specifically to treat T cell-related disorders.

What is needed in the art is a broad-based TCR-targeted therapy rationally designed to disrupt protein-protein interactions as specifically and effectively as viruses do that may be administered to treat various diseases having an underlying T cell etiology that is safe and effective.

SUMMARY OF THE INVENTION

Novel aspect of the present invention consists of peptides derived from amino acid sequences of fusion and other protein regions of various viruses, including but not limiting to, severe acute respiratory syndrome coronavirus (SARS-CoV), herpesvirus saimiri (HVS), human herpesvirus 6 (HHV-6), Lassa virus (LASV), lymphocytic choriomeningitis virus (LCMV), Mopeia virus (MOPV), Tacaribe virus (TACV), Friend murine leukemia virus (MLV); human T lymphotropic virus type 1 (HTLV-1,); herpesvirus ateles (HVA); Marburg virus (MARV); Sudan Ebola virus (SEBOV); Zaire Ebola virus (ZEBOV), which target and inhibit T cell receptor (TCR). In addition, in this invention, the criteria of designing these immunomodulatory peptides and a new approach to optimizing their immunomodulatory activity are suggested. Novel uses of these peptides in methods for prevention or treatment of autoimmune and other T cell-mediated pathologies are also suggested.

The peptides and compositions of the present inventions are derived from amino acid sequences of fusion and other protein regions of various viruses, can be designed and formulated to be delivered orally, optimized for their efficacy and specificity in accordance to the suggested critera, thus improving upon prior art and overcoming current limitations in the prior art. It is advantageous to transfer therapeutic strategies that target redundant processes found among a number of viruses. Viruses represent years of evolution and the efficiency and optimization that come along with it.

Peptides and compositions of the present invention can be used commercially as therapeutic agents to treat T cell-related disorders. A non-exhaustive list of disorders in which T cells are involved/recruited include: allergic diathesis e.g. delayed type hypersensitivity, contact dermatitis; autoimmune disease e.g. systemic lupus erythematosus, rheumatoid arthritis, multiple sclerosis, diabetes, Guillain-Barre syndrome, Hashimotos disease, pernicious anaemia; gastroenterological conditions e.g. inflammatory bowel disease, Crohn's disease, primary biliary cirrhosis, chronic active hepatitis; skin problems e.g. atopic dermatitis, psoriasis, pemphigus vulgaris; infective disease; respiratory conditions e.g. allergic alveolitis; cardiovascular problems e.g. autoimmune pericarditis; organ transplantation; inflammatory conditions e.g. myositis, ankylosing spondylitis; any disorder where T cells are involved recruited.

The present invention relates to peptides and compounds, which affect T cells by action on the T cell antigen receptor (TCR). The peptides and compositions of the present invention are derived from amino acid sequences (or from combinations thereof) of fusion and other protein regions of various viruses, including but not limiting to, severe acute respiratory syndrome coronavirus (SARS-CoV), herpesvirus saimiri (HVS), human herpesvirus 6 (HHV-6), Lassa virus (LASV), lymphocytic choriomeningitis virus (LCMV), Mopeia virus (MOPV), Tacaribe virus (TACV), Friend murine leukemia virus (Fr-MLV); human T lymphotropic virus type 1 (HTLV-1); herpesvirus ateles (HVA); Marburg virus (MARV); Sudan Ebola virus (SEBOV); Zaire Ebola virus (ZEBOV), and consisting of L- and/or D-amino acids and combinations thereof. The present invention further relates to the prevention and therapy of various T cell-related disease states involving the use of these peptides and compounds. Specifically, the peptides and compounds are useful in the treatment and/or prevention of a disease or condition where T cells are involved or recruited. The peptides of the present invention also are useful in the production of medical devices comprising peptide matrices (for example, medical implants and implantable devices). In one embodiment, TCR signaling is inhibited by variant peptides binding to the transmembrane regions of the CD3δ, ε and TCR ζ subunits.

In one embodiment, the present invention contemplates a variant SARS-CoV FP sequence-based TCR peptide inhibitor itself or comprising at least one amino acid addition and/or substitution that optimizes binding to CD3δ,ε and TCR ζ subunits relative to the TCR α subunit transmembrane domain (TCRα TMD: V-I-G-F-R-I-L-L-L-K-V-A-G-F-N-L-L-M-T-L) (SEQ ID NO: 78). In one embodiment, the peptide further comprises a C-terminal and/or an N-terminal sugar conjugate. In one embodiment, the sugar conjugate is 1-amino-glucose succinate. In one embodiment, the peptide further comprises a C-terminal and/or an N-terminal lipid conjugate. In one embodiment, the lipid conjugate is selected from the group comprising 2-aminododecanoate or myristoylate. In one embodiment, the lipid conjugate is selected from the group comprising Gly-Tris-monopalmitate, Gly-Tris-dipalmitate, or Gly-Tris-tripalmitate. In one embodiment, the peptide comprises a cyclic peptide. In one embodiment, the peptide comprise a disulfide-linked dimer. In one embodiment, the peptide inhibitor includes amino acids selected from the group including, but not limited to, L-amino acids, or D-amino acids.

In one embodiment, the present invention contemplates a method comprising: a) providing; i) a patient having at least one symptom of a disease or condition where T cells are involved or recruited; and ii) a variant SARS-CoV FP sequence-based TCR peptide inhibitor itself or comprising at least one amino acid addition and or substitution that optimizes binding to CD3δ,ε and TCR ζ subunits relative to the TCRα TMD capable of reducing said T cell activation; b) administering said inhibitor to said patient under conditions such that said at least one symptom is reduced. In one embodiment, the medical condition comprises an autoimmune disorder. In one embodiment, the autoimmune disorder is selected from the group consisting of systemic lupus erythematosus, rheumatoid arthritis, multiple sclerosis, type I diabetes, gastroenterological conditions e.g. inflammatory bowel disease e.g. Crohn's disease, primary biliary cirrhosis, chronic active hepatitis; skin problems e.g. atopic dermatitis, psoriasis, pemphigus vulgaris; cardiovascular problems e.g. autoimmune pericarditis.

In one embodiment, the present invention contemplates a peptide inhibitor comprising an amino acid sequence consisting of G-Y-$X_1$-$X_2$-$X_3$-$X_4$-$X_5$-$X_6$-$X_7$-$X_8$-$X_9$ (SEQ ID NO: 1), wherein $X_1$ and $X_6$ are selected from the group consisting of R, K or H; $X_2$, $X_3$, $X_4$ and $X_5$ are selected from the group consisting of L, I, T or P; $X_7$ is selected from the group consisting of V or Y; $X_8$ consists of A or F or nothing; and $X_9$ consists of G or nothing. In one embodiment, the peptide further comprises a C-terminal and/or an N-terminal sugar conjugate. In one embodiment, the sugar conjugate is 1-amino-glucose succinate. In one embodiment, the peptide further comprises a C-terminal and/or an N-terminal lipid conjugate. In one embodiment, the lipid conjugate is selected from the group comprising 2-aminododecanoate or myristoylate. In one embodiment, the lipid conjugate is selected from the group comprising Gly-Tris-monopalmitate, Gly-Tris-dipalmitate, or Gly-Tris-tripalmitate. In one embodiment, the peptide comprises a cyclic peptide. In one embodiment, the peptide comprise a disulfide-linked dimer. In one embodiment, the peptide inhibitor includes amino acids selected from the group including, but not limited to, L-amino acids, or D-amino acids.

In one embodiment, the present invention contemplates a method comprising: a) providing; i) a patient having at least one symptom of a disease or condition where T cells are involved or recruited; and ii) a peptide inhibitor comprising an amino acid sequence consisting of G-Y-$X_1$-$X_2$-$X_3$-$X_4$-$X_5$-$X_6$-$X_7$-$X_8$-$X_9$ (SEQ ID NO: 1), wherein $X_1$ and $X_6$ are selected from the group consisting of R, K or H; $X_2$, $X_3$, $X_4$ and $X_5$ are selected from the group consisting of L, I, T or P; $X_7$ is selected from the group consisting of V or Y; $X_8$ consists of A or F or nothing; and $X_9$ consists of G or nothing capable of reducing said T cell activation; b) administering said inhibitor to said patient under conditions such that said at least one symptom is reduced. In one embodiment, the medical condition comprises an autoimmune disorder. In one embodiment, the autoimmune disorder is selected from the group consisting of systemic lupus erythematosus, rheumatoid arthritis, multiple sclerosis, type I diabetes, gastroenterological conditions e.g. inflammatory bowel disease e.g. Crohn's disease, primary biliary cirrhosis, chronic active hepatitis; skin problems e.g. atopic dermatitis, psoriasis, pemphigus vulgaris; cardiovascular problems e.g. autoimmune pericarditis.

In one embodiment, the present invention contemplates a variant HTLV-1 gp21$^{313-353}$ sequence-based TCR peptide inhibitor itself or comprising at least one amino acid addition and/or substitution that optimizes binding to CD3δ,ε and TCR ζ subunits relative to the TCR α subunit transmembrane domain (TCRα TMD: V-I-G-F-R-I-L-L-L-K-V-A-G-F-N-L-L-M-T-L) (SEQ ID NO: 78). In one embodiment, the peptide further comprises a C-terminal and/or an N-terminal sugar conjugate. In one embodiment, the sugar conjugate is 1-amino-glucose succinate. In one embodiment, the peptide further comprises a C-terminal and/or an N-terminal lipid conjugate. In one embodiment, the lipid conjugate is selected from the group comprising 2-aminododecanoate or myristoylate. In one embodiment, the lipid conjugate is selected from the group comprising Gly-Tris-monopalmitate, Gly-Tris-dipalmitate, or Gly-Tris-tripalmitate. In one embodiment, the peptide comprises a cyclic peptide. In one embodiment, the peptide comprise a disulfide-linked dimer. In one embodiment, the peptide inhibitor includes amino acids selected from the group including, but not limited to, L-amino acids, or D-amino acids.

In one embodiment, the present invention contemplates a method comprising: a) providing; i) a patient having at least one symptom of a disease or condition where T cells are involved or recruited; and ii) a variant HTLV-1 gp21$^{313-353}$ sequence-based TCR peptide inhibitor itself or comprising at least one amino acid addition and/or substitution that optimizes binding to CD3δ,ε and TCR ζ subunits relative to the TCRα TMD capable of reducing said T cell activation; b) administering said inhibitor to said patient under conditions such that said at least one symptom is reduced. In one embodiment, the medical condition comprises an autoimmune disorder. In one embodiment, the autoimmune disorder is selected from the group consisting of systemic lupus erythematosus, rheumatoid arthritis, multiple sclerosis, type I diabetes, gastroenterological conditions e.g. inflammatory bowel disease e.g. Crohn's disease, primary biliary cirrhosis, chronic active hepatitis; skin problems e.g. atopic dermatitis, psoriasis, pemphigus vulgaris; cardiovascular problems e.g. autoimmune pericarditis.

In one embodiment, the present invention contemplates a variant HVS tyrosine kinase interacting protein (Tip)$^{211-228}$ sequence-based TCR peptide inhibitor itself or comprising at least one amino acid addition and/or substitution that optimizes binding to CD3δ,ε and TCR ζ subunits relative to the TCR α subunit transmembrane domain (TCRα TMD: V-I-G-F-R-I-L-L-L-K-V-A-G-F-N-L-L-M-T-L)) (SEQ ID NO: 78). In one embodiment, the peptide further comprises a C-terminal and/or an N-terminal sugar conjugate. In one embodiment, the sugar conjugate is 1-amino-glucose succinate. In one embodiment, the peptide further comprises a C-terminal and/or an N-terminal lipid conjugate. In one embodiment, the lipid conjugate is selected from the group comprising 2-aminododecanoate or myristoylate. In one embodiment, the lipid conjugate is selected from the group comprising Gly-Tris-monopalmitate, Gly-Tris-dipalmitate, or Gly-Tris-tripalmitate. In one embodiment, the peptide comprises a cyclic peptide. In one embodiment, the peptide comprise a disulfide-linked dimer. In one embodiment, the peptide inhibitor includes amino acids selected from the group including, but not limited to, L-amino acids, or D-amino acids.

In one embodiment, the present invention contemplates a method comprising: a) providing; i) a patient having at least one symptom of a disease or condition where T cells are involved or recruited; and ii) a variant HVS Tip$^{211-228}$ sequence-based TCR peptide inhibitor itself or comprising at least one amino acid addition and/or substitution that optimizes binding to CD3δ,ε and TCR ζ subunits relative to the TCRα TMD capable of reducing said T cell activation; b) administering said inhibitor to said patient under conditions such that said at least one symptom is reduced. In one embodiment, the medical condition comprises an autoimmune disorder. In one embodiment, the autoimmune disorder is selected from the group consisting of systemic lupus erythematosus, rheumatoid arthritis, multiple sclerosis, type I diabetes, gastroenterological conditions e.g. inflammatory bowel disease e.g. Crohn's disease, primary biliary cirrhosis, chronic active hepatitis; skin problems e.g. atopic dermatitis, psoriasis, pemphigus vulgaris; cardiovascular problems e.g. autoimmune pericarditis.

In one embodiment, the present invention contemplates a variant HVA two-in-one protein (Tio)$^{225-242}$ sequence-based TCR peptide inhibitor itself or comprising at least one amino acid addition and/or substitution that optimizes binding to CD3δ,ε and TCR ζ subunits relative to the TCR α subunit transmembrane domain (TCRα TMD: V-I-G-F-R-I-L-L-L-K-V-A-G-F-N-L-L-M-T-L) (SEQ ID NO: 78). In one embodiment, the peptide further comprises a C-terminal and/or an N-terminal sugar conjugate. In one embodiment, the sugar conjugate is 1-amino-glucose succinate. In one embodiment, the peptide further comprises a C-terminal and/or an N-terminal lipid conjugate. In one embodiment, the lipid conjugate is selected from the group comprising 2-aminododecanoate or myristoylate. In one embodiment, the lipid conjugate is selected from the group comprising Gly-Tris-monopalmitate, Gly-Tris-dipalmitate, or Gly-Tris-tripalmitate. In one embodiment, the peptide comprises a cyclic peptide. In one embodiment, the peptide comprise a disulfide-linked dimer. In one embodiment, the peptide inhibitor includes amino acids selected from the group including, but not limited to, L-amino acids, or D-amino acids.

In one embodiment, the present invention contemplates a method comprising: a) providing; i) a patient having at least one symptom of a disease or condition where T cells are involved or recruited; and ii) a variant HVA Tio$^{225-242}$ sequence-based TCR peptide inhibitor itself or comprising at least one amino acid addition and/or substitution that optimizes binding to CD3δ,ε and TCR ζ subunits relative to the TCRα TMD capable of reducing said T cell activation; b) administering said inhibitor to said patient under conditions such that said at least one symptom is reduced. In one embodiment, the medical condition comprises an autoimmune disorder. In one embodiment, the autoimmune disorder is selected from the group consisting of systemic lupus erythematosus, rheumatoid arthritis, multiple sclerosis, type I diabetes, gastroenterological conditions e.g. inflammatory bowel disease e.g. Crohn's disease, primary biliary cirrhosis, chronic active hepatitis; skin problems e.g. atopic dermatitis, psoriasis, pemphigus vulgaris; cardiovascular problems e.g. autoimmune pericarditis.

In one embodiment, the present invention contemplates a peptide inhibitor comprising an amino acid sequence consisting of $X_1$-$X_2$-$X_3$-$X_4$-$X_5$-$X_6$-L-$X_7$-$X_8$-$X_9$-E-$X_{10}$-$X_{11}$-$X_{12}$-$X_{13}$ (SEQ ID NO: 2) wherein $X_1$ consists of R, G, I, L or nothing; $X_2$ consists of N, Q, A or nothing; $X_3$ consists of L, I, S or nothing; $X_4$ consists of V, N, G or nothing; $X_5$, $X_8$, and $X_{11}$ are selected from the group consisting of R, K or H; $X_6$ consists of D, R, S or nothing, $X_7$ consists of K, E, L or nothing, $X_9$ consists of L, V, E or nothing; $X_{10}$ consists of N, K, D or nothing; $X_{12}$ consists of I, L, D or nothing; and $X_{13}$ consists of N, T or nothing. In one embodiment, the peptide further comprises a C-terminal and/or an N-terminal sugar conjugate. In one embodiment, the sugar conjugate is 1-amino-glucose succinate. In one embodiment, the peptide further comprises a C-terminal and/or an N-terminal lipid conjugate. In one embodiment, the lipid conjugate is selected from the group comprising 2-aminododecanoate or myristoylate. In one embodiment, the lipid conjugate is selected from the group comprising Gly-Tris-monopalmitate, Gly-Tris-dipalmitate, or Gly-Tris-tripalmitate. In one embodiment, the peptide comprises a cyclic peptide. In one embodiment, the peptide comprise a disulfide-linked dimer. In one embodiment, the peptide inhibitor includes amino acids selected from the group including, but not limited to, L-amino acids, or D-amino acids.

In one embodiment, the present invention contemplates a method comprising: a) providing; i) a patient having at least one symptom of a disease or condition where T cells are involved or recruited; and ii) a peptide inhibitor comprising an amino acid sequence consisting of $X_1$-$X_2$-$X_3$-$X_4$-$X_5$-$X_6$-L-$X_7$-$X_8$-$X_9$-E-$X_{10}$-$X_{11}$-$X_{12}$-$X_{13}$ (SEQ ID NO: 2) wherein $X_1$ consists of R, G, I, L or nothing; $X_2$ consists of N, Q, A or nothing; $X_3$ consists of L, I, S or nothing; $X_4$ consists of V, N, G or nothing; $X_5$, $X_8$, and $X_{11}$ are selected from the group consisting of R, K or H; $X_6$ consists of D, R, S or nothing, $X_7$ consists of K, E, L or nothing, $X_9$ consists of L, V, E or nothing; $X_{10}$ consists of N, K, D or nothing; $X_{12}$ consists of I, L, D or nothing; and $X_{13}$ consists of N, T or nothing capable of reducing said T cell activation; b) administering said inhibitor to said patient under conditions such that said at least one symptom is reduced. In one embodiment, the medical condition comprises an autoimmune disorder. In one embodiment, the autoimmune disorder is selected from the group consisting of systemic lupus erythematosus, rheumatoid arthritis, multiple sclerosis, type I diabetes, gastroenterological conditions e.g. inflammatory bowel disease e.g. Crohn's disease, primary biliary cirrhosis, chronic active hepatitis; skin problems e.g. atopic dermatitis, psoriasis, pemphigus vulgaris; cardiovascular problems e.g. autoimmune pericarditis.

In one embodiment, the present invention contemplates a variant LASV FP (gp2$^{260-298}$) sequence-based TCR peptide inhibitor itself or comprising at least one amino acid addition and/or substitution that optimizes binding to CD3δ,ε and TCR ζ subunits relative to the TCR α subunit transmembrane domain (TCRα TMD: V-I-G-F-R-I-L-L-L-K-V-A-G-F-N-L-L-M-T-L) (SEQ ID NO: 78). In one embodiment, the peptide further comprises a C-terminal and/or an N-terminal sugar conjugate. In one embodiment, the sugar conjugate is 1-amino-glucose succinate. In one embodiment, the peptide further comprises a C-terminal and/or an N-terminal lipid conjugate. In one embodiment, the lipid conjugate is selected from the group comprising 2-aminododecanoate or myristoylate. In one embodiment, the lipid conjugate is selected from the group comprising Gly-Tris-monopalmitate, Gly-Tris-dipalmitate, or Gly-Tris-tripalmitate. In one embodiment, the peptide comprises a cyclic peptide. In one embodiment, the peptide comprise a disulfide-linked dimer. In one embodiment, the peptide inhibitor includes amino acids selected from the group including, but not limited to, L-amino acids, or D-amino acids.

In one embodiment, the present invention contemplates a method comprising: a) providing; i) a patient having at least one symptom of a disease or condition where T cells are involved or recruited; and ii) a variant LASV FP (gp2$^{260-298}$) sequence-based TCR peptide inhibitor itself or comprising at least one amino acid addition and/or substitution that optimizes binding to CD3δ,ε and TCR ζ subunits relative to the TCRα TMD capable of reducing said T cell activation; b) administering said inhibitor to said patient under conditions such that said at least one symptom is reduced. In one embodiment, the medical condition comprises an autoimmune disorder. In one embodiment, the autoimmune disorder is selected from the group consisting of systemic lupus erythematosus, rheumatoid arthritis, multiple sclerosis, type I diabetes, gastroenterological conditions e.g. inflammatory bowel disease e.g. Crohn's disease, primary biliary cirrhosis, chronic active hepatitis; skin problems e.g. atopic dermatitis, psoriasis, pemphigus vulgaris; cardiovascular problems e.g. autoimmune pericarditis.

In one embodiment, the present invention contemplates a variant LCMV FP (gp2$^{266-304}$) sequence-based TCR peptide inhibitor itself or comprising at least one amino acid addition and/or substitution that optimizes binding to CD3δ,ε and TCR ζ subunits relative to the TCR α subunit transmembrane domain (TCRα TMD: V-I-G-F-R-I-L-L-L-K-V-A-G-F-N-L-L-M-T-L) (SEQ ID NO: 78). In one embodiment, the peptide further comprises a C-terminal and/or an N-terminal sugar conjugate. In one embodiment, the sugar conjugate is 1-amino-glucose succinate. In one embodiment, the peptide further comprises a C-terminal and/or an N-terminal lipid conjugate. In one embodiment, the lipid conjugate is selected from the group comprising 2-aminododecanoate or myristoylate. In one embodiment, the lipid conjugate is selected from the group comprising Gly-Tris-monopalmitate, Gly-Tris-dipalmitate, or Gly-Tris-tripalmitate. In one embodiment, the peptide comprises a cyclic peptide. In one embodiment, the peptide comprise a disulfide-linked dimer. In one embodiment, the peptide inhibitor includes amino acids selected from the group including, but not limited to, L-amino acids, or D-amino acids.

In one embodiment, the present invention contemplates a method comprising: a) providing; i) a patient having at least one symptom of a disease or condition where T cells are involved or recruited; and ii) a variant LCMV FP (gp2$^{266-304}$) sequence-based TCR peptide inhibitor itself or comprising at least one amino acid addition and/or substitution that optimizes binding to CD3δ,ε and TCR ζ subunits relative to the TCRα TMD capable of reducing said T cell activation; b) administering said inhibitor to said patient under conditions such that said at least one symptom is reduced. In one embodiment, the medical condition comprises an autoimmune disorder. In one embodiment, the autoimmune disorder is selected from the group consisting of systemic lupus erythematosus, rheumatoid arthritis, multiple sclerosis, type I diabetes, gastroenterological conditions e.g. inflammatory bowel disease e.g. Crohn's disease, primary biliary cirrhosis, chronic active hepatitis; skin problems e.g. atopic dermatitis, psoriasis, pemphigus vulgaris; cardiovascular problems e.g. autoimmune pericarditis.

In one embodiment, the present invention contemplates a variant MOPV FP (gp2$^{258-296}$) sequence-based TCR peptide inhibitor itself or comprising at least one amino acid addition and/or substitution that optimizes binding to CD3δ,ε and TCR ζ subunits relative to the TCR α subunit transmembrane domain (TCRα TMD: V-I-G-F-R-I-L-L-L-K-V-A-G-F-N-L-L-M-T-L) (SEQ ID NO: 78). In one embodiment, the peptide further comprises a C-terminal and/or an N-terminal sugar conjugate. In one embodiment, the sugar conjugate is 1-amino-glucose succinate. In one embodiment, the peptide further comprises a C-terminal and/or an N-terminal lipid conjugate. In one embodiment, the lipid conjugate is selected from the group comprising 2-aminododecanoate or myristoylate. In one embodiment, the lipid conjugate is selected from the group comprising Gly-Tris-monopalmitate, Gly-Tris-dipalmitate, or Gly-Tris-tripalmitate. In one embodiment, the peptide comprises a cyclic peptide. In one embodiment, the peptide comprise a disulfide-linked dimer. In one embodiment, the peptide inhibitor includes amino acids selected from the group including, but not limited to, L-amino acids, or D-amino acids.

In one embodiment, the present invention contemplates a method comprising: a) providing; i) a patient having at least one symptom of a disease or condition where T cells are involved or recruited; and ii) a variant MOPV FP (gp2$^{258-296}$) sequence-based TCR peptide inhibitor itself or comprising at least one amino acid addition and/or substitution that optimizes binding to CD3δ,ε and TCR ζ subunits relative to the TCRα TMD capable of reducing said T cell activation; b) administering said inhibitor to said patient under conditions such that said at least one symptom is reduced. In one embodiment, the medical condition comprises an autoimmune disorder. In one embodiment, the autoimmune disorder is selected from the group consisting of systemic lupus erythematosus, rheumatoid arthritis, multiple sclerosis, type I diabetes, gastroenterological conditions e.g. inflammatory bowel disease e.g. Crohn's disease, primary biliary cirrhosis, chronic active hepatitis; skin problems e.g. atopic dermatitis, psoriasis, pemphigus vulgaris; cardiovascular problems e.g. autoimmune pericarditis.

In one embodiment, the present invention contemplates a variant TACV FP (gp2$^{262-300}$) sequence-based TCR peptide inhibitor itself or comprising at least one amino acid addition and/or substitution that optimizes binding to CD3δ,ε and TCR ζ subunits relative to the TCR α subunit transmembrane domain (TCRα TMD: V-I-G-F-R-I-L-L-L-K-V-A-G-F-N-L-L-M-T-L) (SEQ ID NO: 78). In one embodiment, the peptide further comprises a C-terminal and/or an N-terminal sugar conjugate. In one embodiment, the sugar conjugate is 1-amino-glucose succinate. In one embodiment, the peptide further comprises a C-terminal and/or an N-terminal lipid conjugate. In one embodiment, the lipid conjugate is selected from the group comprising 2-aminododecanoate or myristoylate. In one embodiment, the lipid conjugate is selected from the group comprising Gly-Tris-monopalmitate, Gly-Tris-dipalmitate, or Gly-Tris-tripalmitate. In one embodiment, the peptide comprises a cyclic peptide. In one embodiment, the peptide comprise a disulfide-linked dimer. In one embodiment, the peptide inhibitor includes amino acids selected from the group including, but not limited to, L-amino acids, or D-amino acids.

In one embodiment, the present invention contemplates a method comprising: a) providing; i) a patient having at least one symptom of a disease or condition where T cells are involved or recruited; and ii) a variant TACV FP (gp2$^{262-300}$)

sequence-based TCR peptide inhibitor itself or comprising at least one amino acid addition and/or substitution that optimizes binding to CD3δ,ε and TCR ζ subunits relative to the TCRα TMD capable of reducing said T cell activation; b) administering said inhibitor to said patient under conditions such that said at least one symptom is reduced. In one embodiment, the medical condition comprises an autoimmune disorder. In one embodiment, the autoimmune disorder is selected from the group consisting of systemic lupus erythematosus, rheumatoid arthritis, multiple sclerosis, type I diabetes, gastroenterological conditions e.g. inflammatory bowel disease e.g. Crohn's disease, primary biliary cirrhosis, chronic active hepatitis; skin problems e.g. atopic dermatitis, psoriasis, pemphigus vulgaris; cardiovascular problems e.g. autoimmune pericarditis.

In one embodiment, the present invention contemplates a variant CKS-17 sequence-based TCR peptide inhibitor itself or comprising at least one amino acid addition and/or substitution that optimizes binding to CD3δ,ε and TCR ζ subunits relative to the TCR α subunit transmembrane domain (TCRα TMD: V-I-G-F-R-I-L-L-L-K-V-A-G-F-N-L-L-M-T-L) (SEQ ID NO: 78). In one embodiment, the peptide further comprises a C-terminal and/or an N-terminal sugar conjugate. In one embodiment, the sugar conjugate is 1-amino-glucose succinate. In one embodiment, the peptide further comprises a C-terminal and/or an N-terminal lipid conjugate. In one embodiment, the lipid conjugate is selected from the group comprising 2-aminododecanoate or myristoylate. In one embodiment, the lipid conjugate is selected from the group comprising Gly-Tris-monopalmitate, Gly-Tris-dipalmitate, or Gly-Tris-tripalmitate. In one embodiment, the peptide comprises a cyclic peptide. In one embodiment, the peptide comprise a disulfide-linked dimer. In one embodiment, the peptide inhibitor includes amino acids selected from the group including, but not limited to, L-amino acids, or D-amino acids.

In one embodiment, the present invention contemplates a method comprising: a) providing; i) a patient having at least one symptom of a disease or condition where T cells are involved or recruited; and ii) a variant CKS-17 sequence-based TCR peptide inhibitor itself or comprising at least one amino acid addition and/or substitution that optimizes binding to CD3δ,ε and TCR ζ subunits relative to the TCRα TMD capable of reducing said T cell activation; b) administering said inhibitor to said patient under conditions such that said at least one symptom is reduced. In one embodiment, the medical condition comprises an autoimmune disorder. In one embodiment, the autoimmune disorder is selected from the group consisting of systemic lupus erythematosus, rheumatoid arthritis, multiple sclerosis, type I diabetes, gastroenterological conditions e.g. inflammatory bowel disease e.g. Crohn's disease, primary biliary cirrhosis, chronic active hepatitis; skin problems e.g. atopic dermatitis, psoriasis, pemphigus vulgaris; cardiovascular problems e.g. autoimmune pericarditis.

In one embodiment, the present invention contemplates a variant SEBOV gp2$^{584-600}$ sequence-based TCR peptide inhibitor itself or comprising at least one amino acid addition and/or substitution that optimizes binding to CD3δ,ε and TCR ζ subunits relative to the TCR α subunit transmembrane domain (TCRα TMD: V-I-G-F-R-I-L-L-L-K-V-A-G-F-N-L-L-M-T-L) (SEQ ID NO: 78). In one embodiment, the peptide further comprises a C-terminal and/or an N-terminal sugar conjugate. In one embodiment, the sugar conjugate is 1-amino-glucose succinate. In one embodiment, the peptide further comprises a C-terminal and/or an N-terminal lipid conjugate. In one embodiment, the lipid conjugate is selected from the group comprising 2-aminododecanoate or myristoylate. In one embodiment, the lipid conjugate is selected from the group comprising Gly-Tris-monopalmitate, Gly-Tris-dipalmitate, or Gly-Tris-tripalmitate. In one embodiment, the peptide comprises a cyclic peptide. In one embodiment, the peptide comprise a disulfide-linked dimer. In one embodiment, the peptide inhibitor includes amino acids selected from the group including, but not limited to, L-amino acids, or D-amino acids.

In one embodiment, the present invention contemplates a method comprising: a) providing; i) a patient having at least one symptom of a disease or condition where T cells are involved or recruited; and ii) a variant SEBOV gp2$^{584-600}$ sequence-based TCR peptide inhibitor itself or comprising at least one amino acid addition and/or substitution that optimizes binding to CD3δ,ε and TCR ζ subunits relative to the TCRα TMD capable of reducing said T cell activation; b) administering said inhibitor to said patient under conditions such that said at least one symptom is reduced. In one embodiment, the medical condition comprises an autoimmune disorder. In one embodiment, the autoimmune disorder is selected from the group consisting of systemic lupus erythematosus, rheumatoid arthritis, multiple sclerosis, type I diabetes, gastroenterological conditions e.g. inflammatory bowel disease e.g. Crohn's disease, primary biliary cirrhosis, chronic active hepatitis; skin problems e.g. atopic dermatitis, psoriasis, pemphigus vulgaris; cardiovascular problems e.g. autoimmune pericarditis.

In one embodiment, the present invention contemplates a variant ZEBOV gp2$^{584-600}$ sequence-based TCR peptide inhibitor itself or comprising at least one amino acid addition and/or substitution that optimizes binding to CD3δ,ε and TCR ζ subunits relative to the TCR α subunit transmembrane domain (TCRα TMD: V-I-G-F-R-I-L-L-L-K-V-A-G-F-N-L-L-M-T-L) (SEQ ID NO: 78). In one embodiment, the peptide further comprises a C-terminal and/or an N-terminal sugar conjugate. In one embodiment, the sugar conjugate is 1-amino-glucose succinate. In one embodiment, the peptide further comprises a C-terminal and/or an N-terminal lipid conjugate. In one embodiment, the lipid conjugate is selected from the group comprising 2-aminododecanoate or myristoylate. In one embodiment, the lipid conjugate is selected from the group comprising Gly-Tris-monopalmitate, Gly-Tris-dipalmitate, or Gly-Tris-tripalmitate. In one embodiment, the peptide comprises a cyclic peptide. In one embodiment, the peptide comprise a disulfide-linked dimer. In one embodiment, the peptide inhibitor includes amino acids selected from the group including, but not limited to, L-amino acids, or D-amino acids.

In one embodiment, the present invention contemplates a method comprising: a) providing; i) a patient having at least one symptom of a disease or condition where T cells are involved or recruited; and ii) a variant ZEBOV gp2$^{584-600}$ sequence-based TCR peptide inhibitor itself or comprising at least one amino acid addition and/or substitution that optimizes binding to CD3δ,ε and TCR ζ subunits relative to the TCRα TMD capable of reducing said T cell activation; b) administering said inhibitor to said patient under conditions such that said at least one symptom is reduced. In one embodiment, the medical condition comprises an autoimmune disorder. In one embodiment, the autoimmune disorder is selected from the group consisting of systemic lupus erythematosus, rheumatoid arthritis, multiple sclerosis, type I diabetes, gastroenterological conditions e.g. inflammatory bowel disease e.g. Crohn's disease, primary biliary cirrhosis, chronic active hepatitis; skin problems e.g. atopic dermatitis, psoriasis, pemphigus vulgaris; cardiovascular problems e.g. autoimmune pericarditis.

In one embodiment, the present invention contemplates a variant MARV gp2$^{585-601}$ sequence-based TCR peptide inhibitor itself or comprising at least one amino acid addition and/or substitution that optimizes binding to CD3δ,ε and TCR ζ subunits relative to the TCR α subunit transmembrane domain (TCRα TMD: V-I-G-F-R-I-L-L-L-K-V-A-G-F-N-L-L-M-T-L) (SEQ ID NO: 78). In one embodiment, the peptide further comprises a C-terminal and/or an N-terminal sugar conjugate. In one embodiment, the sugar conjugate is 1-amino-glucose succinate. In one embodiment, the peptide further comprises a C-terminal and/or an N-terminal lipid conjugate. In one embodiment, the lipid conjugate is selected from the group comprising 2-aminododecanoate or myristoylate. In one embodiment, the lipid conjugate is selected from the group comprising Gly-Tris-monopalmitate, Gly-Tris-dipalmitate, or Gly-Tris-tripalmitate. In one embodiment, the peptide comprises a cyclic peptide. In one embodiment, the peptide comprise a disulfide-linked dimer. In one embodiment, the peptide inhibitor includes amino acids selected from the group including, but not limited to, L-amino acids, or D-amino acids.

In one embodiment, the present invention contemplates a method comprising: a) providing; i) a patient having at least one symptom of a disease or condition where T cells are involved or recruited; and ii) a variant MARV gp2$^{585-601}$ sequence-based TCR peptide inhibitor itself or comprising at least one amino acid addition and/or substitution that optimizes binding to CD3δ,ε and TCR ζ subunits relative to the TCRα TMD capable of reducing said T cell activation; b) administering said inhibitor to said patient under conditions such that said at least one symptom is reduced. In one embodiment, the medical condition comprises an autoimmune disorder. In one embodiment, the autoimmune disorder is selected from the group consisting of systemic lupus erythematosus, rheumatoid arthritis, multiple sclerosis, type I diabetes, gastroenterological conditions e.g. inflammatory bowel disease e.g. Crohn's disease, primary biliary cirrhosis, chronic active hepatitis; skin problems e.g. atopic dermatitis, psoriasis, pemphigus vulgaris; cardiovascular problems e.g. autoimmune pericarditis.

In one embodiment, the present invention contemplates a variant Fr-MLV Env gp$^{548-564}$ sequence-based TCR peptide inhibitor itself or comprising at least one amino acid addition and/or substitution that optimizes binding to CD3δ,ε and TCR ζ subunits relative to the TCR α subunit transmembrane domain (TCRα TMD: V-I-G-F-R-I-L-L-L-K-V-A-G-F-N-L-L-M-T-L) (SEQ ID NO: 78). In one embodiment, the peptide further comprises a C-terminal and/or an N-terminal sugar conjugate. In one embodiment, the sugar conjugate is 1-amino-glucose succinate. In one embodiment, the peptide further comprises a C-terminal and/or an N-terminal lipid conjugate. In one embodiment, the lipid conjugate is selected from the group comprising 2-aminododecanoate or myristoylate. In one embodiment, the lipid conjugate is selected from the group comprising Gly-Tris-monopalmitate, Gly-Tris-dipalmitate, or Gly-Tris-tripalmitate. In one embodiment, the peptide comprises a cyclic peptide. In one embodiment, the peptide comprise a disulfide-linked dimer. In one embodiment, the peptide inhibitor includes amino acids selected from the group including, but not limited to, L-amino acids, or D-amino acids.

In one embodiment, the present invention contemplates a method comprising: a) providing; i) a patient having at least one symptom of a disease or condition where T cells are involved or recruited; and ii) a variant Fr-MLV Env gp$^{548-564}$ sequence-based TCR peptide inhibitor itself or comprising at least one amino acid addition and/or substitution that optimizes binding to CD3δ,ε and TCR ζ subunits relative to the TCRα TMD capable of reducing said T cell activation; b) administering said inhibitor to said patient under conditions such that said at least one symptom is reduced. In one embodiment, the medical condition comprises an autoimmune disorder. In one embodiment, the autoimmune disorder is selected from the group consisting of systemic lupus erythematosus, rheumatoid arthritis, multiple sclerosis, type I diabetes, gastroenterological conditions e.g. inflammatory bowel disease e.g. Crohn's disease, primary biliary cirrhosis, chronic active hepatitis; skin problems e.g. atopic dermatitis, psoriasis, pemphigus vulgaris; cardiovascular problems e.g. autoimmune pericarditis.

In one embodiment, the present invention contemplates a variant HHV-6 U24$^{28-60}$ sequence-based TCR peptide inhibitor itself or comprising at least one amino acid addition and/or substitution that optimizes binding to CD3δ,ε and TCR ζ subunits relative to the TCR α subunit transmembrane domain (TCRα TMD: V-I-G-F-R-I-L-L-L-K-V-A-G-F-N-L-L-M-T-L) (SEQ ID NO: 78). In one embodiment, the peptide further comprises a C-terminal and/or an N-terminal sugar conjugate. In one embodiment, the sugar conjugate is 1-amino-glucose succinate. In one embodiment, the peptide further comprises a C-terminal and/or an N-terminal lipid conjugate. In one embodiment, the lipid conjugate is selected from the group comprising 2-aminododecanoate or myristoylate. In one embodiment, the lipid conjugate is selected from the group comprising Gly-Tris-monopalmitate, Gly-Tris-dipalmitate, or Gly-Tris-tripalmitate. In one embodiment, the peptide comprises a cyclic peptide. In one embodiment, the peptide comprise a disulfide-linked dimer. In one embodiment, the peptide inhibitor includes amino acids selected from the group including, but not limited to, L-amino acids, or D-amino acids.

In one embodiment, the present invention contemplates a method comprising: a) providing; i) a patient having at least one symptom of a disease or condition where T cells are involved or recruited; and ii) a variant HHV-6 U24$^{28-60}$ sequence-based TCR peptide inhibitor itself or comprising at least one amino acid addition and/or substitution that optimizes binding to CD3δ,ε and TCR ζ subunits relative to the TCRα TMD capable of reducing said T cell activation; b) administering said inhibitor to said patient under conditions such that said at least one symptom is reduced. In one embodiment, the medical condition comprises an autoimmune disorder. In one embodiment, the autoimmune disorder is selected from the group consisting of systemic lupus erythematosus, rheumatoid arthritis, multiple sclerosis, type I diabetes, gastroenterological conditions e.g. inflammatory bowel disease e.g. Crohn's disease, primary biliary cirrhosis, chronic active hepatitis; skin problems e.g. atopic dermatitis, psoriasis, pemphigus vulgaris; cardiovascular problems e.g. autoimmune pericarditis.

In one embodiment, the present invention contemplates a peptide inhibitor comprising an amino acid sequence consisting of L-N-$X_1$-$X_2$-$X_3$-L-$X_4$-$X_5$-L-$X_6$-L-$X_7$-$X_8$-G-G-$X_9$ (SEQ ID NO: 3) wherein $X_1$ and $X_7$ are selected from the group consisting of R, K or H; $X_2$ consists of S, R, K, H, P or W; $X_3$ consists of M, G or A; $X_4$ consists of L, I, V, N or D; $X_5$ consists of L, I, F, T, E, A or G; $X_6$ consists of E, Q, D, L, F, N or I, $X_8$ consists of Q, C, E, W or R, and $X_9$ consists of L, I, F, T, N or nothing. In one embodiment, the peptide further comprises a C-terminal and, or an N-terminal sugar conjugate. In one embodiment, the sugar conjugate is 1-amino-glucose succinate. In one embodiment, the peptide further comprises a C-terminal and/or an N-terminal lipid conjugate. In one embodiment, the lipid conjugate is selected from the group comprising 2-aminododecanoate or myristoylate. In one embodiment, the lipid conjugate is selected from the group comprising Gly-Tris-monopalmitate, Gly-Tris-dipalmitate, or Gly-Tris-tripalmitate. In one embodiment, the peptide comprises a cyclic peptide. In one embodiment, the peptide comprise a disulfide-linked dimer. In one embodiment, the peptide inhibitor includes amino acids selected from the group including, but not limited to, L-amino acids, or D-amino acids.

In one embodiment, the present invention contemplates a method comprising: a) providing; i) a patient having at least one symptom of a disease or condition where T cells are involved or recruited; and ii) a peptide inhibitor comprising an amino acid sequence consisting of L-N-$X_1$-$X_2$-$X_3$-L-$X_4$-$X_5$-L-$X_6$-L-$X_7$-$X_8$-G-G-$X_9$ (SEQ ID NO: 3) wherein $X_1$ and $X_7$ are selected from the group consisting of R, K or H; $X_2$ consists of S, R, K, H, P or W; $X_3$ consists of M, G or A; $X_4$ consists of L, I, V, N or D; $X_5$ consists of L, I, F, T, E, A or G; $X_6$ consists of E, Q, D, L, F, N or I, $X_8$ consists of Q, C, E, W or R, and $X_9$ consists of L, I, F, T, N or nothing capable of reducing said T cell activation; b) administering said inhibitor to said patient under conditions such that said at least one symptom is reduced. In one embodiment, the medical condition comprises an autoimmune disorder. In one embodiment, the autoimmune disorder is selected from the group consisting of systemic lupus erythematosus, rheumatoid arthritis, multiple sclerosis, type I diabetes, gastroenterological conditions e.g. inflammatory bowel disease e.g. Crohn's disease, primary biliary cirrhosis, chronic active hepatitis; skin problems e.g. atopic dermatitis, psoriasis, pemphigus vulgaris; cardiovascular problems e.g. autoimmune pericarditis.

In one embodiment, the present invention contemplates a peptide inhibitor comprising an amino acid sequence consisting of L-Q-N-$X_1$-$X_2$-L-$X_3$-$X_4$-$X_5$-$X_6$-$X_7$-L-$X_8$-$X_9$-$X_{10}$-$X_{11}$-$X_{12}$ (SEQ ID NO: 4) wherein $X_1$, $X_4$ and $X_8$ are selected from the group consisting of R, K or H; $X_2$ consists of D, R or S; $X_3$ consists of E, K or L; $X_5$ and $X_7$ consist of L, I, or T; $X_6$ consists of L, I, or P; $X_9$ consists of Q, C, E, W or R, $X_{10}$ consists of K, G, F, L, I or nothing; $X_{11}$ consists of T, G or nothing; and $X_{12}$ consists of F, L, I, T, N or nothing. In one embodiment, the peptide further comprises a C-terminal and/or an N-terminal sugar conjugate. In one embodiment, the sugar conjugate is 1-amino-glucose succinate. In one embodiment, the peptide further comprises a C-terminal and/or an N-terminal lipid conjugate. In one embodiment, the lipid conjugate is selected from the group comprising 2-aminododecanoate or myristoylate. In one embodiment, the lipid conjugate is selected from the group comprising Gly-Tris-monopalmitate, Gly-Tris-dipalmitate, or Gly-Tris-tripalmitate. In one embodiment, the peptide comprises a cyclic peptide. In one embodiment, the peptide comprise a disulfide-linked dimer. In one embodiment, the peptide inhibitor includes amino acids selected from the group including, but not limited to, L-amino acids, or D-amino acids.

In one embodiment, the present invention contemplates a method comprising: a) providing; i) a patient having at least one symptom of a disease or condition where T cells are involved or recruited; and ii) a peptide inhibitor comprising an amino acid sequence consisting of L-Q-N-$X_1$-$X_2$-L-$X_3$-$X_4$-$X_5$-$X_6$-$X_7$-L-$X_8$-$X_9$-$X_{10}$-$X_{11}$-$X_{12}$ (SEQ ID NO: 4) wherein $X_1$, $X_4$ and $X_8$ are selected from the group consisting of R, K or H; $X_2$ consists of D, R or S; $X_3$ consists of E, K or L; $X_5$ and $X_7$ consist of L, I, or T; $X_6$ consists of L, I, or P; $X_9$ consists of Q, C, E, W or R, $X_{10}$ consists of K, G, F, L, I or nothing; $X_{11}$ consists of T, G or nothing; and $X_{12}$ consists of F, L, I, T, N or nothing capable of reducing said T cell activation; b) administering said inhibitor to said patient under conditions such that said at least one symptom is reduced. In one embodiment, the medical condition comprises an autoimmune disorder. In one embodiment, the autoimmune disorder is selected from the group consisting of systemic lupus erythematosus, rheumatoid arthritis, multiple sclerosis, type I diabetes, gastroenterological conditions e.g. inflammatory bowel disease e.g. Crohn's disease, primary biliary cirrhosis, chronic active hepatitis; skin problems e.g. atopic dermatitis, psoriasis, pemphigus vulgaris; cardiovascular problems e.g. autoimmune pericarditis.

In one embodiment, the present invention contemplates a peptide inhibitor comprising an amino acid sequence consisting of L-Q-N-$X_1$-$X_2$-$X_3$-$X_4$-L-$X_5$-$X_6$-L-X-$_7$-$X_8$-$X_9$-$X_{10}$-$X_{11}$-$X_{12}$ (SEQ ID NO: 5) wherein $X_1$, $X_5$ and $X_8$ are selected from the group consisting of R, K or H; $X_2$ and $X_4$ consist of L, I, or T; $X_3$ consists of L, I, or P; $X_6$ consists of D, R or S; $X_7$ consists of E, K or L; $X_9$ consists of Q, C, E, W or R, $X_{10}$ consists of K, G, F, L, I or nothing; $X_{11}$ consists of T, G or nothing; and $X_{12}$ consists of F, L, I, T, N or nothing. In one embodiment, the peptide further comprises a C-terminal and/or an N-terminal sugar conjugate. In one embodiment, the sugar conjugate is 1-amino-glucose succinate. In one embodiment, the peptide further comprises a C-terminal and/or an N-terminal lipid conjugate. In one embodiment, the lipid conjugate is selected from the group comprising 2-aminododecanoate or myristoylate. In one embodiment, the lipid conjugate is selected from the group comprising Gly-Tris-monopalmitate, Gly-Tris-dipalmitate, or Gly-Tris-tripalmitate. In one embodiment, the peptide comprises a cyclic peptide. In one embodiment, the peptide comprise a disulfide-linked dimer. In one embodiment, the peptide inhibitor includes amino acids selected from the group including, but not limited to, L-amino acids, or D-amino acids.

In one embodiment, the present invention contemplates a method comprising: a) providing; i) a patient having at least one symptom of a disease or condition where T cells are involved or recruited; and ii) a peptide inhibitor comprising an amino acid sequence consisting of L-Q-N-$X_1$-$X_2$-$X_3$-$X_4$-L-$X_5$-$X_6$-L-$X_7$-$X_8$-$X_9$-$X_{10}$-$X_{11}$-$X_{12}$ (SEQ ID NO: 5) wherein $X_1$, $X_5$ and $X_8$ are selected from the group consisting of R, K or H; $X_2$ and $X_4$ consist of L, I, or T; $X_3$ consists of L, I, or P; $X_6$ consists of D, R or S; $X_7$ consists of E, K or L; $X_9$ consists of Q, C, E, W or R, $X_{10}$ consists of K, G, F, L, I or nothing; $X_{11}$ consists of T, G or nothing; and $X_{12}$ consists of F, L, I, T, N or nothing capable of reducing said T cell activation; b) administering said inhibitor to said patient under conditions such that said at least one symptom is reduced. In one embodiment, the medical condition comprises an autoimmune disorder. In one embodiment, the autoimmune disorder is selected from the group consisting of systemic lupus erythematosus, rheumatoid arthritis, multiple sclerosis, type I diabetes, gastroenterological conditions e.g. inflammatory bowel disease e.g. Crohn's disease, primary biliary cirrhosis, chronic active hepatitis; skin problems e.g. atopic dermatitis, psoriasis, pemphigus vulgaris; cardiovascular problems e.g. autoimmune pericarditis.

In one embodiment, the present invention contemplates a protease-resistance immunotherapeutic peptide comprising a variant transmembrane peptide derived from amino acid sequences (or from combinations thereof) of fusion and other protein regions of various viruses, including but not limiting to, SARS-CoV, HVS, HHV-6, LASV, LCMV, MOPV, TACV, Fr-MLV; HTLV-1; HVA; MARV; SEBOV; ZEBOV. In one embodiment, the variant peptide comprises at least one D-amino acid.

In one embodiment, the present invention contemplates a disulfide-linked dimer of an immunotherapeutic peptide comprising a variant transmembrane peptide derived from amino acid sequences (or from combinations thereof) of fusion and other protein regions of various viruses, including but not limited to, SARS-CoV, HVS, HHV-6, LASV, LCMV, MOPV, TACV, Fr-MLV; HTLV-1; HVA; MARV; SEBOV; ZEBOV.

In one embodiment, the present invention contemplates a cyclic immunotherapeutic peptide comprising a variant transmembrane peptide derived from amino acid sequences (or from combinations thereof) of fusion and other protein regions of various viruses, including but not limited to, SARS-CoV, HVS, HHV-6, LASV, LCMV, MOPV, TACV, Fr-MLV; HTLV-1; HVA; MARV; SEBOV; ZEBOV.

In one embodiment, the present invention contemplates a medical device comprising a coating, wherein said coating comprises the peptide derivative of claim 1. In one embodiment, the coating further comprises a polymer. In one embodiment, the polymer is selected from the group including, but not limited to, phosphorylcholine, polyvinyl pyrrolidone, poly(acrylic acid), poly(vinyl acetamide), poly(propylene glycol), poly(ethylene co-vinyl acetate), poly(n-butyl methacrylate) or poly(styrene-b-isobutylene-b-styrene). In one embodiment, the medical device is selected from the group including, but not limited to, stents, grafts, implantable devices, catheters, endoscopes (i.e., for example, laparoscopes), atrial/venous fistulas, or cannulae.

BRIEF DESCRIPTION OF THE FIGURES

The following figures form part of the present specification and are included to further illustrate aspects of the present invention. The invention may be better understood by reference to the figures in combination with the detailed description of the specific embodiments presented herein.

FIG. 5 (SEQ ID NOS: 78, 76, 6, 7, 28, 26, 77, 8, 41, 43, 45, 47, 48, 49, 50, 47, and 51, respectively) illustrates one embodiment of similarities in the charge distribution patterns of different immunomodulatory viral sequences. Primary sequence analysis of proven and predicted immunomodulatory sequences of viral fusion protein regions and other domains shows a similarity in charge distribution pattern with two essential positively charged residues spaced apart by 4 (class I) or 8 (class III) amino acids or with three essential positively charged residues spaced apart by 3 amino acids (class II), suggesting a similarity of the SCHOOL-based mechanisms used by diverse viruses in their pathogenesis to modulate the host immune response. Abbreviations: TCR, T cell receptor; CP, core peptide, HIV, human immunodeficiency virus; gp, glycoprotein; FP, fusion peptide/protein; TMD, transmembrane domain; CKS-17, a synthetic retroviral envelope heptadecapeptide; Fr-MLV, Friend murine leukemia virus; gp, glycoprotein; HHV-6 U24, human herpesvirus 6 U24 protein; HTLV-1, human T lymphotropic virus type 1; HVA, herpesvirus aides; HVS, herpesvirus saimiri; ITAM, immunoreceptor tyrosine-based activation motif; LASV, Lassa virus; LCMV, lymphocytic choriomeningitis virus; MARV, Marburg virus; MOPV, Mopeia virus; SARS-CoV, severe acute respiratory syndrome coronavirus; SEBOV, Sudan Ebola virus; TACV, Tacaribe virus; Tip, tyrosine kinase interacting protein; Tio, two-in-one protein; TMD, transmembrane domain; ZEBOV, Zaire Ebola virus.

FIG. 10 presents various embodiments of the combinatorial TCR peptide inhibitor sequences based upon a combination of general formulas, wherein in the general formula describes variants of the parent sequences of SARS-CoV FP, HTLV-1 $gp21^{313-353}$, HVA $Tio^{225-242}$, HVS $Tip^{211-228}$, LASV FP ($gp2^{260-298}$), LCMV FP ($gp2^{266-304}$), MOPV FP ($gp2^{258-296}$), TACV FP ($gp2^{262-300}$), CKS-17, SEBOV $gp2^{584-600}$, ZEBOV $gp2^{584-600}$, MARV $gp2^{585-601}$, Fr-MLV Env $gp^{548-564}$ and HHV-6 $U24^{28-60}$.

Definitions

Figure 1A:
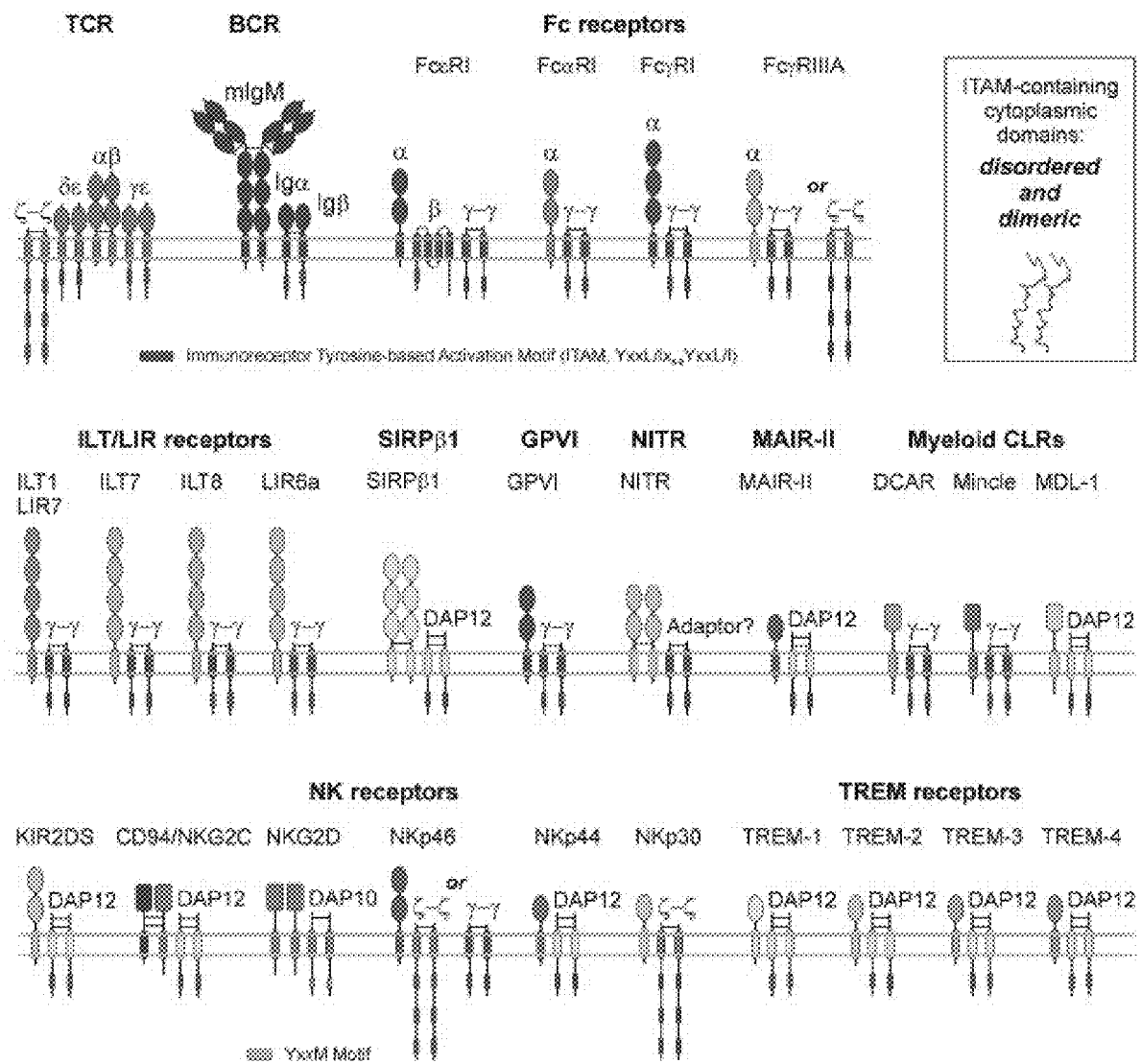
FIG. 1A presents a schematic representation of one embodiment of Multichain Immune Recognition Receptors (MIRRs) expressed on many different immune cells—including T and B cells, natural killer cells, mast cells, macrophages, basophils, neutrophils, eosinophils and dendritic cells—and on platelets. Position of MIRRs relative to the cell membrane is indicated by blue lines. Cytoplasmic domains of the MIRR signaling subunits represent a novel class of intrinsically disordered proteins and are shown to be dimeric. Abbreviations: BCR, B cell receptor; DAP-10 and DAP-12, DNAX adapter proteins of 10 and 12 kD, respectively; DCAR, dendritic cell immunoactivating receptor; GPVI, glycoprotein VI; ILT, Ig-like transcript; KIR, killer cell Ig-like receptor; LIR, leukocyte Ig-like receptor; MAIR-II, myeloid-associated Ig-like receptor; MDL-1, myeloid DAP 12-associating lectin 1; NITR, novel immune-type receptor; NK, natural killer cells; SIRP, signal regulatory protein, TCR, T cell receptor; TREM receptors, triggering receptors expressed on myeloid cells.

The term "T cell-mediated pathology" (or "T cell-related pathologies", or "T cell-mediated disorder", or "T cell-related disease"), as used herein, refers to any condition in which an inappropriate T cell response is a component of the pathology. The term is intended to include both diseases directly mediated by T cells, and also diseases in which an inappropriate T cell response contributes to the production of abnormal antibodies, as well as graft rejection.

The term "ligand-induced T cell activation", as used herein, refers to T cell activation in response to the stimulation by the specific ligand.

The term "stimulation", as used herein, refers to a primary response induced by ligation of a cell surface moiety. For example, in the context of receptors, such stimulation entails the ligation of a receptor and a subsequent signal transduction event. With respect to stimulation of a T cell, such stimulation refers to the ligation of a T cell surface moiety that in one embodiment subsequently induces a signal transduction event, such as binding the TCR/CD3 complex. Further, the stimulation event may activate a cell and upregulate or downregulate expression or secretion of a molecule.

The term "ligand", or "antigen", as used herein, refers to a stimulating molecule that binds to a defined population of cells. The ligand may bind any cell surface moiety, such as a receptor, an antigenic determinant, or other binding site present on the target cell population. The ligand may be a protein, peptide, antibody and antibody fragments thereof, fusion proteins, synthetic molecule, an organic molecule (e.g., a small molecule), or the like. Within the specification and in the context of T cell stimulation, the ligand (or antigen) binds the T cell antigen receptor and this binding activates the T cell.

The term "activation", as used herein, refers to the state of a cell following sufficient cell surface moiety ligation to induce a noticeable biochemical or morphological change. Within the context of T cells, such activation, refers to the state of a T cell that has been sufficiently stimulated to induce cellular proliferation. Activation of a T cell may also induce cytokine production and performance of regulatory or cytolytic effector functions. Within the context of other cells, this term infers either up or down regulation of a particular physico-chemical process.

The term "inhibiting T cell activation", as used herein, refers to the slowing of T cell activation, as well as completely eliminating and/or preventing T cell activation.

The term, "treating a disease or condition", as used herein, refers to modulating T cell activation including, but not limited to, decreasing cellular proliferation, cytokine production and performance of regulatory or cytolytic effector functions and/or slowing T cell activation, as well as completely eliminating and/or preventing T cell activation. T cell-related diseases and/or conditions treatable by modulating T cell activation include, but are not limited to, systemic lupus erythematosus, rheumatoid arthritis, multiple sclerosis, type I diabetes, gastroenterological conditions e.g. inflammatory bowel disease e.g. Crohn's disease, Guillain-Barre syndrome, Hashimotos disease, pernicious anaemia, primary biliary cirrhosis, chronic active hepatitis; skin problems e.g. atopic dermatitis, psoriasis, pemphigus vulgaris; cardiovascular problems e.g. autoimmune pericarditis, allergic diathesis e.g. Delayed type hypersensitivity, contact dermatitis, AIDS virus, herpes simplex/zoster, respiratory conditions e.g. allergic alveolitis, inflammatory conditions e.g. myositis, ankylosing spondylitis, tissue/organ rejection.

The term, "subject" or "patient", as used herein, refers to any individual organism. For example, the organism may be a mammal such as a primate (i.e., for example, a human). Further, the organism may be a domesticated animal (i.e., for example, cats, dogs, etc.), livestock (i.e., for example, cattle, horses, pigs, sheep, goats, etc.), or a laboratory animal (i.e., for example, mouse, rabbit, rat, guinea pig, etc.).

The term, "therapeutically effective amount", "therapeutically effective dose" or "effective amount", as used herein, refers to an amount needed to achieve a desired clinical result or results (inhibiting TCR-mediated cell activation) based upon trained medical observation and/or quantitative test results. The potency of any administered peptide or compound determines the "effective amount" which can vary for the various compounds that inhibit T cell activation (i.e., for example, compounds inhibiting antigen-induced T cell activation). Additionally, the "effective amount" of a compound may vary depending on the desired result, for example, the level of T cell activation inhibition desired. The "therapeutically effective amount" necessary for inhibiting T cell proliferation may differ from the "therapeutically effective amount" necessary for preventing cytokine production.

The term, "agent", as used herein, refers to any natural or synthetic compound (i.e., for example, a peptide, a peptide variant, or a small molecule).

The term, "composition", as used herein, refers to any mixture of substances comprising a peptide and/or compound contemplated by the present invention. Such a composition may include the substances individually or in any combination.

The term, "intrinsic helicity", as used herein, refers to the helicity which is adopted by a peptide in an aqueous solution.

The term, "induced helicity", as used herein, refers to the helicity which is adopted by a peptide when in the presence of a helicity inducer, including, but not limited to, trifluoroethanol (TFE), detergents (i.e., for example, sodium dodecyl sulfate (SDS)), or lipids (i.e., for example, lipid vesicles (small lamilar vesicles (SUVs) and/or large lamilar vesicles (LUVs) as described herein).

The term "therapeutic drug", as used herein, refers to any pharmacologically active substance capable of being administered which achieves a desired effect. Drugs or compounds can be synthetic or naturally occurring, non-peptide, proteins or peptides, oligonucleotides or nucleotides, polysaccharides or sugars. Drugs or compounds may have any of a variety of activities, which may be stimulatory or inhibitory, such as antibiotic activity, antiviral activity, antifungal activity, steroidal activity, cytotoxic, cytostatic, anti-proliferative, anti-inflammatory, analgesic or anesthetic activity, or can be useful as contrast or other diagnostic agents.

The term "effective dose" as used herein refers to the concentration of any compound or drug contemplated herein that results in a favorable clinical response. In solution, an effective dose may range between approximately 1 ng/ml-100 mg/ml, preferably between 100 ng/ml-10 mg/ml, but more preferably between 500 ng/ml-1 mg/ml.

The term "administered" or "administering" a drug or compound, as used herein, refers to any method of providing a drug or compound to a patient such that the drug or compound has its intended effect on the patient. For example, one method of administering is by an indirect mechanism using a medical device such as, but not limited to a catheter, syringe etc. A second exemplary method of administering is by a direct mechanism such as, local tissue administration (i.e., for example, extravascular placement), oral ingestion, transdermal patch, topical, inhalation, suppository etc.

The term "anti-inflammatory drug" means any compound, composition, or drug useful for preventing or treating inflammatory disease.

The term "medical device", as used herein, refers broadly to any apparatus used in relation to a medical procedure. Specifically, any apparatus that contacts a patient during a medical procedure or therapy is contemplated herein as a medical device. Similarly, any apparatus that administers a drug or compound to a patient during a medical procedure or therapy is contemplated herein as a medical device. "Direct medical implants" include, but are not limited to, urinary and intravascular catheters, dialysis catheters, wound drain tubes, skin sutures, vascular grafts and implantable meshes, intraocular devices, implantable drug delivery systems and heart valves, and the like. "Wound care devices" include, but are not limited to, general wound dressings, non-adherent dressings, burn dressings, biological graft materials, tape closures and dressings, surgical drapes, sponges and absorbable hemostats. "Surgical devices" include, but are not limited to, surgical instruments, endoscope systems (i.e., catheters, vascular catheters, surgical tools such as scalpels, retractors, and the like) and temporary drug delivery devices such as drug ports, injection needles etc. to administer the medium. A medical device is "coated" when a medium comprising an anti-inflammatory drug (i.e., for example, a variant SARS-CoV fusion peptide) becomes attached to the surface of the medical device. This attachment may be permanent or temporary. When temporary, the attachment may result in a controlled release of a variant SARS-CoV fusion peptide.

The term "endoscope" refers to any medical device that is capable of being inserted into a living body and used for tasks including, but not limited to, observing surgical procedures, performing surgical procedures, or applying medium to a surgical site. An endoscope is illustrated by instruments including, but not limited to, an arthroscope, a laparoscope, hysteroscope, cytoscope, etc. It is not intended to limit the use of an endoscope to hollow organs. It is specifically contemplated that endoscopes, such as an arthroscope or a laparoscope is inserted through the skin and courses to a closed surgical site.

The term "vascular access site" is defined herein as referring to any percutaneous insertion of a medical device into the vasculature. For example, a hemodialysis catheter placement comprises a vascular access site. Such sites may be temporary (i.e., placed for a matter of hours) or permanent (i.e., placed for days, months or years).

The term "vascular graft" as used herein, refers to any conduit or portion thereof intended as a prosthetic device for conveying blood and, therefore, having a blood contacting surface (i.e., "luminal"). While usually in a tubular form, the graft may also be a sheet of material useful for patching portions of the circumference of living blood vessels (these materials are generally referred to as surgical wraps). Likewise, the term vascular graft includes intraluminal grafts for use within living blood vessels. The inventive grafts as such may also be used as a stent covering on the exterior, luminal or both surfaces of an implantable vascular stent.

The term "synthetic vascular graft" as used herein, refers to any artificial tube or cannula designed for insertion into a blood vessel. Such grafts may be constructed from polytetrafluoroethylene (PTFE).

The term "syringe" or "catheter" as used herein, refers to any device or apparatus designed for liquid administration, as defined herein. A syringe or catheter may comprise at least one storage vessel (i.e., for example, a barrel) wherein a single medium resides prior to administration. A syringe or catheter comprising two or more barrels, each containing a separate medium, may mix the media from each barrel prior to administration or the media of each barrel may be administered separately. One of skill in the art will recognize that any catheter designed to perform dialysis, as defined herein, may also administer liquids.

The term "dialysis/apheresis catheter" as used herein, refers to any multi-lumen catheter (i.e., for example, a triple lumen catheter) capable of providing a simultaneous withdrawal and return of blood to a patient undergoing a blood treatment process. Apheresis (called also pheresis) comprises a blood treatment process involving separation of blood elements that can remove soluble drugs or cellular elements from the circulation (Deisseroth et al., "Use Of Blood And Blood Products" in Cancer: Principles And Practice Of Oncology, Devita V. T. Jr. et al. Editors, Philadelphia: J. B. Lippincott Company 1989, 2045-59). For example, blood is withdrawn from a donor, some blood elements (i.e., for example, plasma, leukocytes, platelets, etc.) are separated and retained. The unretained blood elements are then retransfused into the donor.

The term "dialysis catheter" as used herein, refers to any device capable of removing toxic substances (impurities or wastes) from the body when the kidneys are unable to do so. A dialysis catheter may comprise a single catheter having at least a dual lumen (i.e., one lumen withdraws arterial blood and a second lumen returns the dialyzed blood to the venous system) or involve placing two catheters—one that is placed in an artery, and one in an adjacent vein. Dialysis catheters are most frequently used for patients who have kidney failure, but may also be used to quickly remove drugs or poisons in acute situations.

The term "peritoneal dialysis catheter" as used herein, refers to any continuous flow catheters with at least two lumens, one of which is a short lumen (used to infuse a dialysis solution into the peritoneum), and the other of which is a long coiled lumen having a plurality of openings, generally located on the inside of the coil. It is believed that peritoneal solutes enter into the coiled lumen openings and are thereby removed from the peritoneum. One hypothesis suggests that peritoneal dialysis works by using the peritoneal membrane inside the abdomen as the semipermeable membrane. Special solutions that facilitate removal of toxins may be infused in, remain in the abdomen for a time, and then drained out.

The term "fixed split-tip dialysis catheter" as used herein, refers to any catheter having at least two distinct elongated end portions that extend substantially parallel to the longitudinal axis of the catheter and are flexible to the lateral displacement of an infused fluid. It is believed that this flexibility prevents a permanent catheter tip splay that is known to injure tissue. Usually a fixed-tip dialysis catheter provides indwelling vascular access for patients undergoing long-term renal dialysis care (i.e., for example, end-stage renal disease).

The term "femoral catheter" as used herein, refers to any catheter that is inserted into the femoral vein. Femoral catheters are typically provided for intermediate term blood access because the superior vena cava is relatively close to the right atrium of the heart, the minimal range of shape changes of these veins with natural movements of the patient (to minimize the damage to the vessel intima), and because of good acceptance by the patients of the skin exit on the thoracic wall. Further, the femoral veins are easy to cannulate, so that catheters of this invention may be inserted into the femoral veins at the bed side.

The term "attached" as used herein, refers to any interaction between a medium (or carrier) and a therapeutic drug. Attachment may be reversible or irreversible. Such attachment includes, but is not limited to, covalent bonding, and non-covalent bonding including, but not limited to, ionic bonding, Van der Waals forces or friction, and the like. A drug is attached to a medium (or carrier) if it is impregnated, incorporated, coated, in suspension with, in solution with, mixed with, etc. The term "covalent bonding" as used herein, refers to an attachment between two compounds (I.e., for example, a medium and a drug) that comprising a sharing of electrons.

As used herein, the term "peptide" refers to linear or cyclic or branched compounds containing amino acids, amino acid equivalents or other non-amino groups, while still retaining the desired functional activity of a peptide. Peptide equivalents can differ from conventional peptides by the replacement of one or more amino acids with related organic acids such as p-aminobenzoic acid (PABA), amino acid analogs, or the substitution or modification of side chains or functional groups. Peptide equivalents encompass peptide mimetics or peptidomimetics, which are organic molecules that retain similar peptide chain pharmacophore groups as are present in the corresponding peptide. The term "peptide" refers to peptide equivalents as well as peptides. The amino acids can be in the L or D form so long as the binding function of the peptide is maintained.

As used herein, the term "cyclic peptide" refers to a peptide having an intramolecular bond between two non-adjacent amino acids. The cyclization can be effected through a covalent or non-covalent bond. Intramolecular bonds include, but are not limited to, backbone to backbone, side-chain to backbone and side-chain to side-chain bonds. As used herein, the term "dimer" as applied to peptides refers to molecules having two peptide chains associated covalently or non-covalently, with or without linkers. Peptide dimers wherein the peptides are linked C-terminus to N-terminus may also be referred to as "tandem repeats" or "tandem dimers." Peptide dimers wherein the peptides are linked C- to C-terminus, or N- to N-terminus may also be referred to as "parallel repeats" or "parallel dimers."

The term "placing" as used herein, refers to any physical relationship (i.e., secured or unsecured) between a patient's biological tissue and a surgical material, wherein the surgical material comprises a pharmaceutical drug that may be, optionally, attached to a medium. Such a physical relationship may be secured by methods such as, but not limited to, gluing, suturing, stapling, spraying, laying, impregnating, and the like. The term "parts by weight", as used herein, when used in reference to a particular component in a composition denotes the weight relationship between the component and any other components in the composition for which a pan by weight is expressed.

The term "protecting groups", as used herein, refer to those groups which prevent undesirable reactions (such as proteolysis) involving unprotected functional groups. In one embodiment, the present invention contemplates that the protecting group is an acyl or an amide. In one embodiment, the acyl is acetate. In another embodiment, the protecting group is a benzyl group. In another embodiment, the protecting group is a benzoyl group. The present invention also contemplates combinations of such protecting groups.

The term "protein", as used herein, refers to compounds comprising amino acids joined via peptide bonds and includes proteins and polypeptides; and may be an intact molecule, a fragment thereof, or multimers or aggregates of intact molecules and/or fragments; and may occur in nature or be produced, e.g., by synthesis (including chemical and/or enzymatic) or genetic engineering. The terms "protein" and "polypeptide" are used herein interchangeably.

As used herein, where "amino acid sequence" is recited herein to refer to an amino acid sequence of a protein molecule. An "amino acid sequence" can be deduced from the nucleic acid sequence encoding the protein. However, terms such as "polypeptide" or "protein" are not meant to limit the amino acid sequence to the deduced amino acid sequence, but include post-translational modifications of the deduced amino acid sequences, such as amino acid deletions, additions, and modifications such as glycolsylations and addition of lipid moieties.

The term "portion" when used in reference to a protein (as in "a portion of a given protein") refers to fragments of that protein. The fragments may range in size from four amino acid residues to the entire amino sequence minus one amino acid.

The term "analog", as used herein, includes any peptide having an amino acid sequence substantially identical to one of the sequences specifically shown herein in which one or more residues have been conservatively substituted with a functionally similar residue and which displays the abilities as described herein. Examples of conservative substitutions include the substitution of one non-polar (hydrophobic) residue such as isoleucine, valine, leucine or methionine for another, the substitution of one polar (hydrophilic) residue for another such as between arginine and lysine, between glutamine and asparagine, between glycine and serine, the substitution of one basic residue such as lysine, arginine or histidine for another, or the substitution of one acidic residue, such as aspartic acid or glutamic acid for another.

The term "conservative substitution", as used herein, also includes the use of a chemically derivatized residue in place of a non-derivatized residue provided that such peptide displays the requisite inhibitory function on T cells as specified herein. The term derivative includes any chemical derivative of the peptide of the invention having one or more residues chemically derivatized by reaction of side chains or functional groups.

The term "homolog" or "homologous" when used in reference to a polypeptide refers to a high degree of sequence identity between two polypeptides, or to a high degree of similarity between the three-dimensional structure or to a high degree of similarity between the active site and the mechanism of action. In a preferred embodiment, a homolog has a greater than 60% sequence identity, and more preferably greater than 75% sequence identity, and still more preferably greater than 90% sequence identity, with a reference sequence.

As applied to polypeptides, the term "substantial identity" means that two peptide sequences, when optimally aligned, such as, for example, by the programs SIM + LALNVIEW, LALIGN and DIALIGN (expasy.ch/tools) using default gap weights, share at least 80 percent sequence identity, preferably at least 90 percent sequence identity, more preferably at least 95 percent sequence identity or more (e.g., 99 percent sequence identity). Preferably, residue positions which are not identical differ by conservative amino acid substitutions.

The terms "variant" and "mutant" when used in reference to a polypeptide refer to an amino acid sequence that differs by one or more amino acids from another, usually related polypeptide. The variant may have "conservative" changes, wherein a substituted amino acid has similar structural or chemical properties. One type of conservative amino acid substitutions refers to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine. More rarely, a variant may have "non-conservative" changes (e.g., replacement of a glycine with a tryptophan). Similar minor variations may also include amino acid deletions or insertions (in other words, additions), or both. Guidance in determining which and how many amino acid residues may be substituted, inserted or deleted without abolishing biological activity may be found using computer programs well known in the art, for example, DNAStar software. Variants can be tested in functional assays. Preferred variants have less than 10%, and preferably less than 5%, and still more preferably less than 2% changes (whether substitutions, deletions, and so on).

It is understood by the person of ordinary skill in the art that the terms "CD3Z_HUMAN", "T cell receptor ζ subunit", "CD antigen CD247", "TCR ζ", "ζ signaling subunit" and "TCR ζ signaling chain" refer to the naturally occurring human protein listed in the UniProt Knowledgebase (UniProtKB, www.uniprot.org) under the name "CD3Z_HUMAN". The protein amino acid sequence can be found under the entry UniProt KB/Swiss-Prot P20963. It is further understood that the terms "CD3D_HUMAN", "CD antigen CD3d", "CD3 δ subunit", "CD3δ", "CD3δ signaling subunit" and "CD3δ signaling chain" refer to the naturally occurring human protein listed in the UniProt Knowledgebase (UniProtKB, www.uniprot.org) under the name "CD3D_HUMAN". The protein amino acid sequence can be found under the entry UniProt KB/Swiss-Prot P04234. It is still further understood that the terms "CD3G_HUMAN", "CD antigen CD3g", "CD3 γ subunit", "CD3γ", "CD3γ signaling subunit" and "CD3γ signaling chain" refer to the naturally occurring human protein listed in the UniProt Knowledgebase (UniProtKB, www.uniprot.org) under the name "CD3G_HUMAN". The protein amino acid sequence can be found under the entry UniProt KB/Swiss-Prot P09693. It is still further understood that the terms "CD3E_HUMAN", "CD antigen CD3e", "CD3 ε subunit", "CD3ε", "CD3ε signaling subunit" and "CD3ε signaling chain" refer to the naturally occurring human protein listed in the UniProt Knowledgebase (UniProtKB, www.uniprot.org) under the name "CD3E_HUMAN". The protein amino acid sequence can be found under the entry UniProt KB/Swiss-Prot P07766. It is still further understood that the terms "TCA_HUMAN", "T cell receptor alpha chain C region", "TCR α subunit", "TCRα", "TCRα ligand-binding subunit" and "TCRα ligand-binding chain" refer to the naturally occurring human protein listed in the UniProt Knowledgebase (UniProtKB, www.uniprot.org) under the name "TCA_HUMAN". The protein amino acid sequence can be found under the entry UniProt KB/Swiss-Prot P01848. It is still further understood that the terms "TCB_HUMAN", "T cell receptor beta chain C region", "TCR β subunit", "TCRβ", "TCRβ ligand-binding subunit" and "TCRβ ligand-binding chain" refer to the naturally occurring human protein listed in the UniProt Knowledgebase (UniProtKB, www.uniprot.org) under the name "TCB_HUMAN". The protein amino acid sequence can be found under the entry UniProt KB/Swiss-Prot P01850.

It is understood by the person of ordinary skill in the art that the terms "PP65_HCMVA", "65 kDa phosphoprotein", "65 kDa matrix phosphoprotein", "Tegument protein UL83", "Phosphoprotein UL83", "Cytomegalovirus pp 65 tegument protein", and "CMV pp65" refer to the naturally occurring protein of human cytomegalovirus listed in the UniProt Knowledgebase (UniProtKB, www.uniprot.org) under the name "PP65_HCMVA". The protein amino acid sequence can be found under the entry UniProt KB/Swiss-Prot P06725. It is further understood that the terms "SPIKE_CVHSA", "Spike glycoprotein", "human severe acute respiratory syndrome coronavirus", and "SARS CoV" refer to the naturally occurring spike glycoprotein of human human severe acute respiratory syndrome coronavirus listed in the UniProt Knowledgebase (UniProtKB, www.uniprot.org) under the name "SPIKE_CVHSA". The protein amino acid sequence can be found under the entry UniProt KB/Swiss-Prot P59594. It is still further understood that the terms "TIP_SHV2C", "Tyrosine-protein kinase-interacting protein", "tip", "herpesvirus saimiri", and "HVS Tip" refer to the naturally occurring tyrosine-protein kinase-interacting protein of herpesvirus saimiri listed in the UniProt Knowledgebase (UniProtKB, www.uniprot.org) under the name "TIP_SHV2C". The protein amino acid sequence can be found under the entry UniProt KB/Swiss-Prot P22575. It is still further understood that the terms "TIO_ATHV3", "Two-in-one protein", "protein tio", "herpesvirus ateles", and "HVA Tip" refer to the naturally occurring two-in-one protein of herpesvirus ateles listed in the UniProt Knowledgebase (UniProtKB, www.uniprot.org) under the name "TIO_ATHV3". The protein amino acid sequence can be found under the entry UniProt KB/Swiss-Prot Q9YJQ8. It is still further understood that the terms "ENV_HTL1A", "Envelope glycoprotein gp62", "Env polyprotein", "Human T cell leukemia virus 1 gp62", "Human T cell leukemia virus 1 gp21", and "HTLV-1 gp21" refer to the naturally occurring glycoprotein 21 of human T cell leukemia virus 1 listed in the UniProt Knowledgebase (UniProtKB, www.uniprot.org) under the name "ENV_HTL1A". The protein amino acid sequence can be found under the entry UniProt KB/Swiss-Prot P03381. It is still further understood that the terms "ENV_HV1H2", "Envelope glycoprotein gp160", "Env_polyprotein", "Human immunodeficiency virus type 1 gp41", "Human immunodeficiency virus type 1 gp41", "HIV-1 gp41", and "HIV gp41" refer to the naturally occurring glycoprotein 41 of human immunodeficiency virus type 1 listed in the UniProt Knowledgebase (UniProtKB, www.uniprot.org) under the name "ENV_HV1H2". The protein amino acid sequence can be found under the entry UniProt KB/Swiss-Prot P04578. It is further understood that the terms "GLYC_LASSJ", "Pre-glycoprotein polyprotein GP complex", "Lassa virus glycoprotein G2", and "LASV gp2" refer to the naturally occurring glycoprotein G2 of Lassa virus listed in the UniProt Knowledgebase (UniProtKB, www.uniprot.org) under the name "GLYC_LASSJ". The protein amino acid sequence can be found under the entry UniProt KB/Swiss-Prot P08669. It is still further understood that the terms "GLYC LYCVW", "Pre-glycoprotein polyprotein GP complex", "Lymphocytic choriomeningitis virus glycoprotein G2", and "LCMV gp2" refer to the naturally occurring glycoprotein G2 of Lymphocytic choriomeningitis virus listed in the UniProt Knowledgebase (UniProtKB, www.uniprot.org) under the name "GLYC_LYCVW". The protein amino acid sequence can be found under the entry UniProt KB/Swiss-Prot P07399. It is still further understood that the terms "GLYC_MOPEI", "Pre-glycoprotein polyprotein GP complex", "Mopeia virus glycoprotein G2", and "MOPV gp2" refer to the naturally occurring glycoprotein G2 of Mopeia virus listed in the UniProt Knowledgebase (UniProtKB, www.uniprot.org) under the name "GLYC_MOPEI". The protein amino acid sequence can be found under the entry UniProt KB/Swiss-Prot P19240. It is still further understood that the terms "GLYC_TACV", "Pre-glycoprotein polyprotein GP complex", "Tacaribe virus glycoprotein G2", "TCRV gp2", and "TACV gp2" refer to the naturally occurring glycoprotein G2 of Tacaribe virus listed in the UniProt Knowledgebase (UniProtKB, www.uniprot.org) under the name "GLYC_TACV". The protein amino acid sequence can be found under the entry UniProt KB/Swiss-Prot P18141. It is still further understood that the terms "CKS-17", "CKS-17 immunosuppressive domain", "Cas-Br-E murine leukemia virus immunosuppression region", "Envelope protein 15E", and "CKS-17, an mulv-related heptadecapeptide" refer to the naturally occurring immunosuppressive domain of murine leukemia virus listed in the UniProt Knowledgebase (UniProtKB, www.uniprot.org) under the name "ENV_MLVCB". The protein amino acid sequence can be found under the entry UniProt KB/Swiss-Prot P08360. It is still further understood that the terms "VGP_EBOSB", "Envelope glycoprotein", "Sudan Ebola virus glycoprotein 2", and "SEBOV gp2" refer to the naturally occurring glycoprotein 2 of Sudan Ebola virus listed in the UniProt Knowledgebase (UniProtKB, www.uniprot.org) under the name "VGP_EBOSB". The protein amino acid sequence can be found under the entry UniProt KB/Swiss-Prot Q66814. It is still further understood that the terms "VGP_EBOZM", "Envelope glycoprotein", "Zaire Ebola virus glycoprotein 2", and "ZEBOV gp2" refer to the naturally occurring glycoprotein 2 of Zaire Ebola virus listed in the UniProt Knowledgebase (UniProtKB, www.uniprot.org) under the name "VGP_EBOZM". The protein amino acid sequence can be found under the entry UniProt KB/Swiss-Prot Q05320. It is still further understood that the terms "VGP_MABVM", "Envelope glycoprotein", "Lake Victoria marburgvirus glycoprotein 2", "Marburg virus gp2", and "MARV gp2" refer to the naturally occurring glycoprotein 2 of Marburg virus listed in the UniProt Knowledgebase (UniProtKB, www.uniprot.org) under the name "VGP_MABVM". The protein amino acid sequence can be found under the entry UniProt KB/Swiss-Prot P35253. It is still further understood that the terms "ENV_MLVF5", "Envelope glycoprotein", "Envelope protein 15E", "Friend murine leukemia virus envelope glycoprotein", "FrMLV gp", and "Fr-MLV gp" refer to the naturally occurring envelope glycoprotein of Friend murine leukemia virus listed in the UniProt Knowledgebase (UniProtKB, www.uniprot.org) under the name "ENV_MLVF5". The protein amino acid sequence can be found under the entry UniProt KB/Swiss-Prot P03390. It is still further understood that the terms "U24_HHV6U", "Glycoprotein U24", "Human herpesvirus 6A glycoprotein U24", "HHV-6 glycoprotein U24", "HHV-6 EoLF1", and "HHV-6 U24" refer to the naturally occurring glycoprotein U24 of human herpesvirus 6A listed in the UniProt Knowledgebase (UniProtKB, www.uniprot.org) under the name "U24_HHV6U". The protein amino acid sequence can be found under the entry UniProt KB/Swiss-Prot Q69559.

DETAILED DESCRIPTION OF THE INVENTION

The present invention relates to peptides or fragments, homologs and derivatives thereof, which are derived from amino acid sequences of fusion and other protein regions of various viruses and from combinations thereof, and affect T cells by action on the activating T cell receptor (TCR). The present invention further relates to the treatment or prevention of various inflammatory and autoimmune disease states or other conditions where T cells are involved or recruited. In one embodiment, T cell receptor is inhibited by variant peptides binding to the transmembrane regions of the TCRζ and CD3δε subunits.

Various methods of application are proposed to use these protein variants including, but not limited to; i) treating T cell-related diseases or other medical conditions where T cells are involved or recruited; ii) drug delivery systems; iii) a sequence-based rational drug design method; iv) protease-resistance immunotherapeutic peptides; v) coatings of medical devices, such as implants and implantable devices.

The present invention contemplates constructing a series of variant peptides capable of reducing said T cell activation by action on the activating T cell receptor. TCR is a member of family of multichain immune recognition receptors (MIRRs) which are characterized by a common and distinct receptor architectural feature—their ligand-binding subunits and signaling subunits represent separate transmembrane protein chains that are noncovalently bound in the transmembrane milieu (A. B. Sigalov. *Trends Immunol.* 2004; 25:583-9; A. B. Sigalov. *Adv Exp Med Biol* 2008; 640:268-311; A. B. Sigalov. Adv Exp Med Biol 2008; 640:121-63; A. D. Keegan and Paul W. E. *Immunol Today* 1992; 13:63-68). The invariant TCR signaling chains, namely, CD3ε, δ, γ, and TCR ζ, all have a conserved single negative charge in their TM domains, while TM domains of the variant TCR α and β chains contain one (TCRβ) or two (TCRα) positive charges. Studies on the TCR assembly (Manolios et al. *Science* 1990; 249:274-7; Call et al. *Cell* 2002:111:967-79) showed that the integrity and functionally of the receptor is provided by TM electrostatic interactions. The positively charged amino acid residues (Lys and Arg) in the TM region of the TCRα chain interact with the negatively charged amino acid residues (Asp) of the TM domains of ζ homodimer (Asp) and CD3δε heterodimer whereas Lys in the TM domain of the TCRβ chain interacts with the negatively charged amino acid residues in the TM domains of CD3γ

(Glu) and CD3ε (Asp) chains of the CD3γε heterodimer. Recently, these interactions have been suggested as universal therapeutic targets for a diverse variety of T cell-related pathologies (A. B. Sigalov. *Trends Immunol.* 2004; 25:583-9; A. B. Sigalov. *Adv Exp Med Biol* 2007; 601:335-44). It has been also suggested that the molecular mechanisms targeting the TCR TM interactions underlie ability of different human viruses such as human immunodeficiency virus (HIV), cytomegalovirus (CMV), severe acute respiratory syndrome coronavirus (SARS-CoV) to modulate and/or escape the host immune response (A. B. Sigalov. *Trends Pharmacol Sci* 2006; 27:518-24; A. B. Sigalov. *Faseb J* 2007; 21:1633-34; A. B. Sigalov. *Adv Exp Med Biol* 2008; 640:268-311; W. M. Kim and A. B. Sigalov. *Adv Exp Med Biol* 2008; 640:325-49; A. B. Sigalov. *PLoS Pathog* 2009; 5:e1000404).

The TCR/CD3εδ/CD3εγ/ζζ-coupled antigen receptor signaling pathway resident within T cell membranes represents but one mechanism responsible for antigen-mediated T cell activation. Although it is not necessary to understand the mechanism of an invention, it is believed that these variant peptides insert themselves into the T cell membrane and act as a "receptor decoy" for antigen molecules. It is further believed that TCR triggering and subsequent cell activation requires the antigen-induced bridging of multiple TCRs that generates an intracellular activation signal by bringing membrane-embedded CD3ε, δ, γ, and TCR ζ signaling subunits into close proximity and proper (permissive orientation) to trigger the receptor. These peptide variants may prevent antigen-mediated T cell activation by reducing CD3ε, δ, γ, and TCR ζ aggregation by generating TCRζ/CD3δε/peptide variant bridges. It is further believed that the molecular basis for the prevention of T cell activation is based upon protein-protein interactions. It is still further believed that the molecular mechanisms of action of the peptides of the invention derived from amino acid sequences (or from combinations thereof) of fusion and other protein regions of various viruses, including but not limiting to, SARS-CoV, HTLV-1, HVA, HVS, LASV, LCMV, MOPV, TACV, CKS-17, SEBOV, ZEBOV, MARV, Fr-MLV and HHV-6, are used by the viruses in vivo to enter the T cell without triggering the self-defense response. It is further believed that viral immune evasion strategies can be transferred to therapeutic strategies that require similar functionalities. Viruses represent years of evolution and the efficiency and optimization that come along with it. It is still further believed that the viruses use their fusion and other immunosuppressive sequences to disrupt the protein-protein interactions the TCRα/CD3δε/ζζ signaling module of the T cell receptor responsible for alarming the cell of the presence of the intruder and, by doing so, blocks the receptor's ability to send the distress signal.

Protein-protein interactions are involved in most biological processes and thus represent an appealing target for innovative drug development. These interactions can be targeted by small molecule inhibitors, peptides, and peptidomimetics. Consequently, indirect protein therapy that alters protein-protein interactions represents an alternative to direct protein therapeutics (i.e., for example, immunotherapy) and avoids dangerous side effects. Indirectly acting peptides may serve as active regulators and participate in molecular cross talk, which drives metabolic processes. These indirectly acting peptides are also extremely potent, showing high specificity, and have few toxicological problems. Moreover, these indirectly acting peptides do not accumulate in organs or suffer from drug-drug interactions as many small molecules do. They can be used as therapeutic agents, or as a starting point for developing peptidomimetics and small molecular weight inhibitors.

I. T Cell Receptor-mediated T Cell Activation

Immune responses rely upon the detection of specific antigens by T cells, antigen exposure activating a T cell which possibly leads to cell proliferation and differentiation. The TCR is the central signaling pathway regulating T cell biology (K. R. Jerome *J Virol* 2008; 82:4194-204). This receptor allows the T cell to recognize antigen presented in the context of major histocompatibility complex (MHC) class I or class II molecules expressed on infected cells or professional antigen-presenting cells. TCR signaling in naive T cells drives their activation and expansion. In effector or memory T cells, TcR signaling drives expansion and triggering of effector functions, such as cytokine synthesis and cytotoxicity. The TCR-mediated activation process is complex and multifaceted, and despite decades of research remains controversial (Wedagedera et al. *Biophys J* 2006; 91:1604-18; A. B. Sigalov, ed, *Multichain Immune Recognition Receptor Signaling: From Spatiotemporal Organization to Human Disease*, Springer-Verlag, New York 2008).

T cell receptor is an attractive target for therapy of a variety of T cell-related pathologies (A. B. Sigalov, ed, *Multichain Immune Recognition Receptor Signaling: From Spatiotemporal Organization to Human Disease*, Springer-Verlag, New York, 2008). TCR is also critically important for the orchestration of the antiviral response and also for the direct killing of infected cells. Till recently, antibodies or fragments of antibodies have been considered as clinically significant therapeutic agents for various T cell-related diseases. For example, the use of antibodies is suggested (U.S. Pat. No. 6,221,352) to treat autoimmune disorders such as rheumatoid arthritis. However, antibody therapy poses serious disadvantages such as a potential contamination of antibody preparations by infectious agents such as prions or viruses, the high cost of developing and administering antibody therapies, inherent immunogenicity and other side effects. Other approach includes peptides based on TCR-derived sequences for disrupting TCR function (WO 96/22306; WO 97/47644; US Pat. Appl. 20050070478). Despite multiple advantages of these peptides as compared to antibodies, they have relatively low efficacy in terms of inhibiting TCR, thus having a high potential for toxicity and side effects.

Since among the cells of the immune system, T cells are critically important for the orchestration of the antiviral response and pose a threat to the successful evasion of viruses, and since TCR signaling is central to the development and function of T cells, it is not surprising that many viruses have evolved mechanisms to modulate TCR signaling. In this context, the ability viruses have developed over centuries of evolution to specifically affect TCR activation plays a crucial role in viral pathogenesis. Considering the efficiency and optimization of the viral T cell evasion strategy, it is very attractive to successfully transfer these highly effective and specific TCR-targeted viral approaches to therapeutic strategies that require similar functionalities.

The TCR-mediated activation signal can be divided into four parts: 1) the extracellular recognition of a multivalent antigen resulting in the aggregation, or clustering, of the TCRs, 2) TCR triggering and transmembrane (TM) signal transduction, 3) phosphorylation of the CD3ε, δ, γ, and TCR ζ Immunoreceptor Tyrosine-based Activation Motifs (ITAMs) by protein tyrosine kinases (PTKs) and activation of specific intracellular pathways, and 4) the activation of genes in the nucleus. The extracellular recognition of an antigen, the TCR-triggered biochemical cascades and the mechanisms of gene activation are understood in significant detail. However, despite extensive studies, the mechanism by which the TCR transduces ordered information such as antigen recognition from outside the cell via receptor TM and juxtamembrane (JM) regions into intracellular biochemical events (part 2), the mode of action of this clinically relevant peptide had not been elucidated until 2004 when a novel model of TCR signaling, the Signaling Chain HOmoOLigomerization (SCHOOL) model, was first introduced (A. B. Sigalov. *Trends Immunol.* 2004; 25:583-89), for the first time considering the TCR triggering and subsequent cell activation as a result of interplay between specific extracellular, transmembrane and intracellular protein-protein interactions.

II. SCHOOL Model of TCR Signaling

Figure 1B:
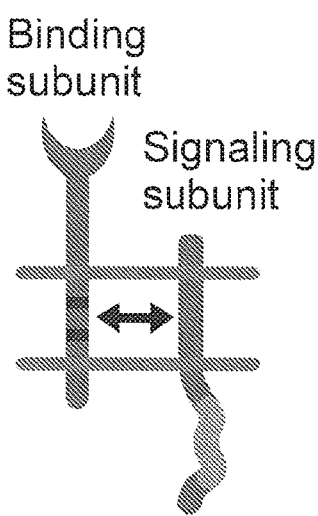
FIG. 1B presents a schematic representation of one possible structural and functional organization of MIRRs. Although it is not necessary to understand the mechanism of an invention, it is believed that transmembrane intersubunit heterointeractions between MIRR recognition and signaling components (shown by arrows) have a role in receptor assembly and integrity on resting cells. Curved lines depict disorder of the cytoplasmic domains of MIRR signaling subunits.

Multichain immune recognition receptors (MIRRs) expressed on various cells (See FIG. 1A) are believed to recognize foreign antigens and initiate many biological responses. Members of the MIRR family are believed to be multisubunit complexes that are formed by the noncovalent transmembrane association of recognition/binding subunits with signaling subunits (See, FIG. 1B). Therapeutic strategies contemplated herein involve MIRR triggering and subsequent transmembrane signaling. MIRR-mediated signal transduction, its role in health and disease, and the use of these receptors as attractive targets for rational drug design efforts in the treatment of several immune disorders are described in (US Pat. Appl. 20090075899; A. Sigalov. *Semin. Immunol.* 2005; 17:51-64; A. B. Sigalov. *Trends Immunol.* 2004; 25:583-89; A. B. Sigalov. *Trends Pharmacol Sci* 2006; 27:518-24; A. B. Sigalov. *Adv Exp Med Biol* 2007; 601:335-44; A. B. Sigalov. *Adv Exp Med Biol* 2008; 640:268-311) which are incorporated herein by reference in their entirety.

Figure 1C:
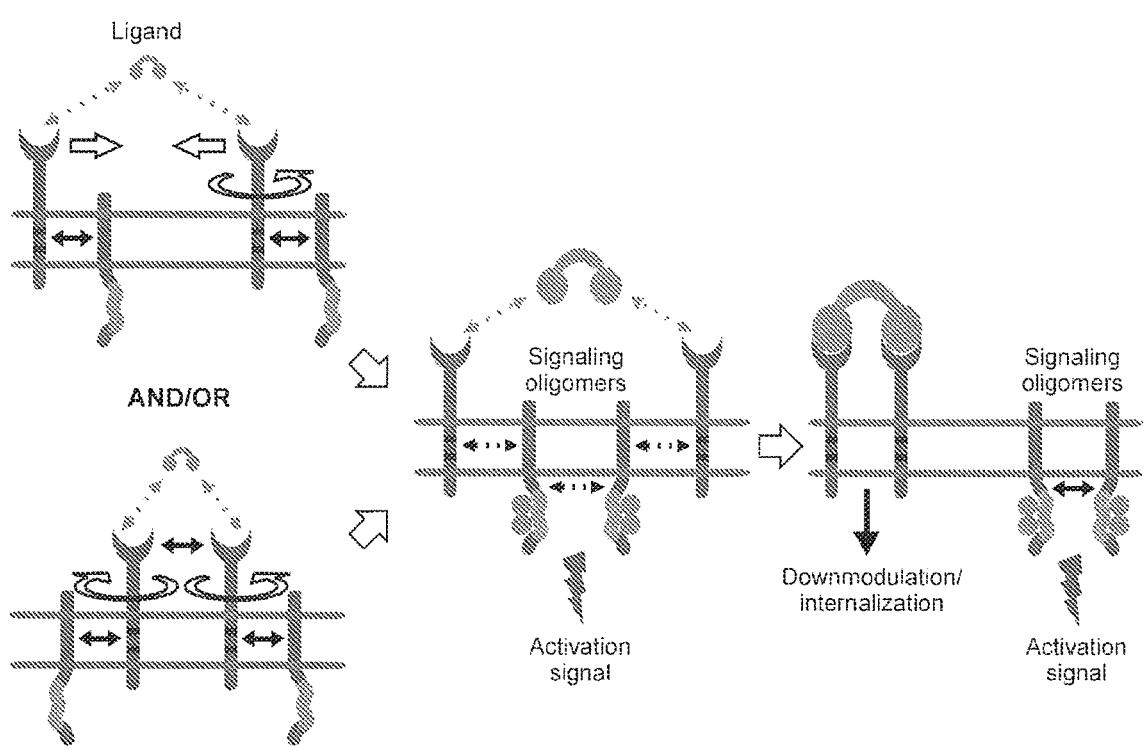
FIG. 1C illustrates one embodiment of a MIRR-mediated transmembrane signal transduction utilizing the Signaling Chain HOmoOLigomerization (SCHOOL) model. The model proposes that the homooligomerization of signaling subunits in the cytoplasmic milieu plays a key role in triggering MIRRs. Although it is not necessary to understand the mechanism of an invention, it is believed that ligand-induced MIRR clustering and reorientation (and/or receptor reorientation in preexisting MIRR clusters) lead to formation of a dimeric/oligomeric intermediate. It is further believed that in this intermediate, receptors are in sufficient proximity and adopt the correct (permissive) relative orientation and geometry to promote trans-homointeractions between cytoplasmic domains of signaling subunits resulting in formation of competent signaling oligomers. It still further believed that in these oligomers, protein tyrosine kinases phosphorylate the tyrosine residues in the ITAMs (green rectangles) or the YxxM motif of DAP-10 (blue rectangles), leading to the generation of activation signal(s), dissociation of signaling oligomers and internalization of the engaged MIRR ligand-binding subunits. Circular arrows indicate ligand-induced receptor reorientation. All interchain interactions in a dimeric intermediate are shown by dotted black arrows reflecting their transition state. Curved lines depict disorder of the cytoplasmic domains of MIRR signaling subunits. Phosphate groups are shown as dark circles. A similar general scheme can be considered for the pathway induced by receptor crosslinking, using antibodies to signaling subunits (e.g. anti-CD3e or anti-Igb antibodies for TCRs and BCRs, respectively). Abbreviations: ITAM, immunoreceptor tyrosine-based activation motif.
Figure 1D:
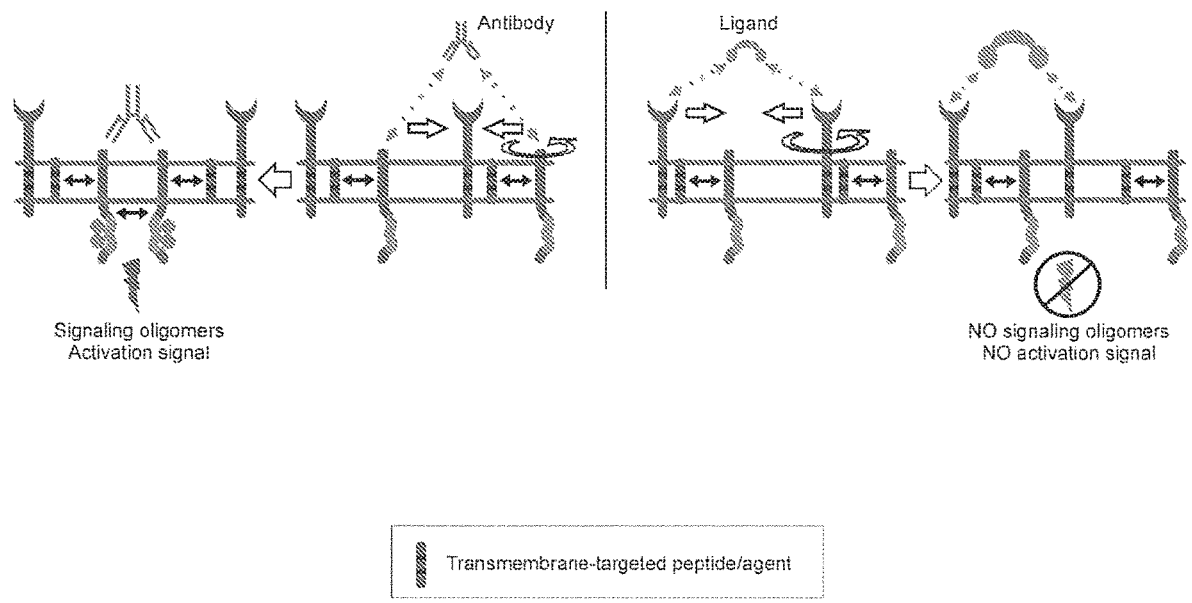
FIG. 1D illustrates one embodiment of a specific blockade or disruption of transmembrane interactions between recognition and signaling subunits resulting in a physical and functional disconnection of the MIRR subunits and "predissociation" of the receptor complex, thus preventing formation of signaling oligomers and inhibiting ligand-(right panel) but not antibody (left panel)-dependent immune cell activation.

In one embodiment, the present invention contemplates therapeutic targets compatible with a novel model of MIRR triggering and subsequent transmembrane signal transduction; the Signaling Chain HOmoOLigomerization (SCHOOL) model (See FIG. 1C) (A. B. Sigalov. *Adv Exp Med Biol* 2008; 640:268-311; A. B. Sigalov. *Adv Exp Med Biol* 2008; 640:121-63). Although it is not necessary to understand the mechanism of an invention, it is believed that the structural similarity of the MIRRs provides the basis for the similarity in the mechanisms of MIRR-mediated signaling. It is also believed that the model reveals MIRR transmembrane interactions as new therapeutic targets (See FIG. 1D). It is further believed that a general pharmaceutical approach based upon this SCHOOL model can be used to treat diverse immune-mediated diseases.

Figure 2:
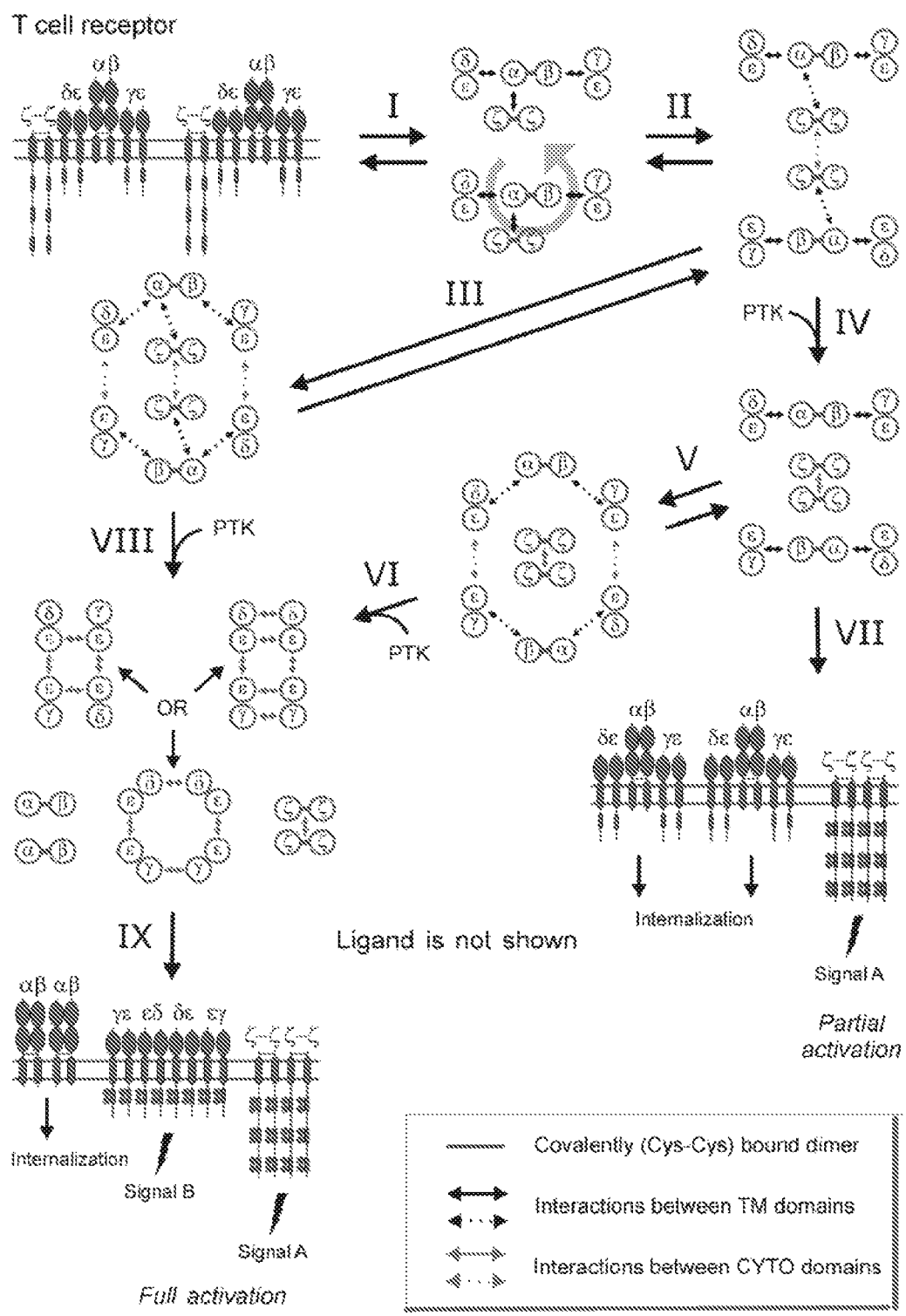
FIG. 2 illustrates one embodiment of the SCHOOL-based molecular mechanisms of T cell receptor (TCR) signaling. Immunoreceptor tyrosine-based activation motifs (ITAMs) are shown as gray rectangles. TCR-CD3-ζ components are represented as whole polypeptides and as a simplified axial view. All interchain interactions in intermediate complexes are shown by dotted arrows reflecting their transition state. Circular arrow indicates ligand-induced receptor reorientation. Interaction with multivalent ligand (not shown) clusters the receptors and pushes them to reorientate (I) and bring signaling subunits into a correct relative orientation and in sufficient proximity in the formed receptor oligomer (for illustrative purposes, receptor dimer is shown), thus starting the trans-homointeractions between ζ molecules (II). Then, two alternative pathways can take a place depending on the nature of activating stimuli. First is going through a stage IV resulting in formation of $\zeta_2$ dimer (dimer of dimers) and phosphorylation of the ζ ITAM tyrosines, thus triggering downstream signaling events. Then, the signaling ζ oligomers formed subsequently dissociate from the TCR-CD3 complex, resulting in internalization of the remaining engaged TCR-CD3 complexes (VII). This pathway leads to partial (or incomplete) T cell activation. Alternatively, the intermediate complex formed at the stage II can undergo further rearrangements, starting trans-homointeractions between CD3 proteins (III) and resulting in formation of an oligomeric intermediate. Again, the stages I, II and III can be reversible or irreversible depending on interreceptor proximity and relative orientation of the receptors in TCR dimers/oligomers as well as on time duration of the TCR-ligand contact and lifetime of the receptor in TCR dimers/oligomers that generally correlate with the nature of the stimulus and its specificity and affinity/avidity. Next, in the signaling oligomers formed (III), the ITAM tyrosines undergo phosphorylation by PTKs that leads to generation of the activation signal, dissociation of signaling oligomers and internalization of the remaining engaged TCRαβ chains (VIII, XI). This pathway provides at least two different activation signals from the ζ and CD3 signaling oligomers (signals A and B), respectively, and results in full T cell activation. The distinct signaling through ζ and CD3 oligomers (or through various combinations of signaling chains in CD3 oligomeric structures) might be also responsible for distinct functions such as T cell proliferation, effector functions, T cell survival, pathogen clearance, TCR anergy, etc. In addition, the signaling oligomers formed can sequentially interact with the signaling subunits of nonengaged TCRs resulting in formation of higher-order signaling oligomers, thus amplifying and propagating the activation signal (not shown). Also, this leads to the release and subsequent internalization of the remaining nonengaged TCR complexes and/or TCRαβ chains (not shown). Abbreviations: PTK, protein tyrosine kinase. Phosphate groups are shown as filled gray circles.
Figure 3:
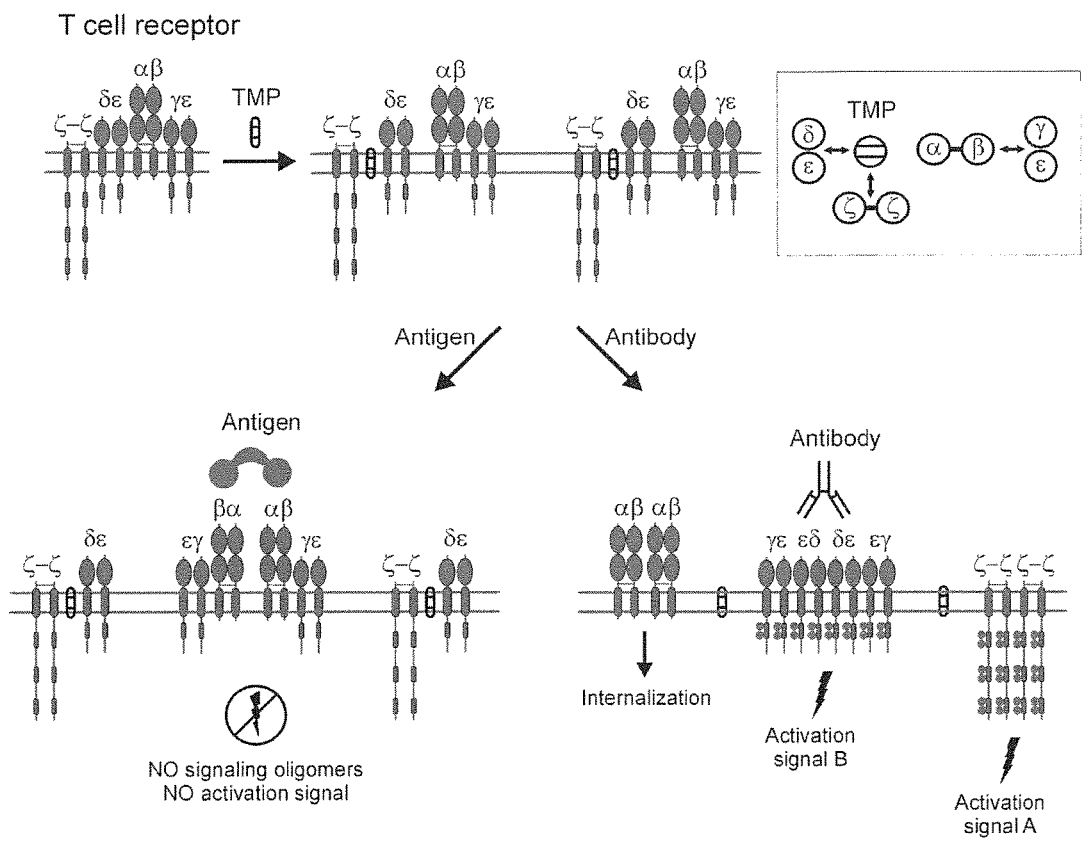
FIG. 3 illustrates one embodiment of the SCHOOL-based mechanisms of action of T cell receptor transmembrane inhibitors such as the T cell receptor core peptide (CP) and HIV-1 gp41 fusion peptide (FP). Considering the close similarity in patterns of inhibition of T cell activation and immunosuppressive activity observed for CP and FP, the SCHOOL model reasonably suggests a similar molecular mechanism of action for both peptides. Within the SCHOOL model, these peptides compete with the TCRα chain for binding to the CD3δε and ζ signaling subunits, thus disrupting the transmembrane (TM) interactions between these subunits and resulting in disconnection and predissociation of the relevant signaling subunits from the remaining receptor complex (also shown in the inset as a simplified axial view). This prevents formation of signaling oligomers upon multivalent antigen stimulation, thus inhibiting antigen-mediated T cell activation. In contrast, stimulation of these "predissociated" MIRRs with cross-linking antibodies to signaling subunit should still lead to receptor triggering and cell activation. The model predicts that the same mechanisms of inhibitory action can be applied to TCR TM peptides corresponding to the TM regions of not only the TCRαβ recognition subunits but the corresponding CD3ε, CD3δ, CD3γ and ζ signaling subunits as well. Abbreviations: TMP, transmembrane peptide.
Figure 4:
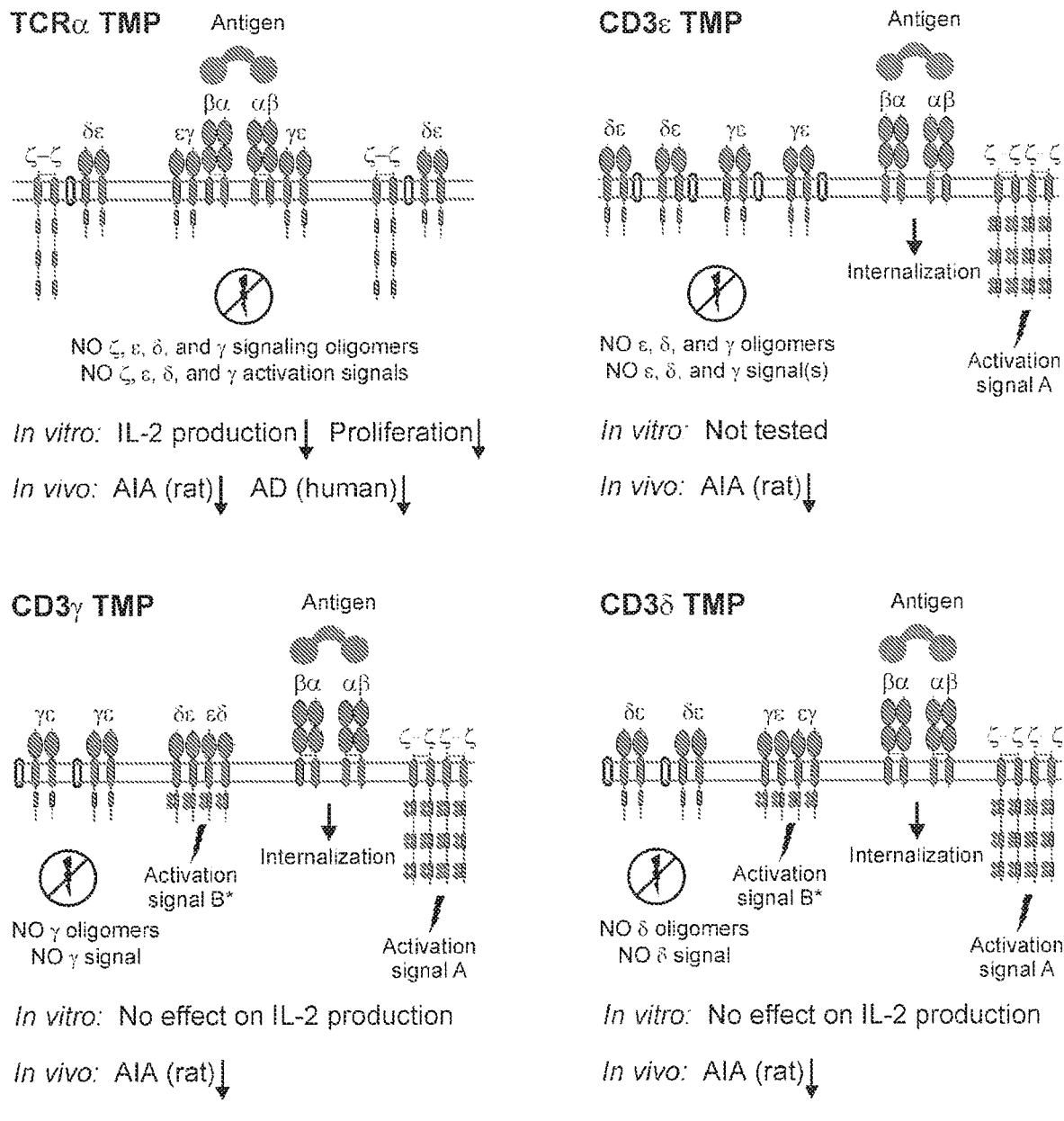
FIG. 4 illustrates one embodiment of the SCHOOL-based mechanisms of action of different T cell receptor transmembrane inhibitors. Within the SCHOOL model, upon antigen stimulation of T cells, T cell receptor α-chain (TCRα) transmembrane peptide (TMP) prevents formation of all signaling oligomers, including ζ, CD3ε, CD3δ, and CD3γ. This inhibits T cell activation in both in vitro and in vivo. In contrast, other TMPs prevent formation of signaling oligomers (and therefore signaling) of selected signaling subunits. This inhibits T cell activation in vivo whereas inhibition in vitro depends on the evaluation method used. Abbreviations: AD, atopic dermatitis; AIA, adjuvant-induced arthritis; IL-2, interleukin 2.
Figure 6A:
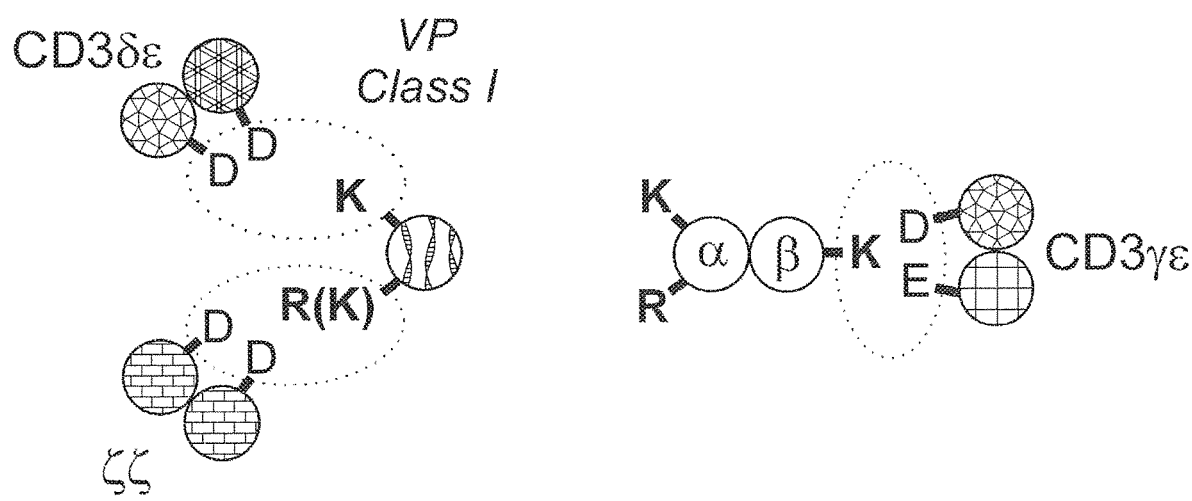
FIG. 6A illustrates one embodiment of the SCHOOL-based mechanisms of action of the Class I of TCR peptide inhibitors in the transmembrane milieu. Helices of the transmembrane domains of T cell receptor (TCR) α and β chains, TCR ζ chain, CD3 ε, γ, and δ chains, as well as of the transmembrane peptide inhibitors of the present invention are shown as a simplified axial view of helical wheels. Although the three-dimensional structures of the inhibitors of the invention within the cell membrane are not known, it might be assumed that these sequences may adopt a helical conformation upon membrane binding. Abbreviations: VP, viral peptide.
Figure 6B:
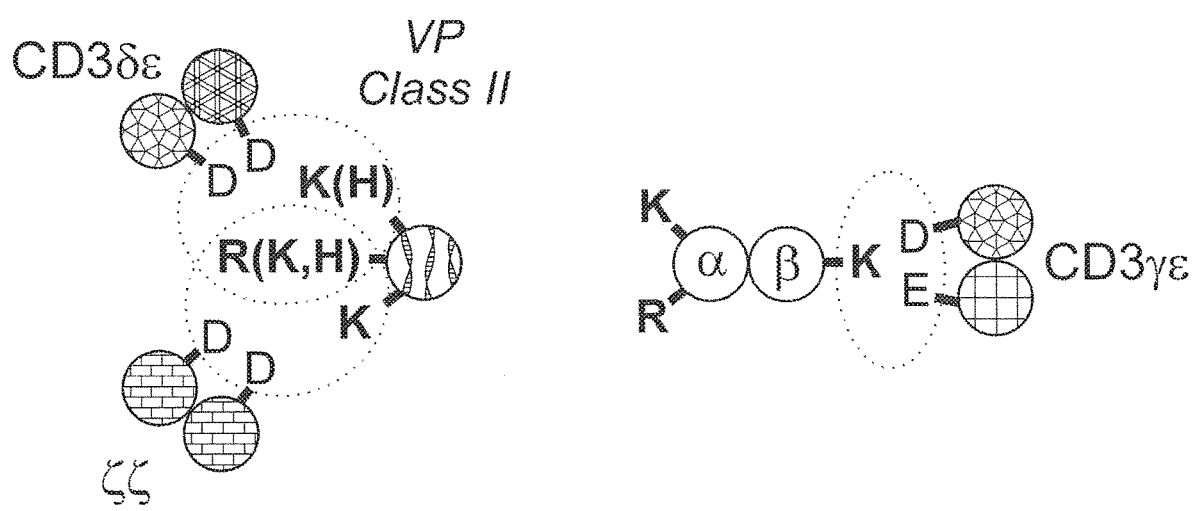
FIG. 6B illustrates one embodiment of the SCHOOL-based mechanisms of action of the Class II of TCR peptide inhibitors in the transmembrane milieu. Helices of the transmembrane domains of T cell receptor (TCR) α and β chains, TCR ζ chain, CD3 ε, γ, and δ chains, as well as of the transmembrane peptide inhibitors of the present invention are shown as a simplified axial view of helical wheels. Although the three-dimensional structures of the inhibitors of the invention within the cell membrane are not known, it might be assumed that these sequences may adopt a helical conformation upon membrane binding. Abbreviations: VP, viral peptide.
Figure 6C:
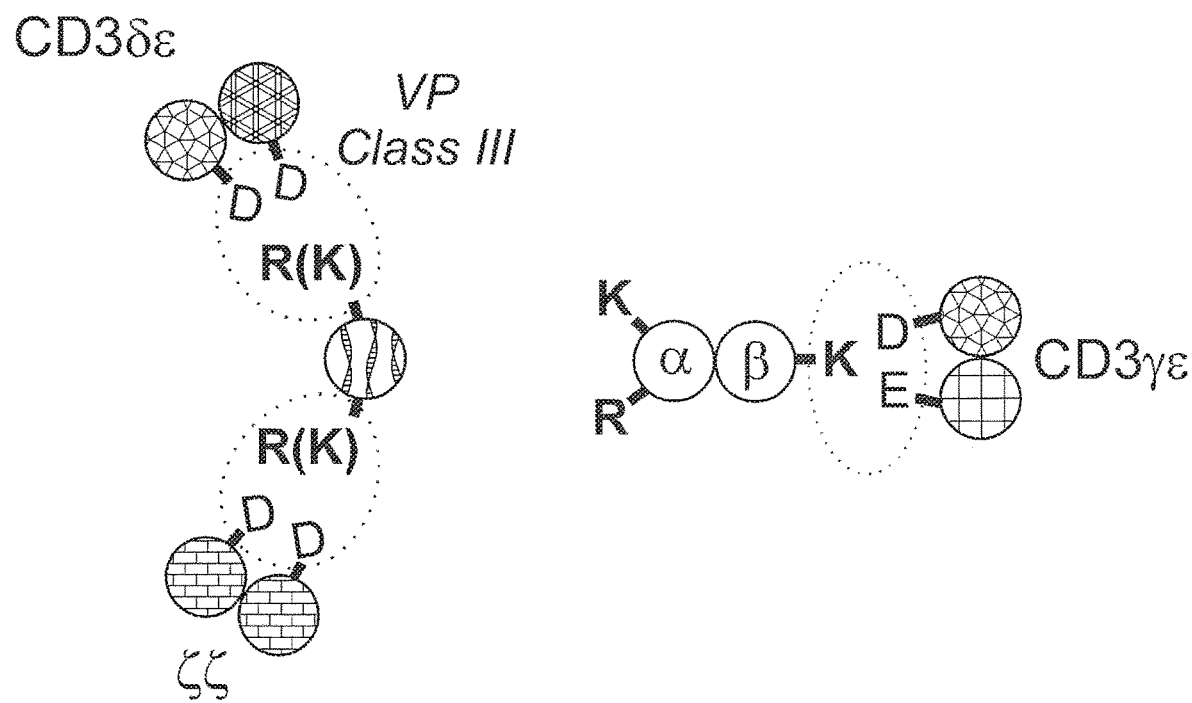
FIG. 6C illustrates one embodiment of the SCHOOL-based mechanisms of action of the Class III of TCR peptide inhibitors in the transmembrane milieu. Helices of the transmembrane domains of T cell receptor (TCR) α and β chains, TCR ζ chain, CD3 ε, γ, and δ chains, as well as of the transmembrane peptide inhibitors of the present invention are shown as a simplified axial view of helical wheels. Although the three-dimensional structures of the inhibitors of the invention within the cell membrane are not known, it might be assumed that these sequences may adopt a helical conformation upon membrane binding. Abbreviations: VP, viral peptide.

Application of the SCHOOL model to the transmembrane signal transduction mediated by a T cell antigen receptor (TCR) (See FIG. 2) reveals the TCRα/CD3εδ/ζζ transmembrane interactions as therapeutic targets and suggests that an inhibition of TCR signaling may be achieved by using transmembrane-targeted agents which specifically disrupt transmembrane interactions between the TCRα binding subunit and the CD3εδ and ζζ signaling subunits. For example, the simplest agents would be synthetic transmembrane peptides (TMPs) corresponding to the TCRα transmembrane domain (See FIG. 3). This mechanism explains surprising similarities in characteristics and immunomodulatory activities of the T cell receptor core peptide (CP) and HIV-1 gp41 fusion peptide (See TABLE 1) (Amon et al. *Biochim Biophys Acta* 2006; 1763:879-88; Wang et al. *Cell Immunol* 2002; 215:12-19; Wang et al. *Clin Immunol* 2002; 105:199-207; Quintana et al. *J Clin Invest* 2005; 115:2149-58). The SCHOOL mechanism of TCR signaling also suggest the molecular explanation of apparent discrepancies in the observed apparent discrepancy in inhibitory activity of different CD3 transmembrane peptides between in vitro and in vivo T cell inbition (See FIG. 4) (Collier et al. *Scand J Immunol* 2006; 64:388-91; A. B. Sigalov. *Adv Exp Med Biol* 2007; 601:335-44; A. B. Sigalov. *Adv Exp Med Biol* 2008; 640:121-63).

TABLE 1

Similarities in characteristics and immunomodulatory activities of the T cell receptor core peptide and HIV-1 gp41 fusion peptide

| Characteristics/Activation Model | CP | FP |
|---|---|---|
| Colocalization with TCR | + | + |
| Coprecipitation with TCR | + | + |
| Immunosuppressive activity in vivo | + | + |
| Inhibition of in vitro activation: | | |
| antigen | + | + |
| anti-TCRβ antibody | − | ND |
| anti-CD3 antibody | − | − |
| PMA/ionomycin | − | − |

Abbreviations: TCR, T cell receptor; CP, core peptide; FP, fusion peptide; PMA, phorbol 12-myristate 13-acetate; ND, not determined.

Without being limited by a particular theory, the basic principles of one proposed mechanism by which peptides and other compound of the present invention may work by TCR-mediated transmembrane signaling. See, FIGS. 2 & 3.

It is believed that multivalent antigen-induced clustering of a TCRαβ/CD3εδ/CD3εγ/ζζ receptor complex leads to formation of the relevant CD3ε, CD3δ, CD3 γ and ζ signaling oligomers with subsequent phosphorylation of the ITAM-Tyr residues and transmembrane transduction of the T cell activation signal. See, FIG. 2. This hypothesis suggests that a TCR Core Peptide (TCR-CP), a peptide corresponding to the transmembrane region of TCRα, penetrates the cell membrane and competitively binds to the transmembrane domain of heterodimeric CD3εδ and homodimeric ζζ signaling signaling subunits, thus displacing a TCRα chain from interacting with these signaling subunits, thereby resulting in a "pre-dissociation" of a TCRαβ/CD3εδ/CD3εγ/ζζ receptor complex. As a consequence, antigen (but not antibody)-induced TCR clustering does not lead to formation of CD3εδ, CD3εγ and homodimeric ζζ signaling oligomers and subsequent T cell activation. See, FIG. 3. This is the only mechanism that explains the observed characteristics and immunomodulatory activity features of the TCR CP and HIV-1 gp41 FP. See, TABLE 1.

Normal transmembrane (TM) interactions between the ligand-binding TCRα subunit and the CD3εδ and ζζ signaling subunits forming a functional TCRαβ/CD3εδ/CD3εγ/ζζ receptor complex comprise two positively charged amino acid residues (Lys and Arg) within the TCRα transmembrane portion and negatively charged aspartic acid pairs in the transmembrane domains of the CD3εδ heterodimer and ζζ homodimer, thereby allowing subunit association (Call et al. *Cell* 2002; 111:967-79). Although it is not necessary to understand the mechanism of an invention, it is believed that interactions between positively charged amino acids of a viral sequence-based peptide inhibitors of the invention and aspartic acid residues of the CD3εδ heterodimer and ζζ homodimer disrupt the transmembrane interactions between the TCRα subunit and the CD3εδ and ζζ signaling subunits, thereby "disconnecting" TCRα and result in a non-functioning T cell receptor. See FIGS. 3, 6A, 6B, and 6C.

III. T Cell Receptor Inhibitory Peptides of Viral Origin and Variants Thereof Although it is not necessary to understand the mechanism of an invention, it is believed that a hydrophobic/polar/charged amino acid sequence patterning, rather than sequence similarity, within a TCR inhibitory viral sequence plays a dominant role in the development of effective peptide-based inhibitors of T cell activation. For example, despite the lack of sequence similarity (See FIGS. 3 and 5), the fusion peptide (FP) in the N terminus of the HIV envelope glycoprotein, gp41, has been shown to inhibit T cell antigen receptor (TCR)-mediated T cell activation in vitro and in vivo more effectively than the transmembrane TCR core peptide (CP) with 100-fold lower the 50% inhibitory concentration (IC50) values for FP than those observed for CP.

In some embodiments, as contemplated by the present invention, optimal peptide inhibitors and peptide inhibitor analogues are designed using hydrophobic/polar/charged sequence pattern criteria and associated evaluation techniques. These criteria and techniques are described in (US Pat. Appl. 20090075899) and incorporated herein by reference in their entirety. The peptide inhibitors of the present invention may then be synthesized and tested in T cell function inhibition assays.

Listed in FIG. 5 are viral fusion and other sequences with known or unknown immunomodulatory activity. As surprisingly found, charge distribution patterns for fusion and other protein regions of various viruses are conserved in many unrelated viruses and show similarities to those for TCR CP and HIV FP which are known to exhibit TCR inhibitory activity. Exploratory investigation of the sequences listed reveals three major classes of the charge distribution patterns. Class I and Class III are characterized by two positively charged residues spaced apart by 4 and 8 amino acids, respectively, whereas Class II is characterized by three positively charged residues spaced apart by 3 amino acids. Within the SCHOOL model of TCR signaling, a striking similarity in the charge distribution patterns suggests a similarity in their mode of action (A. B. Sigalov. *PLoS Pathog* 2009; 5:e1000404). See FIGS. 6A, 6B, and 6C. This clearly demonstrates that different viruses have adopted similar mechanisms of specifically targeting TCR, disrupting receptor architecture and suppressing the immune system. Importantly, by virtue of the acquired insight into this conserved structural motif, expanded predictions, hypotheses and conclusions can be derived to being answering the question of if shared TCR-targeted strategies represents a conserved function or if it represents a convergent tactic of divergent viruses.

The transmembrane regions of the TCRα, CD3ε, CD3δ, and ζ chains are highly conserved and the substitutions between species are very conservative. This suggests a functional role for the transmembrane regions of TCRα, CD3ε, CD3δ, and ζ constituents of the TCR complex. These regions strongly interact between themselves, thus maintaining the integrity of the TCR signaling complex in resting cells. These transmembrane domains are short and should be easily mimicked by synthetic peptides and compounds of the invention derived from the listed fusion and other proteins of various viruses. Based on these features, and taking advantage of the SCHOOL model of TCR signaling to explain TCR-mediated cell activation, the present invention contemplates a new approach of intervening and modulating TCR function using a billion year-long drug development process of nature. In some embodiments, synthetic peptides and compounds are contemplated that may provide successful treatment options in the clinical setting.

In one embodiment, the present invention contemplates a series of peptides that are inhibitors of a TCR. Although it is not necessary to understand the mechanism of an invention, it is believed that this inhibition is mediated by disrupting the transmembrane interactions between the recognition, TCRα, and signaling subunits, namely CD3ε, CD3δ, and ζ. In other embodiments, these peptide inhibitors treat and/or prevent diseases and/or conditions comprising T cell activation. In one embodiment, the peptide inhibitors mediate antigen-induced T cell activation. In another embodiment, the present invention contemplates a drug delivery system comprising peptide inhibitors of the present invention. Although it is not necessary to understand the mechanism of an invention, it is believed that the peptide inhibitor drug delivery system functions by penetrating the T cell membrane.

Sequence-based rational design can be used as a tool in order to increase the effectiveness of the peptides to inhibit the function of the TCRαβ/CD3εδ/CD3εγ/ζζ receptor complex. Principles and techniques of a sequence-based rational design are described in (US Pat. Appl. 20090075899) and incorporated herein by reference in their entirety. For example, a conservative amino acid substitution of arginine for lysine or insertion of at least one supplemental positively charged amino acid residue (i.e., for example, arginine and/or lysine) may be made in certain locations on alpha-helixes of the peptides of the present inventions. Although it is not necessary to understand the mechanism of an invention, it is believed that these changes should result in increased binding activity to the transmembrane domains of the CD3εδ and ζζ receptor complex signaling subunit dimers, thus enhancing the effectiveness of the peptides to inhibit the function of TCR.

TCR peptide inhibitors and variants thereof contemplated herein may be modified at the carboxy terminal without loss of activity. Accordingly, it is intended that the present invention includes within its scope, peptides which include additional amino acids to the "core" sequence of the peptide of the present invention and which affect the interaction of TCRαβ, CD3εδ and ζζ subunits of the TCR signaling complex.

In some embodiments, the peptide inhibitors comprise D-stereoisomeric amino acids, thereby allowing the formation of immunotherapeutic peptides with increased resistance to protease degradation. In one embodiment, the D-amino acid peptide inhibitors are used for the clinical treatment in T cell-mediated disorders. Although it is not necessary to understand the mechanism of an invention, it is believed that these peptide inhibitors prevent T cell activation.

In some embodiments, the present invention contemplate peptide inhibitors that are protease resistant. In one embodiment, such protease-resistant peptide inhibitors are peptides comprising protecting groups. For example, a peptide peptide may be protected from exoproteinase degradation by N-terminal acetylation ("Ac") and/or C-terminal amidation.

In some embodiments, the peptide inhibitors comprise conjugated lipids and/or sugars. In other embodiments, the peptide inhibitors comprise hydrophobic amino acid motifs, wherein said motifs are known to increase the membrane penetrating ability of peptides and proteins. Although it is not necessary to understand the mechanism of an invention, it is believed that either lipid/sugar conjugation and/or hydrophobic amino acid motifs increase the efficacy TCR antigen receptor complex inhibition using the peptides and compositions of the invention.

In some embodiment, the peptides and compounds contemplated by the present invention may be used for production of peptide/compound-containing medical devices for local anti-inflammatory therapy and/or for the prevention of immune response.

IV. Classes of Transmembrane Peptide Variant TCR Inhibitors

The present invention described herein relates to synthetic peptides of viral origin and derivatives thereof, which may be useful in the clinical treatment and/or prevention of T cell-mediated disorders.

Figure 7:
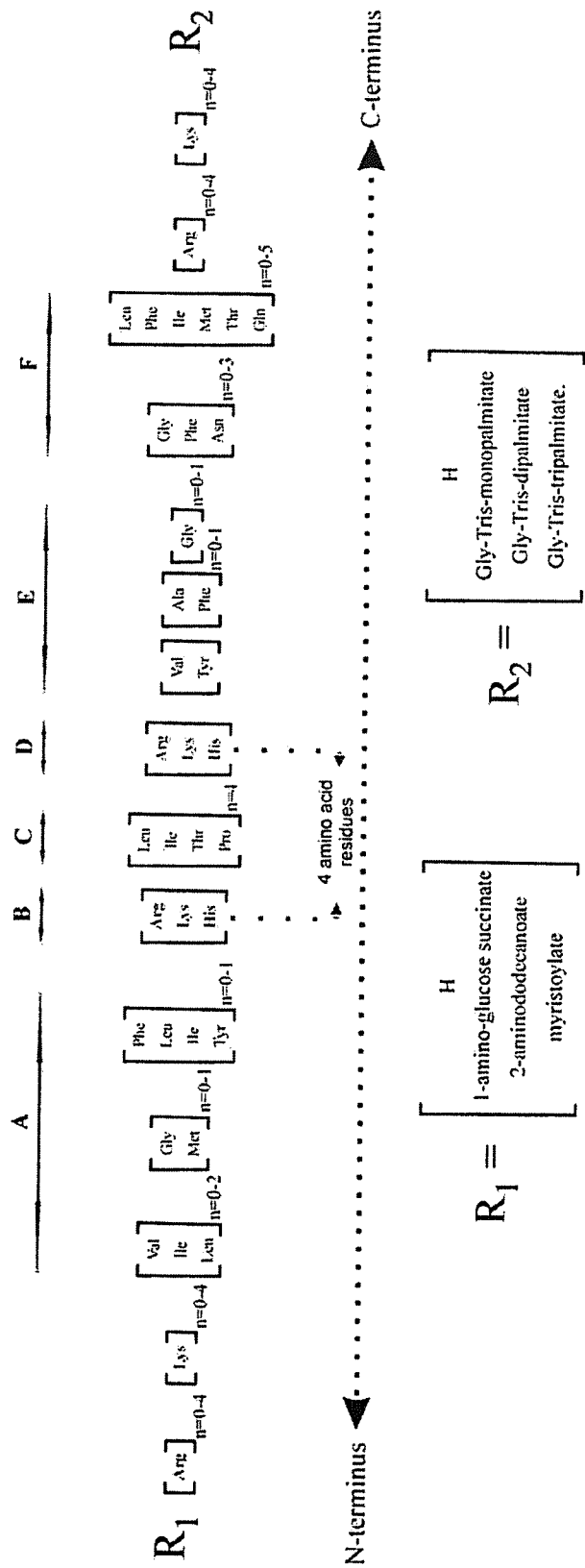
FIG. 7 presents various embodiments of the Class I of TCR peptide inhibitor sequences based upon a general formula, wherein in the general formula describes variants of the parent sequence of SARS-CoV FP.

In one embodiment, the present invention contemplates a Class I peptide derivative having the general formula $R_1$-A-B-C-D-E-F-$R_2$ (SEQ ID NO: 84) (See FIG. 7), or a di-sulfide bridged, linear dimer thereof, or a cyclic dimer thereof, wherein;

A is absent, or 1-4 D- or L-amino acids selected from the group including, but not limited to, Val, Ile, Leu, Gly, Met, Tyr, and Phe;

B is a positively charged D- or L-amino acid;

C is a peptide comprising 4 hydrophobic D- or L-amino acids, or Thr and 3 hydrophobic D- or L-amino acids, including D- or L-cysteine or a D- or L-cysteine homologue;

D is a positively charged D- or L-amino acid;

E is Val or Tyr, and 1-2 D- or L-amino acids selected from the group including, but not limited to, Ala, Phe, and Gly following Val or Tyr;

F is absent or 0 to 8 D- and L-amino acids selected from the group including, but not limited to, Gly, Phe, Asn, Leu, Ile, Met, Thr and Gln;

$R_1$ is absent (i.e., for example, —H) or 1-amino-glucose succinate, 2-aminododecanoate, or myristoylate; and $R_2$ is absent (i.e., for example, —H) or Gly-Tris-monopalmitate, -dipalmitate and -tripalmitate.

In some embodiments, peptide derivatives are created wherein (SEQ ID NO: 85);

A is a peptide comprising 1-4 amino acids selected from the group comprising Gly, Tyr, Cys, Val, Leu, Ile, and Met;

B is selected from Arg, His or Lys;

C is a peptide comprising 4 amino acids selected from the group comprising Leu, Ile, Thr, and Pro;

D is selected from Arg, His or Lys;

E is a peptide comprising 3 amino acids selected from the group comprising Val, Tyr, Ala, Phe, and Gly; and F is a peptide comprising 8 amino acids selected from the group comprising Gly, Phe, Asn, Leu, Ile, Met, Thr and Gln.

In one embodiment, the present invention contemplates a peptide derivative having the general formula $R_1$-[Arg and/or Lys]$_{n=0-4}$-A-B-C-D-E-F-[Arg and/or Lys]$_{n=0-4}$-$R_2$ or a di-sulfide bridged, linear dimer thereof, or a cyclic dimer thereof, wherein (SEQ ID NO: 86);

A may be i) absent; or ii) 1-4 amino acids selected from the group including, but not limited to, Val, Ile, Leu, Gly, Met, Phe, or Tyr;

B may be selected from the group including, but not limited to, Arg, Lys, or His;

C is 4 amino acids selected from the group including, but not limited to, Leu, Ile, Thr, or Pro;

D may be selected from the group including, but not limited to, Arg, Lys, or His;

E may be i) Val or Tyr; or ii) Val or Tyr and 1-2 amino acids selected from the group including, but not limited to, Ala, Phe, or Gly;

F may be i) absent or ii) 1-8 amino acids selected from the group including, but not limited to, Gly, Phe, Asn, Leu, Ile, Met, Thr and Gln.

$R_1$ and $R_2$ may be either i) absent; ii) a conjugated lipid selected from the group including, but not limited to, Gly-Tris-monopalmitate, -dipalmitate and -tripalmitate; or iii) a conjugated sugar selected from the group including, but not limited to, 1-amino-glucose succinate, 2-aminododecanoate, or myristoylate. See, FIG. 7.

As referred to herein, hydrophobic amino acids include, but are not limited to, Ala, Val, Leu, Ile, Pro, Phe, Trp, and Met; positively charged amino acids include, but are not limited to, Lys, Arg and His; and negatively charged amino acids include, but are not limited to, Asp and Glu.

The above general formula represents one embodiment of Class I of TCR peptide inhibitory sequences of viral origin (for example, SARS-CoV fusion peptide, FP; See FIG. 5) comprising at least one conserved domain that contains a highly homologous sequence between this sequence and the TCRα transmembrane domain. In one embodiment, a SARS-CoV FP-derived TCR inhibitory peptide comprises MYKTPTLKYFGGFNFSQIL (SEQ ID NO: 6) along or with various lipid and/or sugar derivatives that may, or may not, have a disulfide bridged dimer, or represent a cyclic dimer.

Figure 8:
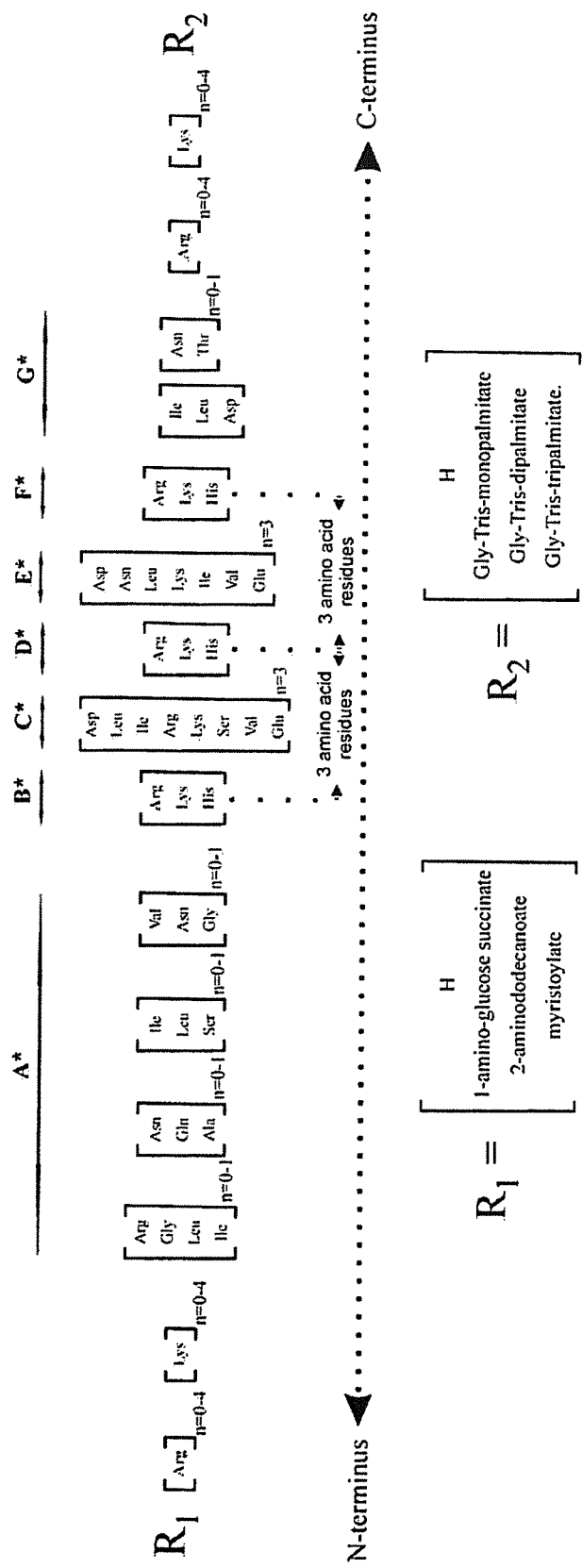
FIG. 8 presents various embodiments of the Class II of TCR peptide inhibitor sequences based upon a general formula, wherein in the general formula describes variants of the parent sequences of HTLV-1 $gp21^{313-353}$, HVA $Tio^{225-242}$, and HVS $Tip^{211-228}$.

In one embodiment, the present invention contemplates a Class II peptide derivative having the general formula $R_1$-A*-B*-C*-D*-E*-F*-G*-$R_2$ (See FIG. 8) (SEQ ID NO: 87), or a di-sulfide bridged, linear dimer thereof, or a cyclic dimer thereof, wherein;

A* is absent, or 1-4 D- or L-amino acids selected from the group including, but not limited to, Arg, Gly, Leu, Ile, Asn, Gln, Ala, Ser, and Val;

B* is a positively charged D- or L-amino acid;

C* is a peptide comprising 3 amino acids selected from the group including, but not limited to, Asp, Leu, Ile, Arg, Lys, Ser, Val, and Glu;

D* is a positively charged D- or L-amino acid;

E* is a peptide comprising 3 amino acids selected from the group including, but not limited to, Asp, Asn, Leu, Lys, Ile, Val, and Glu;

F* is a positively charged D- or L-amino acid;

G* is Ile, Leu or Asp, or a peptide comprising 2 amino acids selected from the group including, but not limited to, Ile, Leu, Asp, Asn, and Thr;

$R_1$ is absent (i.e., for example, —H) or 1-amino-glucose succinate, 2-aminododecanoate, or myristoylate; and $R_2$ is absent (i.e., for example, —H) or Gly-Tris-monopalmitate, -dipalmitate and -tripalmitate.

In some embodiments, peptide derivatives are created wherein (SEQ ID NO: 88);

A* is a peptide comprising 1-4 amino acids selected from the group comprising Arg, Gly, Leu, Ile, Asn, Gln, Ala, Ser, and Val;

B* is selected from Arg, His or Lys;

C* is a peptide comprising 3 amino acids selected from the up comprising Asp, Leu, Ile, Arg, Lys, Ser, Val, and Glu;

D* is selected from Arg, His or Lys;

E* is a peptide comprising 3 amino acids selected from the group comprising Asn, Asp, Leu, Lys, Ile, Val, and Glu;

F* is selected from Arg, His or Lys; and

G* is a peptide comprising 2 amino acids selected from the group comprising Ile, Leu, Asp, Asn, and Thr.

In one embodiment, the present invention contemplates a peptide derivative having the general formula $R_1$-[Arg and/or Lys]$_{n=0-4}$-A*-B*-C*-D*-E*-F*-G*-[Arg and/or Lys]$_{n=0-4}$-R$_2$ or a di-sulfide bridged, linear dimer thereof, or a cyclic dimer thereof, wherein (SEQ ID NO: 89);

A* may be i) absent; or ii) 1-4 D- or L-amino acids selected from the group including, but not limited to, Arg, Gly, Leu, Ile, Asn, Gln, Ala, Ser, and Val;

B* may be selected from the group including, but not limited to, Arg, Lys, or His;

C* is 3 amino acids selected from the group including, but not limited to, Asp, Leu, Ile, Arg, Lys, Ser, Val, and Glu;

D* may be selected from the group including, but not limited to, Arg. Lys, or His;

E* is 3 amino acids selected from the group including, but not limited to, Ala, Phe, or Gly;

F* may be selected from the group including, but not limited to, Arg, Lys, or His; and G* may be i) Ile, Leu, or Asp, or ii) 2 amino acids selected from the group including, but not limited to, Leu, Ile, Asn, and Thr;

R$_1$ and R$_2$ may be either i) absent; ii) a conjugated lipid selected from the group including, but not limited to, Gly-Tris-monopalmitate, -dipalmitate and -tripalmitate; or iii) a conjugated sugar selected from the group including, but not limited to, 1-amino-glucose succinate, 2-aminododecanoate, or myristoylate. See, FIG. 8.

The above general formula represents one embodiment of Class II of TCR peptide inhibitory sequences of viral origin (for example, HVS Tip$^{211-228}$; See FIG. 5) comprising at least one conserved domain that contains a highly homologous sequence between this sequence and the HTLV-1 gp21$^{313-353}$. In one embodiment, a HVS Tip$^{211-228}$-derived TCR inhibitory peptide comprises ANERNIVKDLKRLEN-KIN (SEQ ID NO: 7) along or with various lipid and/or sugar derivatives that may, or may not, have a disulfide bridged dimer, or represent a cyclic dimer.

In one embodiment, the present invention contemplates a Class III peptide derivative having the general formula R$_1$-A-B-C-D-E-F-R$_2$ (See FIG. 8), or a di-sulfide bridged, linear dimer thereof, or a cyclic dimer thereof, wherein (SEQ ID NO: 90);

A** is absent, or 1-8 D- or L-amino acids selected from the group including, but not limited to, Ala, Pro, Cys, Thr, Asn, Met, Glu, Ser, Gly, Tyr, Leu, Ile, and Gln;

B** is a positively charged D- or L-amino acid;

C** is a peptide comprising 8 amino acids selected from the group including, but not limited to, Ser, Trp, Arg, Lys, His, Pro, Met, Gly, Ala, Thr, Leu, Ile, Val, Asp, Asn, Thr, Glu, Phe, and Gln;

D** is a positively charged D- or L-amino acid;

E** is absent, or a peptide comprising 1-3 amino acids selected from the group including, but not limited to, Gln, Cys, Glu, Trp, Arg, Leu, Ile, Phe, Gly, and Lys;

F** is absent, or a peptide comprising 1-4 amino acids selected from the group including, but not limited to, Asn, Leu, Ile, Thr, Phe, and Val;

R$_1$ is absent (i.e., for example, —H) or 1-amino-glucose succinate, 2-aminododecanoate, or myristoylate; and R$_2$ is absent (i.e., for example, —H) or Gly-Tris-monopalmitate, -dipalmitate and -tripalmitate.

In some embodiments, peptide derivatives are created wherein (SEQ ID NO: 91);

A** is a peptide comprising 1-8 amino acids selected from the group comprising Ala, Pro, Cys, Thr, Asn, Met, Glu, Ser, Gly, Tyr, Leu, Ile, and Gln;

B** is selected from Arg, His or Lys;

C** is a peptide comprising 8 amino acids selected from the group comprising Ser, Trp, Arg, Lys, His, Pro, Met, Gly, Ala, Thr, Leu, Ile, Val, Asp, Asn, Thr, Glu, Phe, and Gln;

D** is selected from Arg, His or Lys;

E** is a peptide comprising 3 amino acids selected from the group comprising Gln, Cys, Glu, Trp, Arg, Leu, Ile, Phe, Gly, and Lys;

F** is a peptide comprising 4 amino acids selected from the group comprising Asn, Leu, Ile, Thr, Phe, and Val.

Figure 9:
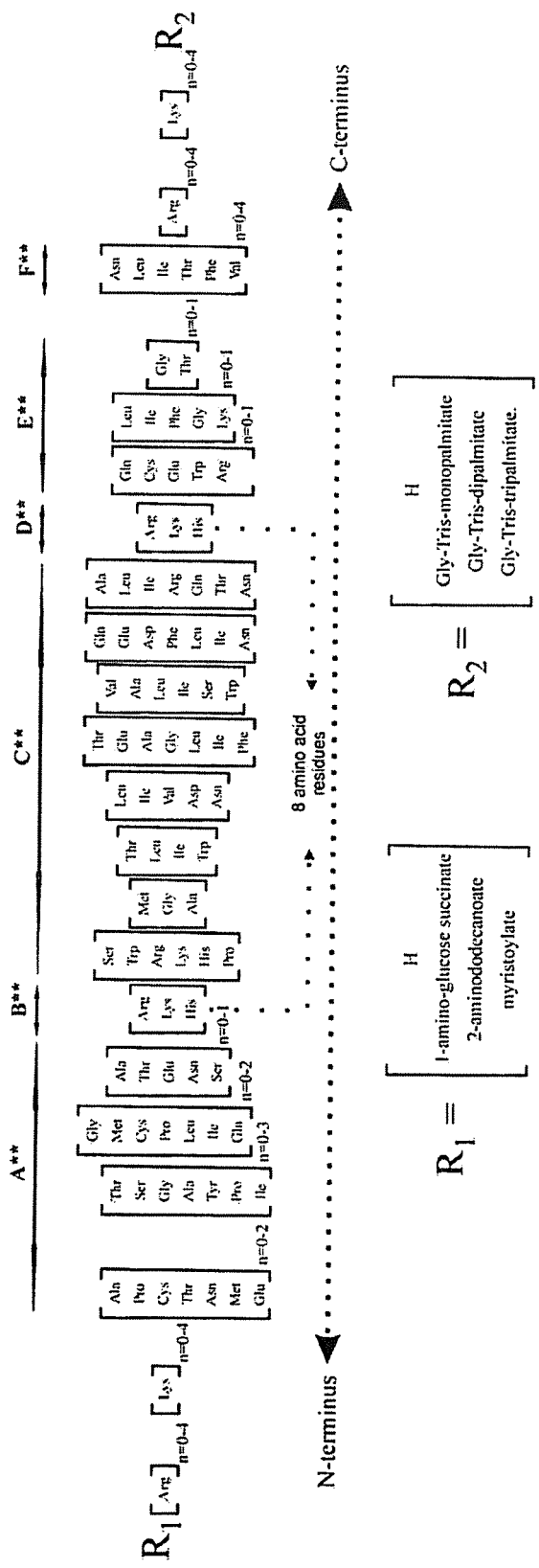
FIG. 9 presents various embodiments of the Class III of TCR peptide inhibitor sequences based upon a general formula, wherein in the general formula describes variants of the parent sequences of LASV FP ($gp2^{260-298}$), LCMV FP ($gp2^{266-304}$), MOPV FP ($gp2^{258-296}$), TACV FP ($gp2^{262-300}$), CKS-17, SEBOV $gp2^{584-600}$, ZEBOV $gp2^{584-600}$, MARV $gp2^{585-601}$, Fr-MLV Env $gp^{548-564}$ and HHV-6 $U24^{28-60}$.

In one embodiment, the present invention contemplates a peptide derivative having the general formula R$_1$-[Arg and/or Lys]$_{n=0-4}$-A-B-C-D-E-F-[Arg and/or Lys]$_{n=0-4}$-R$_2$ or a di-sulfide bridged, linear dimer thereof, or a cyclic dimer thereof, wherein (SEQ ID NO: 92);

A** may be i) absent; or ii) 1-8 D- or L-amino acids selected from the group including, but not limited to, Ala, Pro, Cys, Thr, Asn, Met, Glu, Ser, Gly, Tyr, Leu, Ile, and Gln;

B** may be selected from the group including, but not limited to, Arg, Lys, or His;

C** is 8 amino acids selected from the group including, but not limited to, Ser, Trp, Arg, Lys, His, Pro, Met, Gly, Ala, Thr, Leu, Ile, Val, Asp, Asn, Thr, Glu, Phe, and Gln;

D** may be selected from the group including, but not limited to, Arg, Lys, or His;

E** may be i) absent, or ii) 1-3 amino acids selected from the group including, but not limited to, Gln, Cys, Glu, Trp, Arg, Leu, Ile, Phe, Gly, and Lys;

F** may be i) absent, or ii) 1-4 amino acids selected from the group including, but not limited to, Asn, Leu, Ile, Thr, Phe, and Val;

R$_1$ and R$_2$ may be either i) absent; ii) a conjugated lipid selected from the group including, but not limited to, Gly-Tris-monopalmitate, -dipalmitate and -tripalmitate; or iii) a conjugated sugar selected from the group including, but not limited to, 1-amino-glucose succinate, 2-aminododecanoate, or myristoylate. See, FIG. 9.

The above general formula represents one embodiment of Class III of TCR peptide inhibitory sequences of viral origin (for example, LASV FP (gp2$^{260-298}$); See FIG. 5) comprising at least one conserved domain that contains a highly homologous sequence between this sequence and the HIV-1 gp41 FP. In one embodiment, a LASV FP (gp2$^{260-298}$)-derived TCR inhibitory peptide comprises GTFTWTLSD-SEGKDTPGGYCLTRWMLIEAELKCFGNTAV (SEQ ID NO: 8) along or with various lipid and/or sugar derivatives that may, or may not, have a disulfide bridged dimer, or represent a cyclic dimer.

In one embodiment, the present invention contemplates a method of rational designing of linear or cyclic peptides and lipid- and/or sugar-conjugated peptides consisting of L- or D-stereoisomeric amino acids in order to increase effectiveness of the peptides in inhibiting the function of the TCRαβ/CD3εδ/CD3εγ/ζζ receptor complex. This method is described in (US Pat. Appl. 20090075899) and incorporated herein by reference in their entirety. In one embodiment, the method comprises using rational combinations of the peptide blocks from different classes of TCR peptide inhibitor sequences of viral origin, namely A, A*, A**, B, B*, B**, C, C*, C**, D, D*, D**, E, E*, E**, F, F*, F**, and G*, as designated in FIGS. 7, 8, and 9, thereby optimizing and increasing binding to the transmembrane domains of CD3ε, δ and TCRζ chains. See, FIG. 10.

In one embodiment, the present invention contemplates a combinatorial TCR peptide inhibitor sequence derivative having the general formula R$_1$-A**-B*-C*-D*-C-D-E**-R$_2$ (See FIG. 10), or a di-sulfide bridged, linear dimer thereof, or a cyclic dimer thereof, wherein (SEQ ID NO: 93);

A** is absent, or 1-8 D- or L-amino acids selected from the group including, but not limited to, Ala, Pro, Cys, Thr, Asn, Met, Glu, Ser, Gly, Tyr, Leu, Ile, and Gln;

B* is a positively charged D- or L-amino acid;

C is a peptide comprising 4 hydrophobic D- or L-amino acids, or Thr and 3 hydrophobic D- or L-amino acids, including D- or L-cysteine or a D- or L-cysteine homologue;

C* is a peptide comprising 3 amino acids selected from the group comprising Asp, Leu, Ile, Arg, Lys, Ser, Val, and Glu;

D is a positively charged D- or L-amino acid;

D* is a positively charged D- or L-amino acid;

E** is absent, or a peptide comprising 1-3 amino acids selected from the group including, but not limited to, Gln, Cys, Glu, Trp, Arg, Leu, Ile, Phe, Gly, and Lys;

$R_1$ is absent (i.e., for example, —H) or 1-amino-glucose succinate, 2-aminododecanoate, or myristoylate; and $R_2$ is absent (i.e., for example, —H) or Gly-Tris-monopalmitate, -dipalmitate and -tripalmitate.

In some embodiments, peptide derivatives are created wherein (SEQ ID NO: 94);

A** is a peptide comprising 1-8 amino acids selected from the group comprising Ala, Pro, Cys, Thr, Asn, Met, Glu, Ser, Gly, Tyr, Leu, Ile, and Gln;

B* is selected from Arg, His or Lys;

C is a peptide comprising 4 amino acids selected from the group comprising Leu, Ile, Thr, and Pro;

C* is a peptide comprising 3 amino acids selected from the group comprising Asp, Leu, Ile, Arg, Lys, Ser, Val, and Glu;

D is selected from from Arg, His or Lys;

D* is selected from from Arg, His or Lys; and

E** is a peptide comprising 3 amino acids selected from the group comprising Gln, Cys, Glu, Trp, Arg, Leu, Ile, Phe, Gly, and Lys.

In one embodiment, the present invention contemplates a peptide derivative having the general formula $R_1$-[Arg and/or Lys]$_{n=0-4}$-A**-B*-C*-D*-C-D-E**-[Arg and/or Lys]$_{n=0-4}$-$R_2$ or a di-sulfide bridged, linear dimer thereof, or a cyclic dimer thereof, wherein (SEQ ID NO: 95);

A** may be i) absent; or ii) 1-8 D- or L-amino acids selected from the group including, but not limited to, Ala, Pro, Cys, Thr, Asn, Met, Glu, Ser, Gly, Tyr, Leu, Ile, and Gln;

B* may be selected from the group including, but not limited to, Arg, Lys, or His;

C is 4 amino acids selected from the group including, but not limited to, Leu, Ile, Thr, and Pro;

C* is 3 amino acids selected from the group including, but not limited to, Asp, Leu, Ile, Arg, Lys, Ser, Val, and Glu;

D may be selected from the group including, but not limited to, Arg, Lys, or His;

D* may be selected from the group including, but not limited to, Arg, Lys, or His;

E** may be i) absent, or ii) 1-3 amino acids selected from the group including, but not limited to, Gln, Cys, Glu, Trp, Arg, Leu, Ile, Phe, Gly, and Lys;

$R_1$ and $R_2$ may be either i) absent; ii) a conjugated lipid selected from the group including, but not limited to, Gly-Tris-monopalmitate, -dipalmitate and -tripalmitate; or iii) a conjugated sugar selected from the group including, but not limited to, 1-amino-glucose succinate, 2-aminododecanoate, or myristoylate. See, FIG. 10.

The above general formula represents one embodiment of combinatorial TCR peptide inhibitory sequences of viral origin (See FIG. 10) comprising at least one conserved domain that contains a highly homologous sequence between this sequence and the TCRα transmembrane domain, HVS Tip$^{211-228}$, HVA Tio$^{225-242}$, HTLV gp21$^{313-353}$, and/or HIV-1 gp41 FP. In one embodiment, a combinatorial TCR inhibitory peptide of viral origin comprises LQNRDLKRLLFLKRKT (SEQ ID NO: 9) along or with various lipid and/or sugar derivatives that may, or may not, have a disulfide bridged dimer, or represent a cyclic dimer.

In another embodiment, the method comprises conjugating at least one lipid and/or at least one sugar to the C- and/or N-termini of the peptide, thereby increasing binding to the transmembrane domains of CD3ε, δ and TCRζ chains and/or improving the penetration of the peptide variant into the T cell membrane. In one embodiment, the lipid- and or sugar-conjugated peptide variants comprise D-amino acids, thereby increasing resistance to protease degradation. In one embodiment, a protease resistant peptide variant is useful clinically for inhibiting T cell activation in T cell-mediated disorders.

In some embodiments, conjugated peptide variants are synthesized using the standard procedures (Amon et al. *BBA Mol Cell Res* 2006; 1763:879-88; Whittaker et al. *Pept Res* 1993; 6:125-8; *Chemistry of Peptide Synthesis*, N. Leo Benoiton (ed.), *CRC,* 2005; Gerber et al. *FASEB J* 2005; 19:1190-2; Kliger et at *J Biol Chem* 1997; 272:13496-505; Merrifield et at *Biochemistry* 1982; 21:5020-31).

In one embodiment, the rational design method comprises inserting at least one polyarginine and/or polylysine sequence into a TCR peptide inhibitor of the present invention, thereby increasing binding to the transmembrane domains of the CD3ε, δ and TCRζ chains and/or improving the penetration of the peptide variant into the platelet membrane. Other modifications of the peptides contemplated herein include, but are not limited to, modifications to side chains, incorporation of unnatural amino acids and/or their derivatives during peptide synthesis and the use of crosslinkers and other methods which impose conformational constraints on the peptides. It may also be possible to add various groups to the peptide of the present invention to confer advantages such as increased potency or extended half life in vivo without substantially decreasing the biological activity of the peptide. It is intended that such modifications to the peptide of the present invention which do not result in a decrease in biological activity are within the scope of the present invention.

Any combination of the above embodiments may be used together in order to increase effectiveness of the peptide variants to inhibit the function of the TCRαβ/CD3εδ/CD3εγ/ζζ receptor complex. The most effective inhibitory peptides and derivatives thereof may be identified by typical screening assay procedures for evaluation of inhibition of T cell activation (*Drug Discovery And Evaluation: Pharmacological Assays*, Hans G, Vogel (ed.) Springer Berlin Heidelberg, 2007).

V. Peptide-Based Inhibitors

Although it is not necessary to understand the mechanism of an invention, it is believed that inhibition of a T cell receptor (TCR) signaling can be achieved by binding of a peptide-based inhibitor of the present invention to the transmembrane (TM) domain of the CD3ε, δ and TCRζ chains, thus substituting the TCRα subunit and abolishing the interactions between the TM domains of the TCRα and the CD3ε, δ and TCRζ chains. One possible result is the inhibition of TCR-mediated transmembrane signaling because antigen binding to the extracellular domains of the disulfide-linked TCRαβ antigen recognition subunits does not lead to clustering (i.e., for example, oligomerization) of CD3ε, δ and TCRζ chains. It is further believed that this clustering induces the phosphorylation of tyrosine residues in the intracellular ITAM domains of these signaling subunits and initiates downstream signaling.

The TM domains of the TCRα, CD3ε, δ and TCRζ chains comprise hydrophobic sequences that may adopt a stable alpha-helical structure within a T cell membrane lipid bilayer. It is believed that electrostatic interactions between these TM domains maintain the integrity of the TCRαβ/CD3εδ/CD3εγ/ζζ receptor complex and are provided by the interactions between the positively charged amino acid residues in the TM regions of the TCRαβ chains and the negatively charged amino acid residues in the TM domains of ζζ homodimer, CD3εγ, and CD3εδ heterodimers.

As disclosed in (WO 96/22306; WO 97/47644; US Pat. Appl. 20050070478), the simplest and the most selective and effective peptide inhibitor would be a synthetic peptide corresponding to the TM domain of TCRα subunit. However, as disclosed in (US Pat. Appl. 20090075899) and incorporated herein by reference in its entirety, peptide inhibitor sequence, alone, is not the only relevant consideration. In one embodiment, a peptide inhibitor targeted to the transmembrane interactions should be optimized for cell membrane binding. In one embodiment, a peptide inhibitor should be optimized for membrane insertion, thereby attaining a close spatial proximity and/or proper orientation to an interacting partner (i.e., for example, the TM domains of the ζζ homodimer and CD3δε heterodimer). In one embodiment, a peptide inhibitor should be optimized for binding effectiveness to an interacting partner.

Although it is not necessary to understand the mechanism of an invention, it is believed that TCR peptide inhibitors disclosed in (WO 96/22306; WO 97/47644; US Pat. Appl. 20050070478; US Pat. Appl. 20070185025; WO 2006077601) comprising the wild type TM domain of TCRα, filoviral peptides or HIV gp41 fusion peptide (FP) are not optimized for each of the above three factors. Other embodiments, however, are contemplated by the present invention by using extracellularly administered synthetic peptides with primary amino acid sequences of viral origin of the present invention which are optimized for at least one of the above three considerations. Thus, the 30-40% inhibition of T cell activation observed for the TCR core peptide (CP), filoviral peptides and HIV gp41 FP (WO 96/22306; WO 97/47644; US Pat. Appl. 20050070478; US Pat. Appl. 20070185025; WO 2006077601), can be significantly improved in terms of efficiency by rational design of the peptide-based inhibitors of the present invention. For example, the inhibition activity the TCR CP has been reported to increase from 30 to 80% by lipidation of the relevant peptide inhibitors.

In summary, the present invention contemplates optimizing the effectiveness and selectivity of peptide inhibitors for TCR-mediated signaling, by adhering to at least one of these guidelines: 1) ability to effectively bind to the platelet plasma membrane and insert into the membrane (i.e., for example, increasing hydrophobicity); 2) ability to adopt helical conformation upon membrane binding and penetration (i.e., for example, increasing intrinsic helicity); 3) ability to selectively and effectively bind to the TM domain of the ζζ homodimer and CD3δε heterodimer, thus effectively competing with the TCRα subunit for the binding to these signaling subunit (i.e., for example, by increasing stable α-helixes). These guidelines are described in (US Pat. Appl. 20090075899) and incorporated herein by reference in its entirety.

These guidelines were used to develop a method of rational designing of the peptides of the present invention in order to increase effectiveness of the peptides in inhibition of function of the TCRαβ/CD3εδ/CD3εγ/ζζ receptor complex.

1. Hydrophobicity

The hydrophobicity (or lipophilicity) of peptides and peptide analogues may be increased by i) inserting hydrophobic regions; ii) improving the ability of a peptide-based inhibitors to bind the membrane; and/or iii) improving the ability of a peptide-based inhibitor to insert into a membrane. In one embodiment, hydrophobic regions may be inserted into a peptide inhibitor sequence by using lipophilic groups including, but not limited to, myristoylate-, 1-aminoglucose succinate, 2-aminododecanoate, or Gly-Tris-palmitate, -dipalmitate or -tripalmitate, coupled to the N- and/or C-termini of a peptide. In one embodiment, the membrane binding/insertion ability of a peptide inhibitor may be improved by using highly positively charged poly-Lys or poly-Arg sequences coupled to an N- and/or C-terminus. A general formula summarizing many suggested inhibitory peptides and/or compositions is presented that incorporates both approaches that are expected to increase the effectiveness of the peptides to inhibit the function of TCR. See, FIGS. 7, 8, 9 and 10.

Lipid-binding activity of the test peptide-based inhibitors can be predicted using ProtParam™ software (us.expasy.org/tools/protparam.html) and experimentally evaluated by different techniques such as, for example, surface plasmon resonance (SPR) or sucrose-loaded vesicle binding assay. Based on the obtained results, a peptide-based inhibitor with optimal membrane-binding activity can be chosen. For example, "Grand Average Of Hydropathy" (GRAVY) scores for peptides can be obtained using ProtParam™, in which a score >−0.4 (=mean score for cytosolic proteins) indicates the probability for membrane association (i.e., for example, the higher the score, the greater the probability for membrane association).

2. Helicity

As discussed above, the primary sequence of the parent inhibitory peptides of the present invention (See FIG. 5 and TABLE 2), can be modified to improve the ability of various peptide-based inhibitors contemplated herein to adopt helical conformation upon membrane binding and penetration. Overall protein folding may be specified by hydrophobic-polar residue patterning, whereas the bundle oligomerization state, detailed main-chain conformation, and interior side-chain rotamers may be engineered by computational enumerations of packing in alternate backbone structures. Main-chain flexibility is incorporated through an algebraic parameterization of the backbone (Harbury et al. *Science* 1998; 282:1462-7).

Peptide helicity of the designed primary sequences of various peptide-based inhibitors of the invention contemplated herein can be first evaluated computationally using secondary structure prediction programs. (i.e., for example, Expasy Proteomics Tools; expasy.org/tools). The most promising inhibitors can be measured experimentally for intrinsic and/or induced helicity using circular dichroism (CD) spectroscopy. Circular dicroism spectroscopy is used to analyze the secondary structure of a protein and/or peptide. Specifically, CD spectroscopy measures differences in the absorption of left-handed polarized light versus right-handed polarized light which arise due to structural asymmetry. The absence of regular structure results in zero CD intensity, while an ordered structure results in a spectrum which can contain both positive and negative signals. α-helix, β-sheet, and random coil structures each give rise to a characteristic shape and magnitude of CD spectrum. The approximate fraction of each secondary structure type that is present in any peptide or protein can thus be determined by analyzing its far-UV CD spectrum as a sum of fractional multiples of such reference spectra for each structural type. Like all spectroscopic techniques, the CD signal reflects an average of the entire molecular population. Thus, while CD can determine that a peptide or protein contains about 50% α-helix, it cannot determine which specific residues are involved in the α-helical portion. Based on the obtained results, a peptide-based inhibitor optimized with the predicted and/or observed, intrinsic and/or induced optimal helicity can be chosen.

Alternatively, secondary structure prediction programs (for example, expasy.org/tools/) may be used to accurately predict the peptide helicity based on primary sequence of the computationally designed peptide-based inhibitors. A few of the available programs include, but are not limited to: a) AGADIR—An algorithm to predict the helical content of peptides; b) APSSP—Advanced Protein Secondary Structure Prediction Server; c) GOR (Garnier et al. *Methods Enzymol* 1996; 266:540-53); d) HNN—Hierarchical Neural Network method (Guermeur et al. *Bioinformatics* 1999; 15:413-21); e) Jpred—A consensus method for protein secondary structure prediction at University of Dundee; f) JUFO—Protein secondary structure prediction from sequence (neural network); g) nnPredict—University of California at San Francisco (UCSF); h) Porter—University College Dublin; i) PredictProtein—PHDsec, PHDacc, PHDhtm, PHDtopology, PHDthreader, MaxHorn, EvalSec from Columbia University; j) Prof—Cascaded Multiple Classifiers for Secondary Structure Prediction; k) PSA—BioMolecular Engineering Research Center (BMERC)/Boston; l) PSIpred—Various protein structure prediction methods at Brunel University; m) SOPMA—Geourjon and Deleage, 1995; n) Sspro—Secondary structure prediction using bidirectional recurrent neural networks at University of California; and o) DLP—Domain linker prediction at RIKEN.

3. α-Helix Stability

Although it is not necessary to understand the mechanism of an invention, it is believed that the TM domains of the TCRα, CD3δ, CD3ε and ζ chains represent stable α-helixes and, thus, the interactions can be presented using helix-wheel diagrams. See, FIGS. 2, 3, 5, 6A, 6B, and 6C. As described in (US Pat. Appl. 20090075899) and incorporated herein by reference in its entirety, these diagrams are based on the primary peptide/protein sequence and can be created using commercially and publicly available programs (i.e., including, but not limited to, Antheprot v.6.0; antheprotp-bil.ibcp.fr; or Helical Wheel Custom Images and Interactive Java Applets; cti.itc.virginia.edu/.about.cmg/Demo/wheel/wheelApp.html and (net/helical.htm). These diagrams can be used for evaluation of close proximity and/or proper orientation of positively charged amino acid residue(s) of the peptide or peptide analogue of the present invention towards an interacting partner (i.e., for example, negatively charged TM residues of the ζζ homodimer and CD3δε heterodimer).

The electrostatic interactions between the positively charged amino acid residues in the TM regions of the TCRα chain and the negatively charged amino acid residues in the TM domains of ζζ homodimer and CD3δε heterodimer stabilize the association of these respective subunits, thereby playing a role in antigen-induced TCR-mediated T cell activation. Some embodiments of peptide-based inhibitors contemplated by the present invention aim to interrupt these interactions and replace the TCRα subunit (See FIGS. 3, 6A, 6B, and 6C). In one embodiment, peptide-based inhibitors can be computationally designed to increase their competitiveness with the TCRα subunit. In one embodiment, competitiveness may be increased by using a conservative amino acid substitution of arginine for lysine. In another embodiment, competitiveness may be increased by inserting a positively charged amino acid residue (i.e., for example, arginine and/or lysine). In one embodiment, the insertion and/or substitution is located within an α-helix of the peptide-based inhibitors of the invention, thereby increasing the binding activity to the TM domains of ζζ homodimer and CD3δε heterodimer and enhancing the effectiveness of the peptides to inhibit the function of TCR.

4. Peptide-based Inhibitor Sequence Listing

A list of the sequences of the peptides and peptide analogues shown below includes, but is not limited to, the peptide-based inhibitors predicted to be effective in inhibiting the TCR signaling mechanism. See, Table 2.

Accordingly, it is intended that the present invention includes within its scope peptides which include additional amino acids to the "core" sequence of the peptide of the present invention and which affect the transmembrane interactions between the TCR α subunit and CD3ε, δ and ζ subunits.

TABLE 2

Exemplary Peptide-Based TCRαβ/CD3δε/CD3γε/ζζ Complex Sequences

| ## | $R_1{}^a$ | Sequence (the "core" sequence of the peptide of the present invention is underlined) | $R_2{}^b$ | SEQ ID NO |
|---|---|---|---|---|
| | | Class I | | |
| 1 | — | MYKTPTLKYFGGFNFSQIL (parent) (SARS-CoV FP) | — | 6 |
| 2 | — | MYKTPTLKYFG (SARS-CoV FP core peptide) | — | 10 |
| 3 | — | MYKIPTLKYFG | — | 11 |
| 4 | — | MYKILTLKYFG | — | 12 |
| 5 | — | GYKILTLKYFG | — | 13 |
| 6 | — | GYRTPTLKVFG | — | 14 |

| | | | | |
|---|---|---|---|---|
| 7 | – | GFRIPLLKYFG | - | 15 |
| 8 | – | (GFRIPLLKYFG)₂ᶜ | - | 16 |
| 9 | LA | GYRTPTLKVFG | - | 14 |
| 10 | Myr | GYRTPTLKVFG | - | 14 |
| 11 | – | GYRTPTLKVFG | + | 14 |
| 12 | Myr | GYRTPTLKVFG | + | 14 |
| 13 | – | GYRTPTLKVFGGFNFSQIL | - | 17 |
| 14 | – | (GYRTPTLKVFGGFNFSQIL)₂ | - | 18 |
| 15 | – | (C*GYRTPTLKVFGGFNFSQIL-)₂ᵈ | - | 19 |
| 16 | – | (C*GYRTPTLKVFGGFNFSQILC*)₂ | - | 20 |
| 17 | – | GYRTPTLKVFGGFNFSQIL | - | 17 |
| 18 | – | GYKTPTLKYFGGFNFSQIL | - | 21 |
| 19 | LA | GYKTPTLKYFGGFNFSQIL | - | 21 |
| 20 | – | GYKTPTLKYFGGFNFSQIL | + | 21 |
| 21 | Myr | GYKTPTLKYFGGFNFSQIL | - | 21 |
| 22 | Myr | GYKTPTLKYFGGFNFSQIL | + | 21 |
| 23 | – | KKKRGYKTPTLKYFGGFNFSQILKR | - | 22 |
| 24 | – | (KKKRGYKTPTLKYFGGFNFSQILKR)₂ | - | 23 |
| 25 | – | KKRGYKTPTLKVFGKR | - | 24 |
| 26 | – | (KKRGYKTPTLKVFGKR)₂ | - | 25 |
| Class 2 | | | | |
| 27 | – | AVPVAVWLVSALAMGAGVAGGITGSMSLASGKSLLHEVDKD (parent) (HTLV-1 gp21³¹³⁻³⁵³) | - | 26 |
| 28 | – | LASGKSLLHEVDKD (HTLV-1 gp21³¹³⁻³⁵³ core peptide) | - | 27 |
| 29 | – | ATDGQLNHRVEKVEKKLT (parent) (HVA Tio²²⁵⁻²⁴²) | - | 28 |
| 30 | – | LNHRVEKVEKKLT (HVA Tio²²⁵⁻²⁴² core peptide) | - | 29 |
| 31 | – | ANERNIVKDLKRLENKIN (parent) (HVS Tip²¹¹⁻²²⁸) | - | 7 |
| 32 | – | IVKDLKRLENKIN (HVS Tip²¹¹⁻²²⁸ core peptide) | - | 30 |
| 33 | – | LASGKSLLHVEKKD | - | 31 |
| 34 | – | LASGKRVEHEVDKD | - | 32 |
| 35 | – | LASGKDLKHVEKKD | - | 33 |
| 36 | – | LASGKSLLHLENKD | - | 34 |
| 37 | – | ATDGQLNHRVEKLENKLT | - | 35 |
| 38 | – | ANERNIVKRVERLENKIN | - | 36 |
| 39 | Myr | LASGKDLKHVEKKD | - | 33 |
| 40 | - | LASGKDLKHVEKKD | + | 33 |
| 41 | Myr | LASGKDLKHVEKKD | + | 33 |
| 42 | – | (LASGKDLKHVEKKD)₂ | - | 79 |
| 43 | – | (C*LASGKDLKHVEKKD)₂ | - | 80 |

| | | | | |
|---|---|---|---|---|
| 44 | – | LNHRVEKLENKLT | – | 81 |
| 45 | – | KKRLNHRVEKLENKLTKR | – | 37 |
| 46 | – | KKRLNHRVEKLENKLTKR | + | 37 |
| 47 | LA | KKRLNHRVEKLENKLTKR | – | 37 |
| 48 | Myr | KKRLNHRVEKLENKLTKR | – | 37 |
| 49 | – | RNIVKRVEKVEKKLT | – | 38 |
| 50 | – | (RNIVKRVEKVEKKLT)$_2$ | – | 39 |
| | | Class III | | |
| 51 | – | GTFTWTLSDSEGKDTPGGYC<u>LTRWMLIEAELKCFG</u>NTAV (parent) (LASV FP gp2$^{260-298}$) | – | 8 |
| 52 | – | <u>LTRWMLIEAELKCFG</u> (LASV FP core peptide) | – | 40 |
| 53 | – | GTFTWTLSDSSGVENPGGYC<u>LTKWMILAAELKCFG</u>NTAV (parent) (LCMV FP gp2$^{266-304}$) | – | 41 |
| 54 | – | <u>LTKWMILAAELKCFG</u> (LCMV FP core peptide) | – | 42 |
| 55 | – | GLFTWTLSDSEGNDMPGGYC<u>LTRSMLIGLDLKCFG</u>NTAI (parent) (MOPV FP gp2$^{258-296}$) | – | 43 |
| 56 | – | <u>LTRSMLIGLDLKCFG</u> (MOPV FP core peptide) | – | 44 |
| 57 | – | AFFSWSLTDPLGNEAPGGYC<u>LEKWMLVASELKCFG</u>NTAI (parent) (TACV FP gp2$^{262-300}$) | – | 45 |
| 58 | – | <u>LEKWMLVASELKCFG</u> (TACV FP core peptide) | – | 46 |
| 59 | – | LQNRRGLDLLFLKEGGL (parent) (CKS-17) | – | 47 |
| 60 | – | ILNRKAIDFLLRRWGGT (parent) (SEBOV gp2$^{584-600}$) | – | 48 |
| 61 | – | ILNRKAIDFLLQRWGGT (parent) (ZEBOV gp2$^{584-600}$) | – | 49 |
| 62 | – | LINRHAIDFLLTRWGGT (parent) (MARV gp2$^{585-601}$) | – | 50 |
| 63 | – | LQNRRGLDLLFLKEGGL (parent) (Fr-MLV Env gp$^{548-564}$) | – | 47 |

| # | Mod | Sequence | +/- | SEQ ID |
|---|---|---|---|---|
| 64 | — | VINDTSFVECIPPPQSRPAWNLWNNRRKTFSFL (parent) (HHV-6 U24$^{28-60}$) | — | 51 |
| 65 | — | QSRPAWNLWNNRRKT (HHV-6 U24$^{28-60}$ core peptide) | — | 52 |
| 66 | — | GYCLTRWMLIEAELKCFGNTAV | — | 53 |
| 67 | — | (GYC*LTRWMLIEAELKCFGNTAV)$_2$ | — | 54 |
| 68 | — | (GYGLTRWMLIEAELKCFGNTAV)$_2$ | — | 55 |
| 69 | LA | GYCLTRWMLIEAELKCFGNTAV | — | 56 |
| 70 | — | GYCLTRWMLIEAELKCFGNTAV | — | 56 |
| 71 | Myr | GYCLTRWMLIEAELKCFGNTAV | — | 56 |
| 72 | — | KKRGYCLTRWMLIEAELKCFGNTAVKR | — | 57 |
| 73 | — | LQNRKAIDLWNNKEGG | + | 58 |
| 74 | — | (LQNRKAIDLWNNKEGG)$_2$ | — | 59 |
| 75 | — | LQNRKAIDLWNNKEGG | — | 58 |
| 76 | Myr | LQNRKAIDLWNNKEGG | — | 58 |
| 77 | — | ILNRRGLDGLDLKEGG | — | 60 |
| 78 | — | (ILNRRGLDGLDLKEGG)$_2$ | — | 61 |
| 79 | — | KKRILNRRGLDGLDLKEGGKR | — | 62 |
| 80 | — | CLTKPAWNLLFLKRKTF | — | 63 |
| Combinatorial sequences | | | | |
| 81 | — | LQNRDLKRLLFLKRKT | — | 9 |
| 82 | — | (LQNRDLKRLLFLKRKT)$_2$ | — | 64 |
| 83 | LA | LQNRDLKRLLFLKRKT | — | 9 |
| 84 | — | LQNRDLKRLLFLKRKT | + | 9 |
| 85 | Myr | LQNRDLKRLLFLKRKT | — | 9 |
| 86 | — | KKLQNRDLKALLFLKRKTKR | — | 65 |
| 87 | — | KKLQNRDLICRLLFLKRKTKR | + | 65 |
| 88 | — | GQLNKTPTLKEGGL | — | 66 |
| 89 | — | GYCLTRRGLKEVDKEGG | — | 67 |
| 90 | — | (GYCLTRRGLKEVDKEGG)$_2$ | — | 68 |
| 91 | — | (GYC*LTRRGLKEVDKEGG)$_2$ | — | 69 |
| 92 | Myr | GYCLTRRGLKEVDKEGG | — | 70 |
| 93 | — | GYCLTRRGLKEVDKEGG | + | 70 |
| 94 | — | KKGYCLTRRGLKEVDKEGGKR | — | 71 |
| 95 | LA | KKGYCLTRRGLKEVDKEGGKR | — | 71 |
| 96 | — | KKGYCLTRRGLKEVDKEGGKR | + | 71 |
| 97 | LA | KKGYCLTRRGLKEVDKEGGKR | + | 71 |
| 98 | — | IPPPQSRTPTLKVFGG | — | 72 |

| 99 | — | (IPPPQSRTPTLKVFGG)2 | — | 73 |
| 100 | — | KKRIPPPQSRTPTLKVFGGKR | — | 74 |

[a]N-terminal group: LA, lipoamino acid, 2-aminododecanoate; Myr, myristoylate.
[b]C-terminal group: Gly-Tris-tripalmitate.
[c]Cyclic peptide.
[d]Disulfide-linked dimer (or disulfide-linked cyclic dimer).
*Cys involved in disulfide bond formation.
Abbreviations: TCR, T cell receptor; CP, core peptide, HIV, human immunodeficiency virus; FP, fusion peptide/protein; gp, glycoprotein; TMD, transmembrane domain; CKS-17, a synthetic retroviral envelope heptadecapeptide; Fr-MLV, Friend murine leukemia virus; gp, glycoprotein; HHV-6 U24, human herpesvirus 6 U24 protein; HTLV-1, human T lymphotropic virus type 1 HVA, herpesvirus ateles; HVS, herpesvirus saimiri; ITAM, immunoreceptor tyrosine-based activation motif; LASV, Lassa virus; LCMV, lymphocytic choriomeningitis virus; MARV, Marburg virus; MOPV, Mopeia virus; SARS-CoV, severe acute respiratory syndrome coronavirus; SEBOV, Sudan Ebola virus; TACV, Tacaribe virus; Tip, tyrosine kinase interacting protein; Tio, two-in-one protein; TMD, transmembrane domain; ZEBOV, Zaire Ebola virus.

5. Peptide Variant Consensus Sequences

Based upon the specific sequences contemplated in Table 2, the following consensus sequences may be constructed:

SEQ ID NO: 1: G-Y-$X_1$-$X_2$-$X_3$-$X_4$-$X_5$-$X_6$-$X_7$-$X_8$-$X_9$, wherein $X_1$ and $X_6$ are selected from the group consisting of R, K or H; $X_2$, $X_3$, $X_4$ and $X_5$ are selected from the group consisting of L, I, T or P; $X_7$ is selected from the group consisting of V or Y; $X_8$ consists of A or F or nothing; and $X_9$ consists of G or nothing.

SEQ ID NO: 2: $X_1$-$X_2$-$X_3$-$X_4$-$X_5$-$X_6$-L-$X_7$-$X_8$-$X_9$-E-$X_{10}$-$X_{11}$-$X_{12}$-$X_{13}$ wherein $X_1$ consists of R, G, I, L or nothing; $X_2$ consists of N, Q, A or nothing; $X_3$ consists of L, I, S or nothing; $X_4$ consists of V, N, G or nothing; $X_5$, $X_8$, and $X_{11}$ are selected from the group consisting of R, K or H; $X_6$ consists of D, R, S or nothing, $X_7$ consists of K, E, L or nothing, $X_9$ consists of L, V, E or nothing; $X_{10}$ consists of N, K, D or nothing; $X_{12}$ consists of I, L, D or nothing; and $X_{13}$ consists of N, T or nothing.

SEQ ID NO: 3: L-N-$X_1$-$X_2$-$X_3$-L-$X_4$-$X_5$-L-$X_6$-L-$X_7$-$X_8$-G-G-$X_9$ wherein $X_1$ and $X_7$ are selected from the group consisting of R, K or H; $X_2$ consists of S, R, K, H, P or W; $X_3$ consists of M, G or A; $X_4$ consists of L, I, V, N or D; $X_5$ consists of L, I, F, T, E, A or G; $X_6$ consists of E, Q, D, L, F, N or I, $X_8$ consists of Q, C, E, W or R, and $X_9$ consists of L, I, F, T, N or nothing.

SEQ ID NO: 4: L-Q-N-$X_1$-$X_2$-L-$X_3$-$X_4$-$X_5$-$X_6$-$X_7$-L-$X_8$-$X_9$-$X_{10}$-$X_{11}$-$X_{12}$ wherein $X_1$, $X_4$ and $X_8$ are selected from the group consisting of R, K or H; $X_2$ consists of D, R or S; $X_3$ consists of E, K or L; $X_5$ and $X_7$ consist of L, I, or T; $X_6$ consists of L, I, or P; $X_9$ consists of Q, C, E, W or R, $X_{10}$ consists of K, G, F, L, I or nothing; $X_{11}$ consists of T, G or nothing; and $X_{12}$ consists of F, L, I, T, N or nothing.

SEQ ID NO: 5: L-Q-N-$X_1$-$X_2$-$X_3$-$X_4$-L-$X_5$-$X_6$-L-$X_7$-$X_8$-$X_9$-$X_{10}$-$X_{11}$-$X_{12}$ wherein $X_1$, $X_5$ and $X_8$ are selected from the group consisting of R, K or H; $X_2$ and $X_4$ consist of L, I, or T; $X_3$ consists of L, I, or P; $X_6$ consists of D, R or S; $X_7$ consists of E, K or L; $X_9$ consists of Q, C, E, W or R, $X_{10}$ consists of K, G, F, L, I or nothing; $X_{11}$ consists of T, G or nothing; and $X_{12}$ consists of F, L, I, T, N or nothing.

VI. Therapeutic Applications of TCR Peptide Variant Inhibitors of Viral Origin

The invention further provides clinically therapeutic methods of intervening and modulating TCR function comprising using an agent selected from the group of agents or compositions of the present invention that block/inhibit/prevent/disrupt interactions between the TCRα chain and the homodimeric ζζ and heterodimeric CD3δε subunits of TCR.

Targeting MIRRs including TCR; HIV therapy, and high-throughput screening methods for screening and optimizing the effective peptide variant TCR inhibitors of the present invention that block/inhibit/prevent/disrupt interactions between the TCRα chain and the homodimeric ζζ and heterodimeric CD3δε subunits of TCR are described in (US Pat. Appl. 20090075899) and incorporated herein by reference in its entirety. See also FIGS. 1A, 1B, 1C, 1D, 2, and 3.

Various therapeutic applications of TCR inhibitors are described in (U.S. Pat. No. 6,057,294; US Pat. Appl. 20050070478; WO 96/22306; WO 97/47644; US Pat. Appl. 20070185025; WO 2006077601) and incorporated herein by reference in their entirety.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

EXAMPLES

The invention now being generally described, it will be more readily understood by reference to the following examples, which are included merely for purposes of illustration of certain aspects and embodiments of the present invention, and are not intended to limit the invention.

The following non-limiting Examples are put forth so as to provide those of ordinary skill in the art with illustrative embodiments as to how the compounds, compositions, articles, devices, and/or methods claimed herein are made and evaluated. The Examples are intended to be purely exemplary of the invention and are not intended to limit the scope of what the inventor regard as his invention. Efforts have been made to ensure accuracy with respect to numbers (e.g., amounts, temperature, etc.) but some errors and deviations should be accounted for. Unless indicated otherwise, parts are parts by weight, temperature is in ° C., or is at ambient temperature, and pressure is at or near atmospheric.

Example 1: Synthesis of Peptides

This example demonstrates one embodiment of a synthesized SARS-CoV fusion protein-related peptide.

The first step is to synthesize the short hydrophobic peptide corresponding to the SARS-CoV fusion peptide sequence. Although it is not necessary to understand the mechanism of an invention, it is believed that this peptide affects T cell receptor assembly and may interact with the ζζ homodimer and CD3δε heterodimer in a competitive fashion.

The synthesis of peptides may involve the use of protecting groups. Peptides can be synthesized by linking an amino group to a carboxyl group that has been activated by reaction with a coupling agent, such as dicyclohexylcarbodiimide (DCC). The attack of a free amino group on the activated carboxyl leads to the formation of a peptide bond and the release of dicyclohexylurea. It can be necessary to protect potentially reactive groups other than the amino and carboxyl groups intended to react. For example, the α-amino group of the component containing the activated carboxyl group can be blocked with a tertbutyloxycarbonyl group. This protecting group can be subsequently removed by exposing the peptide to dilute acid, which leaves peptide bonds intact.

In one embodiment, the amino acid sequence of a competitive peptide comprises $NH_2$-Met-Tyr-Lys-Thr-Pro-Thr-Leu-Lys-Tyr-Phe-Gly-Gly-Phe-Asn-Phe-Ser-Gln-Ile-Leu-OH (i.e., MYKTPTLKYFGGFNFSQIL (SEQ ID NO: 6)), hereafter referred to as "SARS CoV FP". In another embodiment, the amino acid sequence of a competitive peptide comprises $NH_2$-Met-Tyr-Ala-Thr-Pro-Thr-Leu-Ala-Tyr-Phe-Gly-Gly-Phe-Asn-Phe-Ser-Gln-Ile-Leu-OH (i.e., MYATPTLAYFGGFNFSQIL) (SEQ ID NO: 75)) wherein, $Lys_3$ and $Lys_8$ of SARS CoV FP substituted with $Ala_3$ and $Ala_8$, hereafter referred to as "SARS CoV FP-AA".

Although it is not necessary to understand the mechanism of an invention, it is believed that the positively charged $Lys_3$ and $Lys_8$ in SARS CoV FP form a salt bridge to an aspartic acid residues in the transmembrane (TM) domains of the of the ζζ homodimer and CD3δε heterodimer (A. B. Sigalov. *PLoS Pathog* 2009; 5:e1000404) (See also 5 and 6A). Thus, SARS CoV FP-AA may be considered a "control peptide" because of the $Ala_3$ and $Ala_8$ substitutions.

Unprotected peptides can be purchased from specialized companies (i.e., Sigma-Genosys, Woodlands, Tex., USA) with greater than 95% purity as assessed by HPLC. Peptide molecular mass can be checked by matrix-assisted laser desorption ionization mass spectrometry.

Example 2: Solubility

This example demonstrates that the hydrophobic properties of SARS CoV FP peptides and other peptides and compositions of the present invention may be overcome without risking cell toxicity.

The SARS CoV FP and SARS CoV FP-AA peptides can be noted to be hydrophobic and insoluble in aqueous solutions. A variety of solvents and carriers can be tested to improve their solubility. Solvents and/or carriers that improve solubility of CP and CP-A include, but not limited to, ethanol, dimethylsulphoxide (DMSO), dimethyl formamide (DMF), and trifluoracetic acid (TFA). When using DMSO as a solvent, the final concentration used in the platelet function experiments can range from 0.063%-0.250%. DMSO concentrations greater than 1% is believed to be toxic to cells. Stock solutions of SARS CoV FP and SARS CoV FP-AA can be prepared in DMSO and used at a 1:2000, 1:1000, or 1:400 dilution.

Example 3: Effect of T Cell Receptor Inhibitory Peptides of Viral Origin on Antigen-Stimulated Proliferation on Rat Primed Lymph Node Cells (PLNC) and T Cell Lines A. Cells The following cell lines can be used as described in (US Pat. Appl. 20050070478) and incorporated herein by reference: 2B4.11, a murine T cell hybridoma that expresses a complete antigen receptor on the cell surface and produces IL-2 following antigen recognition (cytochrome-c); an interleukin-2 (IL-2) dependent T cell line (CTLL) for conventional biological IL-2 assays; and the B-cell hybridoma cell line LK 35.2 (LK, I-$E^k$ bearing) which acts as the antigen presenting cell. The hybridomas is grown in T cell medium (RPMI-1640 media containing 10% fetal calf serum (FCS), gentamycin (80 µg/ml), glutamine (2 mM) and mercaptoethanol (0.002%)). The African green monkey kidney fibroblast cell line (COS) is grown in Dulbecco's modified Eagle's medium (DMEM) supplemented with 10% FCS.

B. Antigen Presentation Assay (Samelson et al. *J Immunol* 1987; 139:2708-14; US Pat. Appl. 20050070478)

The mouse T cell 2B4.11 hybridoma ($2 \times 10^4$) is cultured in microtitre wells with LK35.2 antigen presenting B cells ($2 \times 10^4$) and 50 µM pigeon cytochrome-c. After 16 hr 50 microlitres of assay supernatant is removed and assayed for the presence of IL-2. Serial twofold dilutions of the supernatant in media are cultured with the IL-2 dependent T cell line CTLL. After 16 hr the CTLL cells are pulsed with $^3$H-thymidine for 4 hr and IL-2 measurements (IU/ml) determined. This assay can be performed demonstrating that the "TCR inhibitor" is effective in inhibiting TCR-mediated cell activation.

C. Primed Lymph Node Cells (PLNC)

Male Wistar rats are injected intradermally at the base of the tail with 1 mg of heat-killed *Mycobacterium tuberculosis* (MTB) are suspended in 0.2 ml of squalane. When acute arthritis is well developed, after 10 to 16 days, rats are killed and the swollen popliteal lymph nodes are removed and a single cell suspension is made by pressing the tissue through a fine sieve under aseptic conditions. Cells are washed in complete medium, resuspended and counted. Approximately $3.5 \times 10^8$ viable cells can be obtained from two rats. The medium is RPMI 1640 supplemented with 25 mM Hepes, penicillin (100 µg/ml), streptomycin (80 µg/ml), $2.5 \times 10^{-5}$ M 2-mercaptoethanol and 2% pooled normal rat serum. The cells are pipetted into the wells of flat-bottom, 96 well microtitre plates at $2 \times 10^5$/well and a suspension of MTB is added to a final concentration of 100 µg/ml. "TCR inhibitors" or "control" peptides of the invention are delivered to the wells in 20 µl volume giving final concentrations of 1-100 µg/ml peptides (or 1-100 µM) and 0.01% acetic acid (or 0.1% dimetthylsulfoxide, DMSO), and a total of 200 µl per well. The plates are incubated at 37° C. in a humidified incubator at 5% $CO_2$ for 3 days and then are pulsed with 1 µCi per well of $^3$H-thymidine in 25 ml of medium. After a further overnight incubation, the cultures are harvested using an automated cell harvester, and counted in a β-scintillation spectrometer.

D. T Cell Lines (Sedgwick et al. *J Immunol Methods* 1989; 121:185-96; US Pat. Appl. 20050070478)

PLNCs from MTB-immunised rats are cultured in $75^2$ culture flasks at $5 \times 10^6$ per ml in a total of 50 ml containing 100 µg/ml MTB. After three days the cells are spun down and resuspended in 2 ml medium in a 15 ml centrifuge tube and are underlayered with 3 ml of Ficoll diatrizoate (9.9% Ficoll 400; 9.6% sodium diatrizoate), and centrifuged at 800 g for 20 minutes. The T cell blasts are recovered from the interface, washed twice and resuspended at $2 \times 10^5$ per ml in medium supplemented with 10% FCS and 15% con A-stimulated spleen cell supernatant, as a source of IL-2. After four days culture in the rest phase, $2 \times 10^5$ T cells per ml are restimulated with antigen and $10^7$ syngeneic rat thymocytes per ml to act as antigen presenting cells. The latter are inactivated by incubation with 25 μg/ml mitomycin C for 20 minutes at 37° C. and carefully washed three times. Cultures are in 75 cm² flasks containing 50 ml and the antigen, MTB, is added at 100 μg/ml. Flasks are stood up vertically and cultured for 3 days. Again T cell blasts are recovered by separation on Ficoll/diatrizoate, and the cycle is repeated. After 2-4 cycles, the cells are set in 96-well plates at $10^4$ T cells/well and $10^6$ mitomycin-C-inactivated thymocytes, in 200 ml medium containing 100 μg/ml MTB and 2% rat serum. To test the peptides and composition of the invention for the ability to inhibit antigen-stimulated T lymphocyte proliferation, additions of 200 μl are made to the wells containing "TCR inhibitors" or "control" peptides of the invention in 0.1% acetic acid or 0.1% DMSO. Cultures are incubated for three days, then ³H-thymidine (1 μCi in 25 ml medium) is added and the incubation continues overnight after which it is harvested and counted in the β-counter.

Example 4: Effect of T Cell Receptor Inhibitory Peptides of Viral Origin on Adjuvant-Induced Arthritis in Rats Method A. Arthritis in rats is induced by a single intradermal injection of heat killed MTB in 200 μl squalane (adjuvant) at the base of the tail. To test the peptides and composition of the invention in adjuvant-induced arthritis (AIA) in rats, "TCR inhibitors" or "control" peptides of the invention (1-30 mg) are suspended in one milliliter squalane containing 5 mg of MTB. That is, there is 1 mg MTB and 0.2-6 mg peptide in 0.2 ml of squalane injected intradermally. At regular intervals for up to 28 days, animals are weighed and their arthritic condition is assessed by measurement of ankle thickness and rear paw thickness (with a micrometer) and recording the number of arthritic joints involved. Rats are housed in standard cages after the initial tail injection and allowed access to unlimited water and pellet food. Rats generally develop arthritis 12-14 days after the injection. On day 29, the animals are sacrificed.

Method B. Three-month old female Lewis rats are raised and maintained under pathogen-free conditions. To test the effect of the peptides and composition of the invention on T cell activation in vivo, AIA is used as a model system. AIA is induced by injecting 50 μl of MTB suspended in incomplete Freund's adjuvant (IFA) (0.5 mg/ml) at the base of the tail. At the time of AIA induction, each rat also receives 100 μg of "TCR inhibitors" or "control" peptides of the invention, or PBS dissolved in 50 μl of IFA and mixed with MTB/IFA used to induce AIA. The day of AIA induction is designated as day 0. Disease severity is assessed by direct observation of all 4 limbs in each animal. A relative score between 0 and 4 is assigned to each limb, based on the degree of joint inflammation, redness and deformity; thus the maximum possible score for an individual animal is 16 (WO 2006077601). Arthritis is also quantified by measuring hind limb diameter with a caliper. Measurements are taken on the day of the induction of AIA and 26 days later (at the peak of AIA); the results are presented as the mean ± SEM of the difference between the two values for all the animals in each group. The person who scores the disease should be blinded to the identity of the groups.

Example 5: Effect of T Cell Receptor Inhibitory Peptides of Viral Origin on T Cell Proliferation and Cytokine Production A. Cell Lines and Antigens
(WO 2006077601)

The CD4⁺ T cell clone A2b 21 reacts with the 180-188 epitope of the 65 kDa heat shock protein (HSP65) of *M. tuberculosis* (MTB), this epitope is contained in the peptide MTB 176-190. MTB Strain H37Ra and incomplete Freund's adjuvant (IFA) can be purchased from Difco (Detroit, Mich., USA). Tuberculin purified protein derivative (PPD) can be provided by the Statens Serum institute (Copenhagen, Denmark). PMA, ionomycin, ovalbumin (OVA) and Concanavalin A (Con A) can be purchased from Sigma (USA).

B. T Cell Proliferation

T cell proliferation assays are performed using either lymph node cells (LNC) or the A2b T cell line, which reacts with the MtB 176-190 peptide. Popliteal and inguinal LNC are removed 26 days after the injection of MTB in IFA, when strong T cell responses to PPD and MTB 176-190 are detectable. LNC are cultured at a concentration of $2 \times 10^5$ cells per well; $5 \times 10^4$ A2b T cells are stimulated in the presence of irradiated $5 \times 10^5$ thymic antigen presenting cells (APC) per well. The cells are plated in quadruplicates in 200 μl round bottom microtiter wells (Costar Corp., Cambridge, USA), with or without antigen, in the presence of various concentrations of the "TCR inhibitors" or "control" peptides of the invention. For some experiments, the cells are activated with immobilized anti-CD3 antibodies or PMA/ionomycin. Cultures are incubated for 72 hr at 37° C. in a humidified atmosphere of 7.5% $CO_2$. T cell responses are detected by the incorporation of [methyl-3H]-thymidine (Amersham, Buckinghamshire, UK; 1 μCi/well), added during the last 18 hr of incubation. The results of T cell proliferation experiments can be presented as the % of inhibition of the T cell proliferation triggered by the antigen in the absence of the "TCR inhibitors" or "control" peptides of the invention.

C. Cytokine Assays

Supernatants are collected after 72 hr of stimulation, and rat IL-10 and IFNγ are quantified by enzyme-linked immunosorbent assay (ELISA) using, for example, Pharmingen's OPTEIA kit (Pharmingen, San Diego, USA). When needed, cytokine levels can be expressed as percentage of cytokine inhibition relative to cytokine levels when no "TCR inhibitors" or "control" peptides of the invention are present. Otherwise, the cytokines can be shown as pg/ml. The lower limits of detection for these experiments can be 15 pg/ml for IL-10 and IFNy. Cytokine amounts are calculated based on calibration curves constructed using recombinant cytokines as standards.

INCORPORATION BY REFERENCE

All of the patents and publications cited herein are hereby incorporated by reference. Each of the applications and patents cited in this text, as well as each document or reference cited in each of the applications and patents (including during the prosecution of each issued patent;

"application cited documents"), and each of the PCT and foreign applications or patents corresponding to and/or paragraphing priority from any of these applications and patents, and each of the documents cited or referenced in each of the application cited documents, are hereby expressly incorporated herein by reference. More generally, documents or references are cited in this text, either in a Reference List, or in the text itself; and, each of these documents or references ("herein-cited references"), as well as each document or reference cited in each of the herein-cited references (including any manufacturer's specifications, instructions, etc.), is hereby expressly incorporated herein by reference.

The references cited herein throughout, to the extent that they provide exemplary procedural or other details supplementary to those set forth herein, are all specifically incorporated herein by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

I claim:

1. A composition comprising a peptide inhibitor with an amino acid sequence consisting of G-Y-X1-X2-X3-X4-X5-X6-X7-X8-X9, wherein:
   a) X1 is selected from the group consisting of R, K or H;
   b) X2, X3, X4 and X5 are selected from the group consisting of L, I, T or P;
   c) X6 is selected from the group consisting of R, K or H;
   d) X7 is selected from the group consisting of V or Y;
   e) X8 consists of A or F or nothing; and
   f) X9 consists of G or nothing.

2. The composition of claim 1, wherein said peptide inhibtor is attached to a C-terminal and/or an N-terminal sugar conjugate.

3. The composition of claim 2, wherein said sugar conjugate is 1-amino-glucose succinate.

4. The composition of claim 1, wherein said peptide inhbitor is attached to a C-terminal and/or an N-teiminal lipid conjugate.

5. The composition of claim 4, wherein said lipid conjugate is selected from the group comprising 2-aminododecanoate and myristoylate.

6. The compostion of claim 4, wherein said lipid conjugate is selected from the group comprising Gly-Tris-monopalmitate, Gly-Tris-dipalmitate and Gly-Tristripalmitate.

7. The composition of claim 1, wherein said peptide inhibitor is a cyclic peptide.

8. The composition of claim 1, wherein said peptide inhibitor comprises a disulfide-linked dimer.

9. The composition of claim 1, wherein said amino acid sequence has L-amino acids or D-amino acids.

10. The compositon of claim 1, further comprising a therapeutically effective amount of said peptide inhibitor.

11. The composition of claim 1, wherein said peptide inhibitor is a therapeutic drug.

* * * * *